United States Patent
Tan et al.

(10) Patent No.: US 10,551,542 B1
(45) Date of Patent: Feb. 4, 2020

(54) LIGHT MODULES AND DEVICES INCORPORATING LIGHT MODULES

(71) Applicant: CORNING INCORPORATED, Corning, NY (US)

(72) Inventors: Qing Tan, Santa Clara, CA (US); Mario Paniccia, Santa Clara, CA (US); Tim L. Kitchen, Newport News, VA (US)

(73) Assignee: Corning Incorporated, Corning, NY (US)

(*) Notice: Subject to any disclaimer, the term of this patent is extended or adjusted under 35 U.S.C. 154(b) by 0 days.

(21) Appl. No.: 16/216,112

(22) Filed: Dec. 11, 2018

(51) Int. Cl.

| F21V 7/04 | (2006.01) |
|---|---|
| F21V 8/00 | (2006.01) |
| H01L 33/62 | (2010.01) |
| H01L 33/48 | (2010.01) |
| H01L 25/075 | (2006.01) |
| A61L 2/10 | (2006.01) |
| A61L 2/08 | (2006.01) |

(Continued)

(52) U.S. Cl.
CPC ............ *G02B 6/0006* (2013.01); *A61L 2/084* (2013.01); *A61L 2/10* (2013.01); *A61L 2/26* (2013.01); *G02B 6/001* (2013.01); *H01L 25/0753* (2013.01); *H01L 33/483* (2013.01); *H01L 33/62* (2013.01); *A61L 2202/11* (2013.01); *H05K 1/184* (2013.01); *H05K 2201/10106* (2013.01); *H05K 2201/10121* (2013.01)

(58) Field of Classification Search
CPC ..... G02B 6/0006; G02B 6/0001; A61L 2/084; A61L 2/26; A61L 2/10; A61L 2201/10101; H01L 33/62; H01L 33/483; H01L 25/0753; H05K 2201/10106; H05K 2201/10121; H05K 1/184
See application file for complete search history.

(56) References Cited

U.S. PATENT DOCUMENTS

| 4,186,996 A | 2/1980 | Bowen et al. |
| 4,192,574 A | 3/1980 | Henry et al. |
| 4,316,204 A | 2/1982 | Inagaki et al. |

(Continued)

FOREIGN PATENT DOCUMENTS

| EP | 0241955 A1 | 10/1987 |
| FR | 2504693 A | 10/1982 |

(Continued)

*Primary Examiner* — Ali Alavi
(74) *Attorney, Agent, or Firm* — Payal A. Patel

(57) ABSTRACT

According to one implementation an assembly is provided that facilitates a coupling of one or more light diffusing optical fibers to one or more light emitting diodes. According to one implementation the assembly includes a light emitting diode positioned inside a cavity of a frame that is equipped with means to directly or indirectly electrically couple the anode and cathode of the light emitting diode to a printed circuit board. A proximal end portion of the light diffusing optical fiber is supported inside a through opening of a lid positioned over a front side of the frame. The light diffusing optical fiber includes a core that is surround by a cladding. According to some implementations the proximal end of the light diffusing optical fiber is butt-coupled to the light emitting diode with there being no gap between the proximal end of the fiber and the light emitting side of the light emitting diode.

19 Claims, 44 Drawing Sheets

(51) Int. Cl.
*A61L 2/26* (2006.01)
*H05K 1/18* (2006.01)

(56) References Cited

U.S. PATENT DOCUMENTS

| | | | |
|---|---|---|---|
| 4,385,797 A | 5/1983 | Dubois et al. | |
| 4,399,453 A | 8/1983 | Berg et al. | |
| 4,461,538 A | 7/1984 | Breed, III et al. | |
| 4,639,077 A | 1/1987 | Dobler | |
| 4,709,979 A | 12/1987 | Spodati et al. | |
| 4,725,128 A | 2/1988 | Bornzin et al. | |
| 5,000,536 A | 3/1991 | Anderson et al. | |
| 5,065,011 A | 11/1991 | Fujihara et al. | |
| 5,273,041 A * | 12/1993 | Richards | A61B 5/055 600/411 |
| 5,647,044 A | 7/1997 | Basavanhally et al. | |
| 5,812,571 A | 9/1998 | Peters | |
| 6,231,245 B1 | 5/2001 | Buschelberger et al. | |
| 6,588,942 B1 | 7/2003 | Weld et al. | |
| 6,659,659 B1 | 12/2003 | Malone | |
| 6,832,860 B2 | 12/2004 | Yoon et al. | |
| 6,874,950 B2 | 4/2005 | Colgan et al. | |
| 7,111,992 B2 | 9/2006 | Kaneko | |
| 7,207,729 B2 | 4/2007 | Blom et al. | |
| 7,226,218 B2 | 6/2007 | Wang et al. | |
| 7,229,216 B2 | 6/2007 | Yang | |
| 7,347,632 B2 | 3/2008 | Farr | |
| 7,478,955 B2 | 1/2009 | Murry et al. | |
| 7,553,092 B2 | 6/2009 | Choi et al. | |
| 9,385,249 B2 | 7/2016 | Motohara | |
| 9,874,706 B2 | 1/2018 | Miyahara et al. | |
| 2003/0210873 A1 | 11/2003 | Moretti | |
| 2004/0037514 A1 | 2/2004 | Marion et al. | |
| 2004/0151442 A1 | 8/2004 | Scruggs et al. | |
| 2006/0056778 A1 | 3/2006 | Wang et al. | |
| 2006/0239621 A1 | 10/2006 | Lo et al. | |
| 2007/0189677 A1 | 8/2007 | Murry et al. | |
| 2014/0286363 A1 | 9/2014 | Kasai | |
| 2015/0309272 A1 * | 10/2015 | Cobb | G02B 6/4256 385/93 |
| 2015/0346411 A1 * | 12/2015 | Bauco | F21V 31/005 362/553 |
| 2017/0040768 A1 | 2/2017 | Waclawik | |

FOREIGN PATENT DOCUMENTS

| | | |
|---|---|---|
| JP | S5229749 A | 3/1977 |
| JP | S55166973 A | 12/1980 |
| JP | S5784414 A | 5/1982 |

* cited by examiner

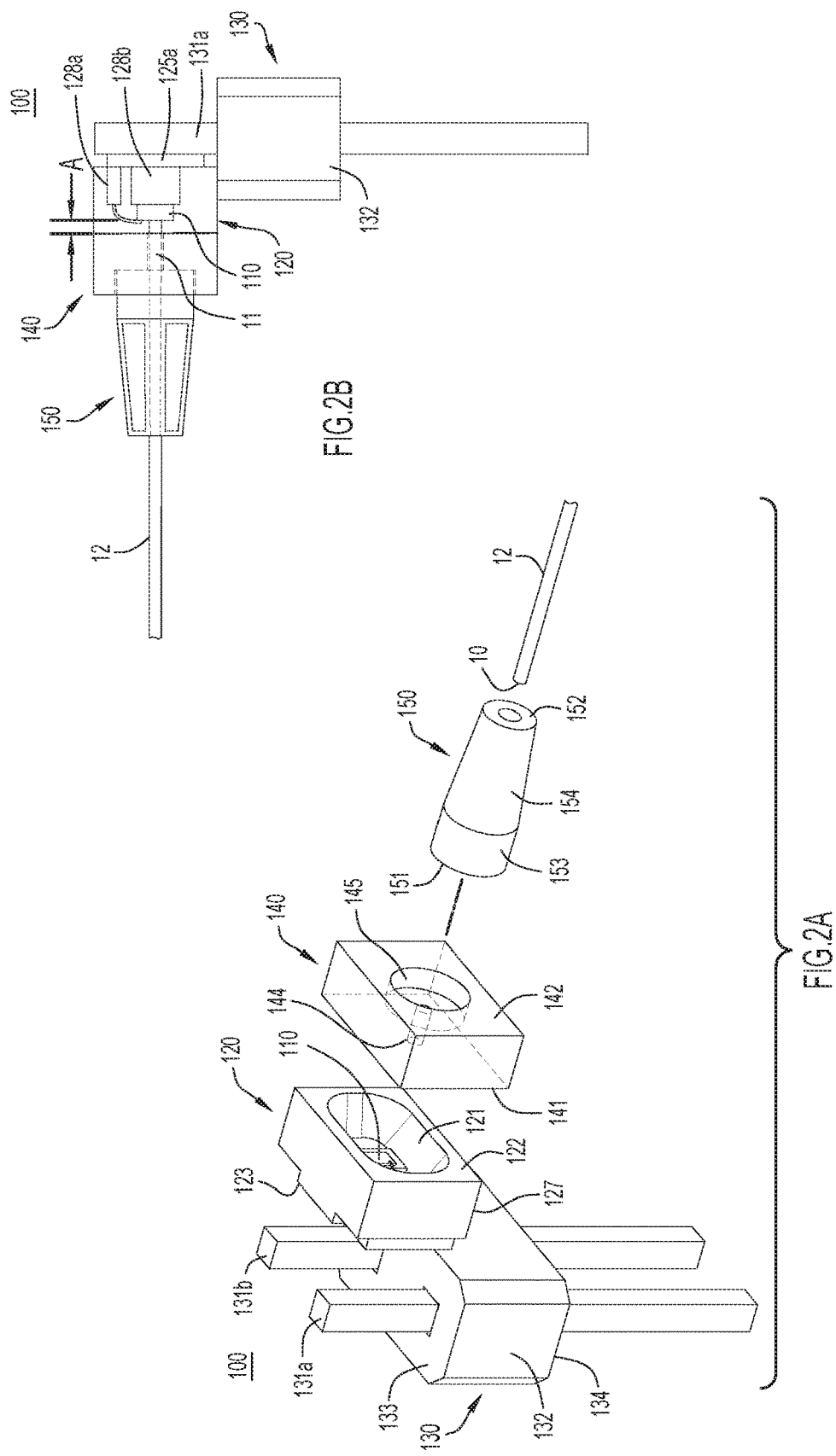

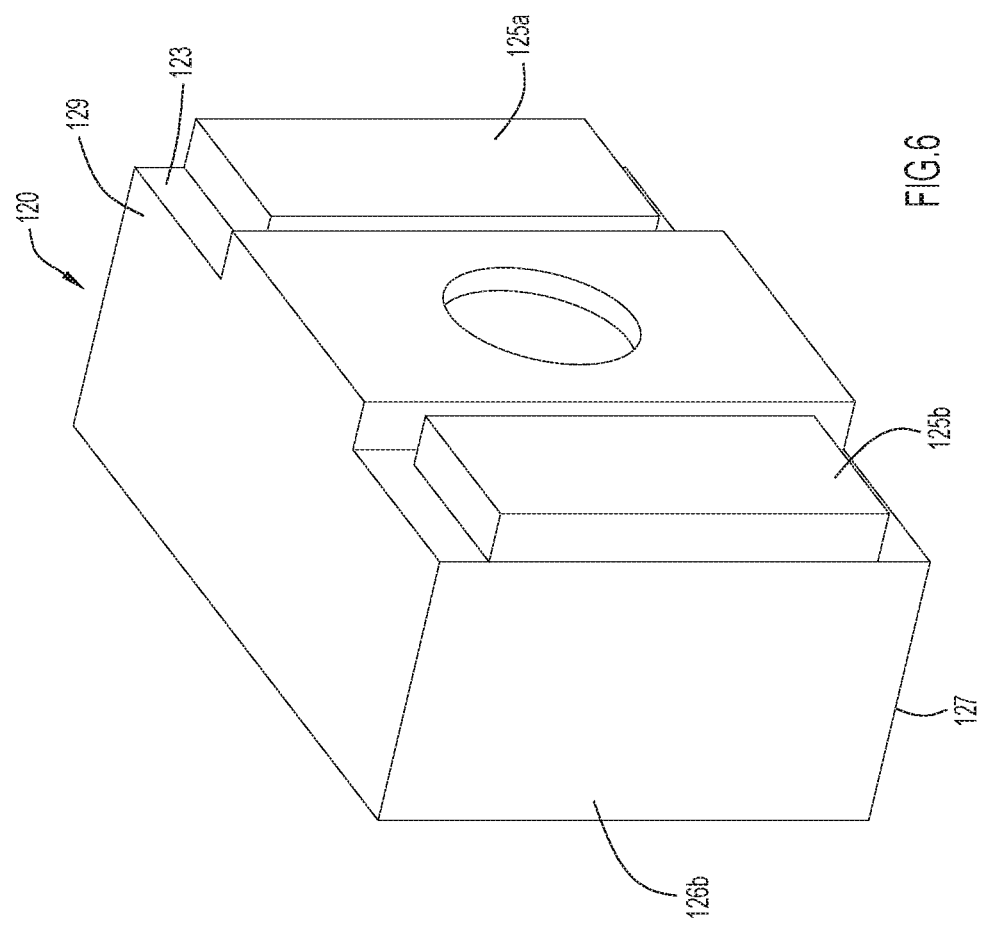

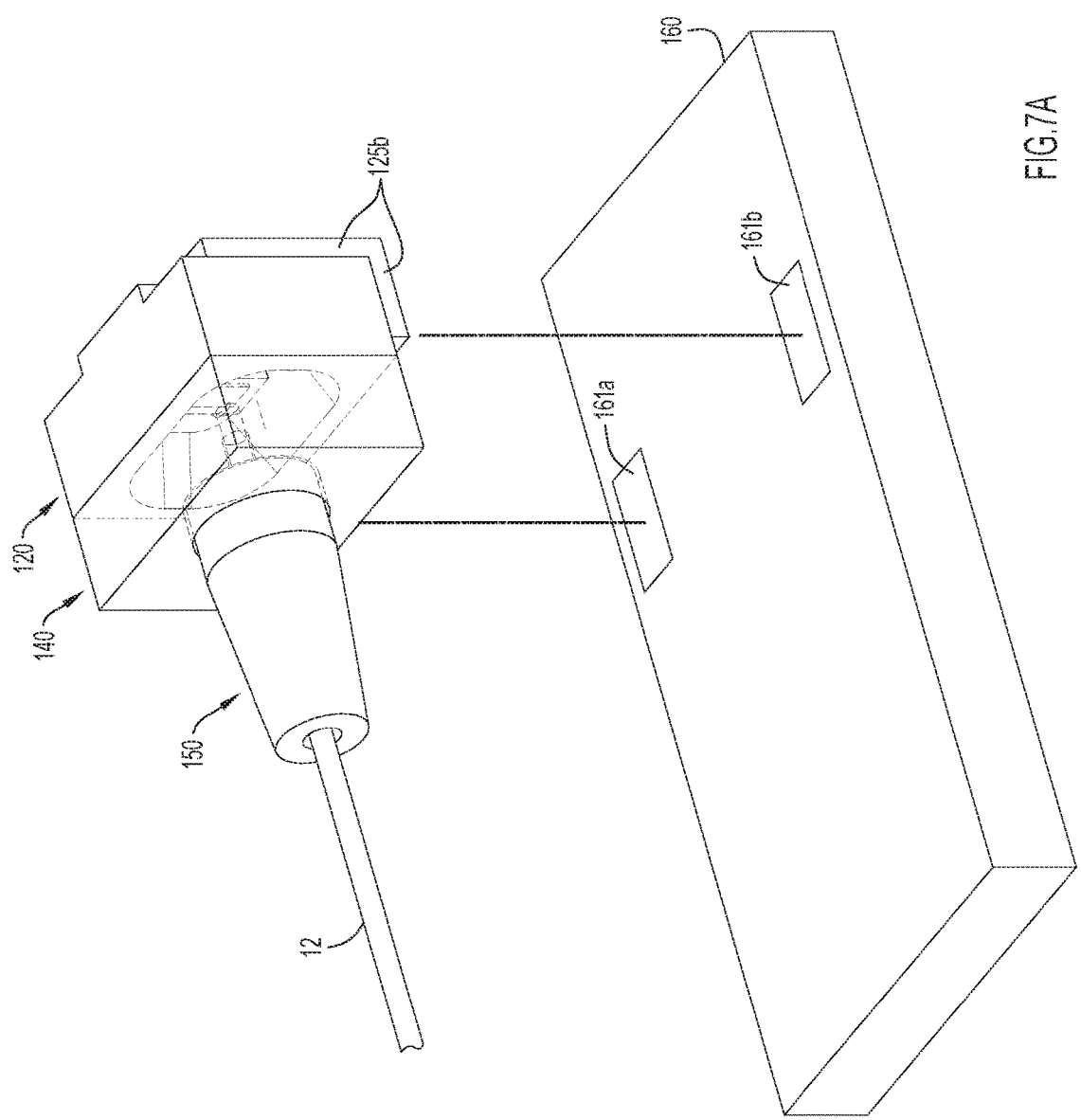

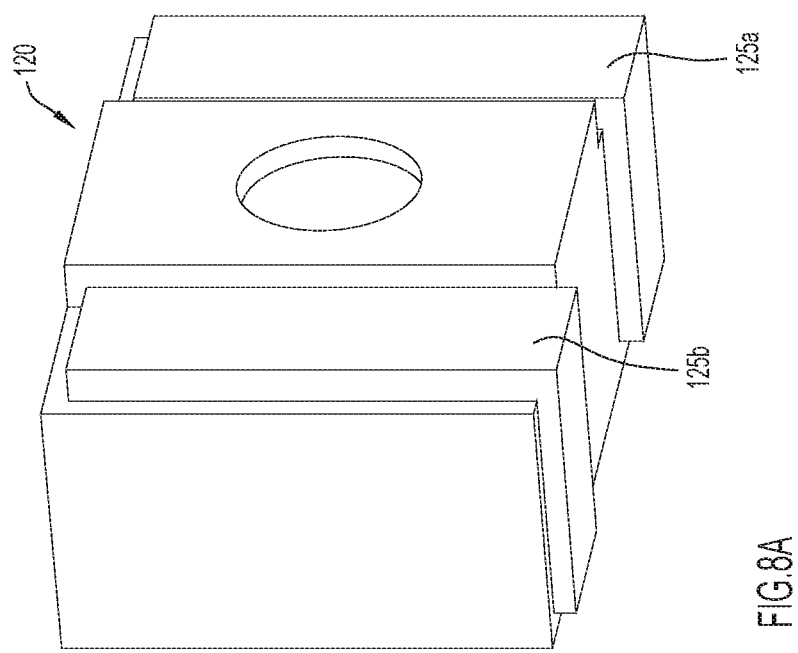

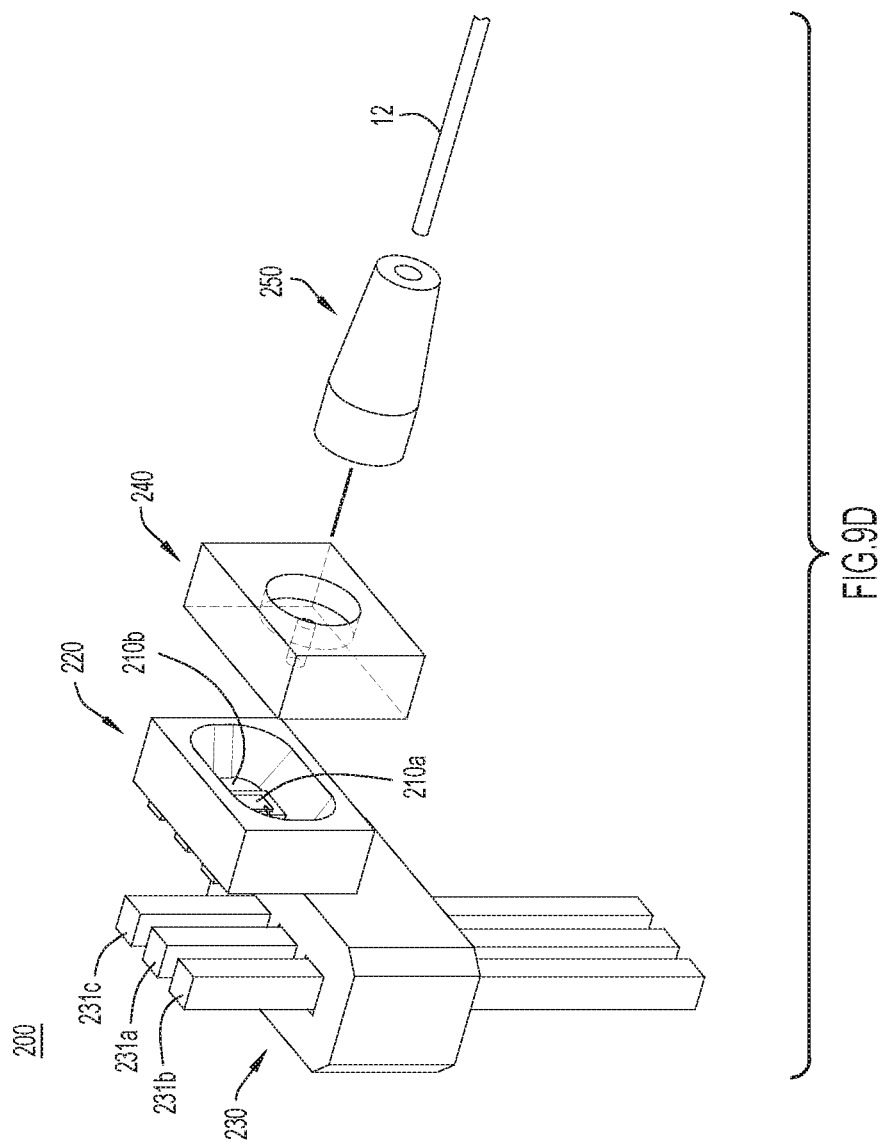

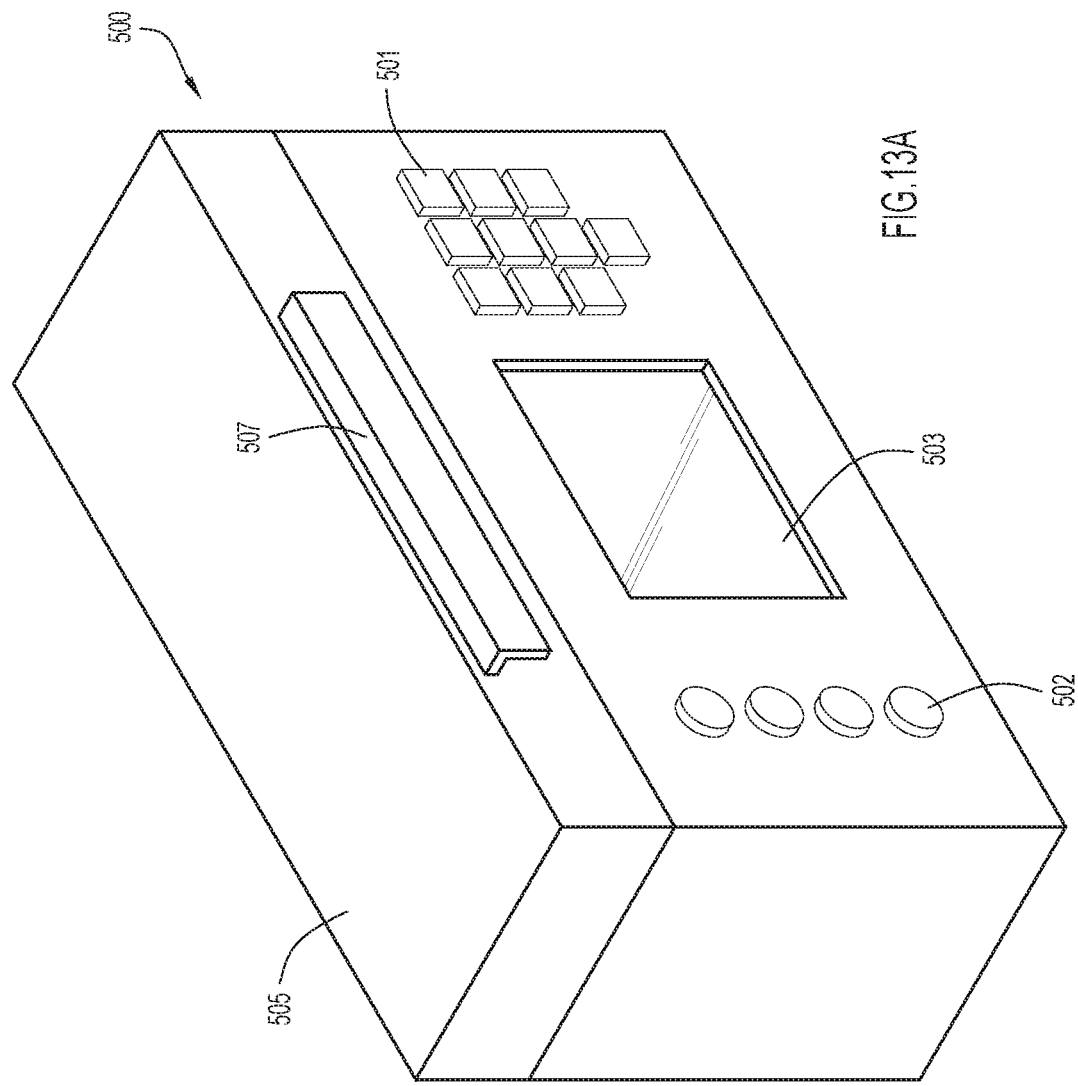

LIGHT MODULES AND DEVICES INCORPORATING LIGHT MODULES

TECHNICAL FIELD

The present invention relates to light modules configured to deliver light (e.g. visible, infrared and ultraviolet light) into an optical fiber, such as a light diffusing optical fiber.

SUMMARY OF THE DISCLOSURE

According to some implementations assemblies are provided that comprise:

an apparatus having an external surface susceptible to bacterial contamination, the apparatus comprising:

a housing having an external surface and internal channel, the housing being made of a material that is transparent to bacterial disinfecting ultraviolet or blue light;

a first light emitting diode having an energized state and a de-energized state, in the energized state the first light emitting diode emits bacterial disinfecting ultraviolet or blue light and in the de-energized state the first light emitting diode does not emit light;

a second light emitting diode having an energized state and a de-energized state, in the energized state the second light emitting diode emits visible light and in the de-energized state the first light emitting diode does not emit light;

a light diffusing optical fiber residing in the internal channel and configured to transmit both visible light and bacterial disinfecting ultraviolet or blue light, the light diffusing optical fiber being optically coupled to both the first and second light emitting diodes.

According to some implementations assemblies are provided that comprise:

an apparatus having an external surface susceptible to bacterial contamination, the apparatus comprising:

a housing having an external surface and internal channel, the housing being made of a material that is transparent to bacterial disinfecting ultraviolet or blue light;

a first light emitting diode having an energized state and a de-energized state, in the energized state the first light emitting diode emits bacterial disinfecting ultraviolet or blue light and in the de-energized state the first light emitting diode does not emit light;

a second light emitting diode having an energized state and a de-energized state, in the energized state the second light emitting diode emits bacterial disinfecting ultraviolet or blue light and in the de-energized state the second light emitting diode does not emit light;

a third light emitting diode having an energized state and a de-energized state, in the energized state the second light emitting diode emits visible light and in the de-energized state the first light emitting diode does not emit light;

a light diffusing optical fiber residing in the internal channel and configured to transmit both visible light and bacterial disinfecting ultraviolet or blue light, the light diffusing optical fiber being optically coupled to the first, second and third light emitting diodes.

According to some implementations assemblies are provided that comprise:

a frame including a front side, a backside and a cavity located between the front side and backside that opens to the front side;

first and second electrically conductive pads located on the frame;

a first light emitting diode having an anode and a cathode, the first light emitting diode being located inside the cavity of the frame with the anode and cathode respectively being electrically coupled to the first and second electrically conductive pads;

a first optical fiber having a core and a cladding surrounding the core, the first optical fiber including a proximal end portion having a first light receiving end that is butt-coupled to the first light emitting diode;

a lid located distal to the first light emitting diode, the lid having a front side, a backside, and a through opening that extends between and through the front side and backside of the lid, the backside of the lid being attached to the front side of the frame, the first optical fiber extending through and being supported in the through opening; and a printed circuit board having a voltage terminal and a ground terminal, the first electrically conductive pad of the frame being electrically connected to the voltage terminal and the second electrically conductive pad of the frame being electrically connected to the ground terminal.

According to some implementations assemblies are provided that comprise:

a frame including a front side, a backside and a cavity located between the front side and backside that opens to the front side;

a first light emitting diode being located inside the cavity of the frame;

a first optical fiber having a core and a cladding that surrounds the core, the first optical fiber including a proximal end portion having a first light receiving end that is optically coupled to the first light emitting diode; and a lid constructed of a rigid material located distal to the first light emitting diode, the lid having a front side, a backside, and a through opening that extends between and through the front side and backside of the lid, the backside of the lid being attached to the front side of the frame, the first optical fiber extending through and being supported in the through opening, the through opening of the lid having a length dimension and a portion of the first optical fiber residing in the through opening having an outer diameter dimension, the length dimension being greater than the outer diameter dimension.

According to some implementations assemblies are provided that comprise:

a frame including a front side, a backside and a cavity located between the front side and backside that opens to the front side;

first, second and third electrically conductive pads located on the frame;

a first light emitting diode having an anode and a cathode, the first light emitting diode being located inside the cavity of the frame with the anode and cathode respectively being electrically coupled to the first electrically conductive pad and the third electrically conductive pad;

a second light emitting diode having an anode and a cathode, the second light emitting diode being located inside the cavity of the frame with the anode and cathode respectively being electrically coupled to the second electrically conductive pad and the cathode third electrically conductive pad;

a first light diffusing optical fiber having a core and a cladding surrounding the core, the core having a proximal end that is butt-coupled to the first and second light emitting diodes;

a lid having a front side, a backside, and a through opening that extends between and through the front side and backside of the lid, the backside of the lid being attached to the front side of the frame, the first light diffusing optical fiber extending through the through opening; and a printed circuit board having first and second power supply voltage terminals and a power supply ground terminal, the first and second electrically conductive pads of the frame being respectively electrically coupled to the first and second voltage terminals and the third electrically conductive pad of the frame being electrically coupled to the ground terminal.

According to some implementations assemblies are provided that comprise:

a frame including a front side, a backside and a cavity located between the front side and backside that opens to the front side;

first, second, third and fourth electrically conductive pads located on the frame;

a first light emitting diode having an anode and a cathode, the first light emitting diode being located inside the cavity of the frame with the anode and cathode respectively being electrically connected to the first and fourth electrically conductive pad;

a second light emitting diode having an anode and a cathode, the second light emitting diode being located inside the cavity of the frame with the anode and cathode respectively being electrically connected to the second and fourth electrically conductive pad;

a third light emitting diode having an anode and a cathode, the third light emitting diode being located inside the cavity of the frame with the anode and cathode respectively being electrically connected to the third and fourth electrically conductive pad;

a first light diffusing optical fiber having a core and a cladding surrounding the core, the core having a proximal end that is butt-coupled to the first, second and third light emitting diodes;

a lid having a front side, a backside, and a through opening that extends between and through the front side and backside of the lid, the backside of the lid being attached to the front side of the frame, the first light diffusing optical fiber extending through the through opening; and a printed circuit board having first, second and third power supply voltage terminals and a power supply ground terminal, the first, second, third and fourth anode electrically conductive pads being respectively electrically coupled to the first, second and third voltage terminals and to the ground terminal.

According to some implementations assemblies are provided that comprise:

a frame including a front side, a backside and a cavity located between the front side and backside that opens to the front side;

a first and second electrically conductive pads located on the frame;

a first light emitting diode having an anode and a cathode, the first light emitting diode being located inside the cavity of the frame with the anode and cathode respectively being electrically connected to the first and second electrically conductive pad;

a first light diffusing optical fiber having a core and a cladding surrounding the core, the core of the first light diffusing optical fiber having a proximal end that is butt-coupled to the first light emitting diode;

a second light diffusing optical fiber having a core and a cladding surrounding the core, the core of the second light diffusing optical fiber having a proximal end that is butt-coupled to the first light emitting diode;

a lid having a front side, a backside, and a through opening that extends between and through the front side and backside of the lid, the backside of the lid being attached to the front side of the frame, the first and second light diffusing optical fibers extending through the through opening; and a printed circuit board having a voltage terminal and a ground terminal, the first electrically conductive pad being electrically coupled to voltage terminal and the second electrically conductive pad being electrically coupled to the ground terminal.

According to some implementations assemblies are provided that comprise:

a first frame including a front side, a backside and a cavity located between the front side and backside that opens to the front side;

first and second electrically conductive pads located on the first frame;

a first light emitting diode having an anode and a cathode, the first light emitting diode being located inside the cavity of the first frame with the anode and cathode respectively being electrically coupled to the first and second electrically conductive pad;

a first light diffusing optical fiber having a core and a cladding surrounding the core, the first light diffusing optical fiber having a first end and an opposite second end, the first end being optically coupled to the first light emitting diode;

a first lid having a front side, a backside, and a through opening that extends between and through the front side and backside of the first lid, the backside of the first lid being attached to the front side of the first frame, a first portion of the first light diffusing optical fiber extending through and being supported in the through opening of the first lid;

a first printed circuit board having a voltage terminal and a ground terminal, the first electrically conductive pad of the first frame being electrically coupled to the voltage terminal of the first printed circuit board and the second electrically conductive pad of the first frame being electrically coupled to the ground terminal of the printed circuit board:

a second frame including a front side, a backside and a cavity located between the front side and backside that opens to the front side;

first and second electrically conductive pads located on the second frame;

a second light emitting diode having an anode and a cathode, the second light emitting diode being located inside the cavity of the second frame with the anode and cathode respectively being electrically coupled to the first and second electrically conductive pads of the second frame;

the second end of the first light diffusing optical fiber being optically coupled to the second light emitting diode;

a second lid having a front side, a backside, and a through opening that extends between and through the front side and backside of the second lid, the backside of the second lid being attached to the front side of the second frame, a second portion of the first light diffusing optical fiber extending through and being supported in the through opening of the second lid; and a second printed circuit board having a voltage terminal and a ground terminal, the first electrically conductive pad of the second frame being electrically connected to the voltage terminal of the second printed circuit board and the second electrically conductive pad of the second frame being electrically connected to the ground terminal of the second printed circuit board.

Additional implementations are also provided as disclosed in the text that follows.

BRIEF DESCRIPTION OF THE DRAWINGS

FIG. 2A is an exploded perspective view of a light module according to one implementation.

FIG. 2B is a cross-section view of the light module of FIG. 2A in an assembled state.

FIG. 6 is a perspective view showing a backside of a frame in which the light emitting diode is housed.

FIG. 7A is a perspective view of a light module and printed circuit board according to one implementation.

FIG. 8A is a perspective view showing a backside and bottom side of the light module shown in FIG. 7B.

FIG. 9D illustrates an exploded view of a light module according to one implementation incorporating the features of FIGS. 9A-C and being electrically coupled to a printed circuit board by a pin connector having three pins.

FIG. 13A illustrates an exemplary medical apparatus that is routinely exposed to bacteria, viruses and other infectious matter wherein a handle of the medical apparatus includes on or multiple light modules that are configured to emit ultraviolet light in a manner sufficient to kill the bacteria, viruses and other infectious matter.

DETAILED DESCRIPTION

Figure 1A:
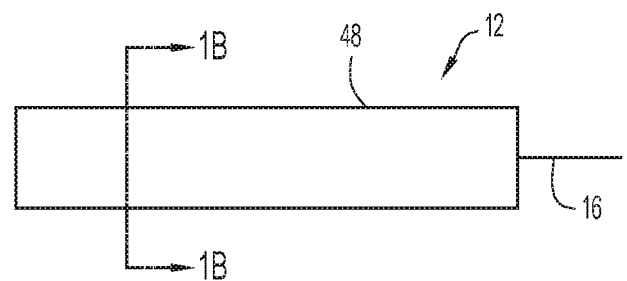
FIG. 1A is a side view of a light diffusing optical fiber according to one implementation.

In the following detailed description, numerous specific details are set forth in order to provide a thorough understanding of the inventive concepts and how they may be practiced in particular implementations. However, it will be understood that those inventive concepts may be practiced without these specific details. In other instances, well-known methods, procedures and techniques have not been described in detail so as not to obscure the present disclosure.

The disclosure below is set forth in relation to particular implementations and with reference to certain drawings; however, the implementations described herein are not limited to those illustrated in the drawings. Moreover, it is to be understood that the drawings described herein are schematic in nature and are provided only to assist in understanding of the described implementations. In the drawings, the sizes of some of the elements may be exaggerated and not drawn to scale for illustrative purposes.

Figure 1B:
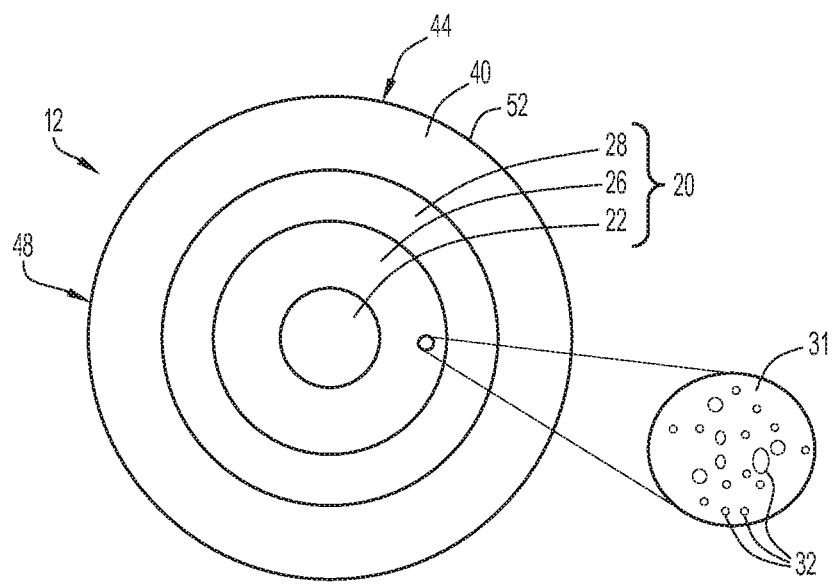
FIG. 1B is a cross-section view of FIG. 1A along lines 1B-1B.

FIG. 1A is a schematic side view of a section of an example of a light diffusing fiber with a plurality of voids in the core of the light diffusing optical fiber 12 having a central axis 16. FIG. 1B is a schematic cross-section of a light diffusing optical fiber 12 as viewed along the direction 1B-1B in FIG. 1A. Light diffusing fiber 12 can be, for example, an optical fiber with a nano-structured fiber region having periodic or non-periodic nano-sized structures 32 (for example voids). In an example implementation, fiber 12 includes a core 20 divided into three sections or regions. These core regions are: a solid central portion 22, a nano-structured ring portion (inner annular core region) 26, and outer, solid portion 28 surrounding the inner annular core region 26. A cladding region 40 surrounds the annular core 20 and has an outer surface. The cladding 40 may have low refractive index to provide a high numerical aperture. The cladding 40 can be, for example, a low index polymer such as UV or thermally curable fluoroacrylate or silicone.

An optional coating 44 surrounds the cladding 40. Coating 44 may include a low modulus primary coating layer and a high modulus secondary coating layer. In at least some implementations, coating layer 44 comprises a polymer coating such as an acrylate-based or silicone based polymer. In at least some implementations, the coating has a constant diameter along the length of the fiber.

In other exemplary embodiments described below, coating 44 is designed to enhance the distribution and/or the nature of radiated light that passes from core 20 through cladding 40. The outer surface of the cladding 40 or the of the outer of optional coating 44 represents the sides 48 of fiber 12 through which light traveling in the fiber is made to exit via scattering, as described herein.

A protective jacket (not shown) optionally covers the cladding 40.

In some implementations, the core region 26 of light diffusing fiber 12 comprises a glass matrix 31 with a plurality of non-periodically disposed nano-sized structures (e.g., voids) 32 situated therein, such as the example voids shown in detail in the magnified inset of FIG. 1B. In another example implementation, voids 32 may be periodically disposed, such as in a photonic crystal optical fiber, wherein the voids may have diameters between about $1\times10^{-6}$ m and $1\times10^{-5}$ m. Voids 32 may also be non-periodically or randomly disposed. In some exemplary implementations, glass 31 in region 26 is fluorine-doped silica, while in other implementations the glass may be an undoped pure silica.

The nano-sized structures 32 scatter the light away from the core 20 and toward the outer surface of the fiber. The scattered light is then diffused through the outer surface of the fiber 12 to provide the desired illumination. That is, most of the light is diffused (via scattering) through the sides of the fiber 12, along the fiber length.

According to some implementations the core 20 has a diameter in the range of 125-300 μm and the overall diameter of the fiber system, including the protective jacket, is in the range of 0.7 to 1.2 mm.

A detailed description of exemplary light diffusing optical fibers may be found in Reissue Pat. No. RE46,098 whose content is incorporated herein by reference in its entirety.

A light diffusing optical fiber may be constructed differently than that illustrated in FIGS. 1A and 1B. In the context of the present disclosure a light diffusing optical fiber is an optical fiber that is configured to scatter or diffuse light radially out of the fiber. More specifically, light is guided radially away from the core along its length to provide illumination for applications, such as illuminated signage, displays, certain lighting fixtures, etc. Other applications may include a dispersion of infrared light used in military or law enforcement equipment and clothing for identification purposes. Other applications may include a dispersion of disinfecting light (e.g. ultraviolet light and blue light) to disinfect any of a host of devices including, for example, door handles, medical equipment, food processing equipment, etc. The optical fiber core may be fabricated from glass or other suitable light-transmissive materials.

Figure 2C:
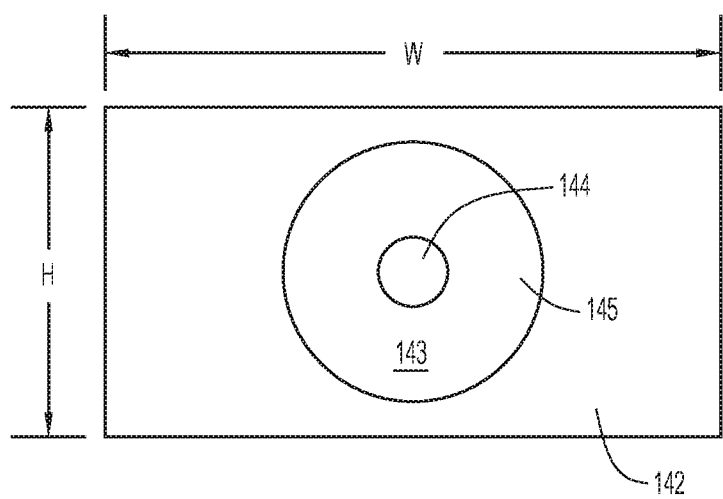
FIG. 2C is a front view of the lid shown in FIGS. 2A and 2B.

FIGS. 2A and 2B respectively illustrate an exploded perspective view and a cross-sectional side view of light module 100 according to one implementation wherein the light receiving end 10 of the optical fiber 12 is optically coupled to a light emitting surface 114 located on a front side 111 of an LED 110. The LED 110 resides inside a cavity 121 of a supporting frame 120. The cavity 121 opens to the front side 122 of the frame 120. Although the current disclosure will primarily focus on light modules comprising light diffusing optical fibers that diffuse light along at least a majority or all of its length, it is appreciated that other types of optical waveguides may be employed, such as, for example, transport fibers in which little to no loss of light occurs along its length.

Figure 5C:
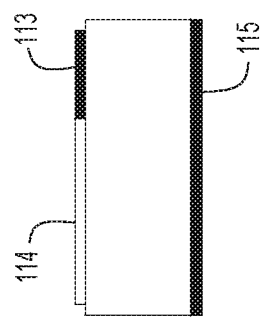
FIGS. 5A-C respectively show a front view, bottom view and side view of a light emitting diode according to one implementation.
Figure 5B:
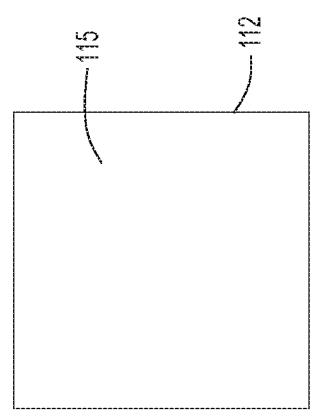
Figure 5A:
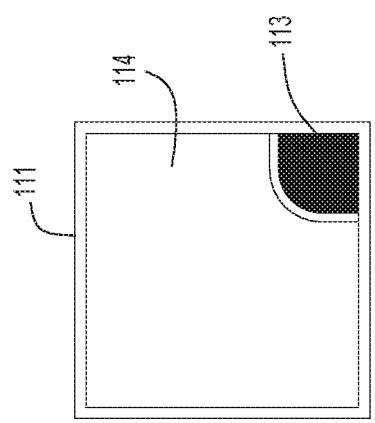

According to one example the LED 110 comprises a structure like that shown in FIGS. 5A-C. In the LED configuration of FIGS. 5A-C the LED 110 includes a light emitting front side 111 that is intended to face the light receiving end 10 of the optical fiber 12. According to the implementation of FIGS. 5A-C, the front side of the LED 110 includes an anode 113 and a light emitting surface 114. The cathode 115 of the LED 110 resides on a backside surface 112 thereof as shown in FIGS. 5B and 5C. According to one implementation the LED 110 has a thickness of 170 μm with the front side and bottom side being 380 μm².

Figure 4A:
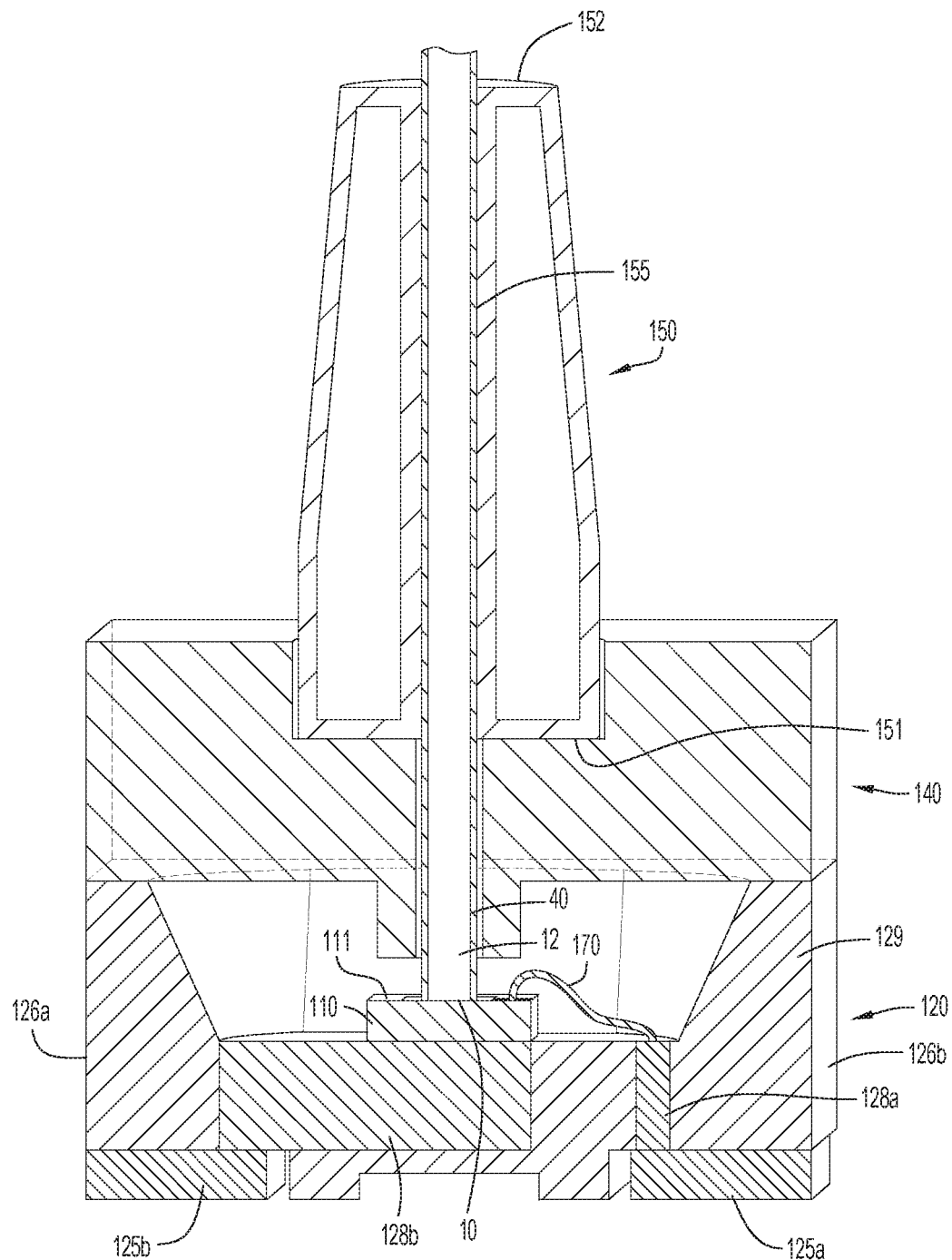
FIG. 4A is a top cross-section view of the light module of FIG. 2B showing the optical fiber being butt-coupled to a front face of a single light emitting diode.
Figure 4B:
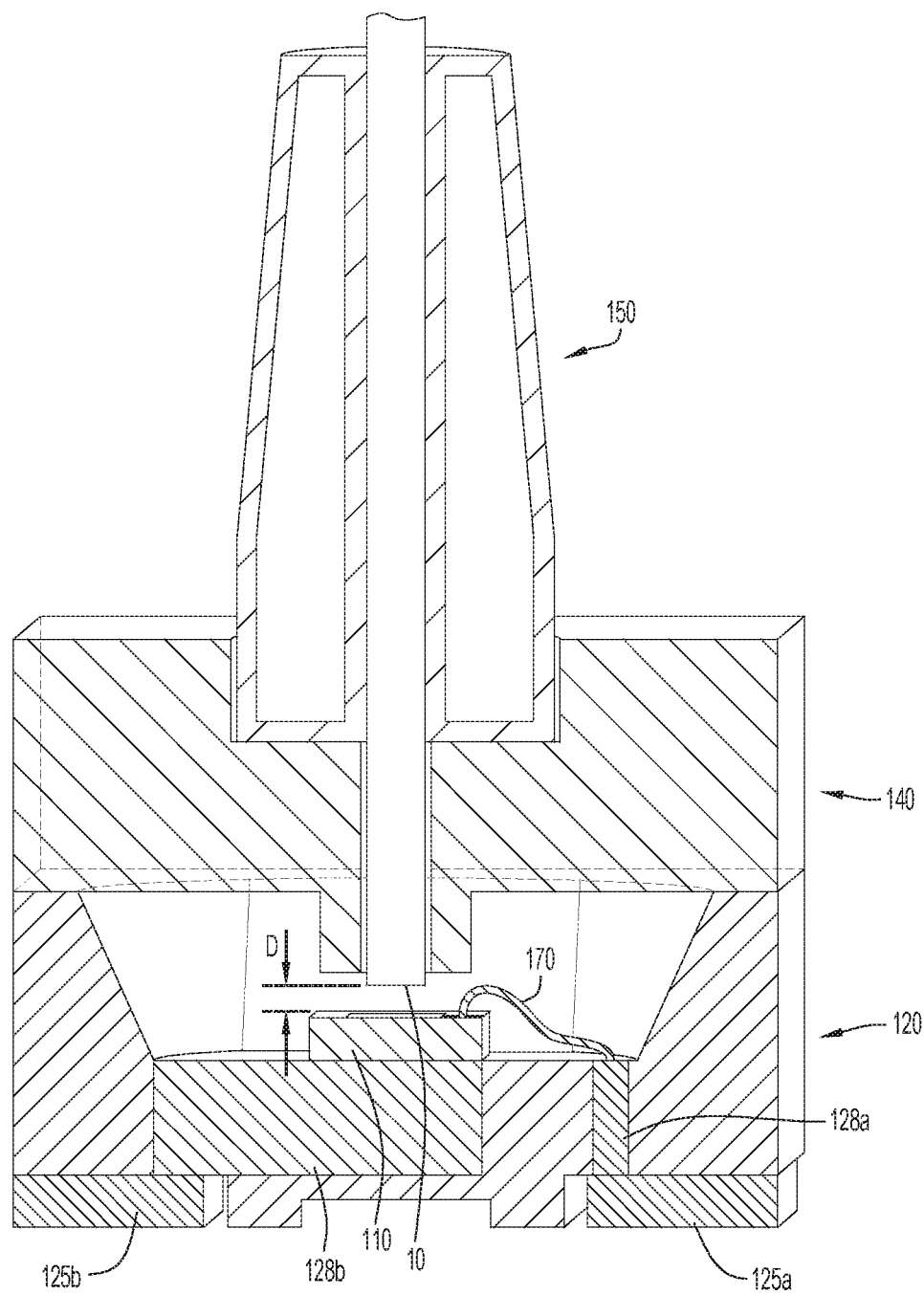
FIG. 4B is a top cross-section view of a light module similar to that of FIG. 2B showing the optical fiber being spaced a distanced the front face of the single light emitting diode.

In the implementation shown in FIGS. 2B and 4A the optical fiber 12 is butt-coupled to a light emitting surface 114 located on the front side of the LED 110 with both the fiber core 12 and cladding 40 pressing against the front side 111 of the LED. According to other implementations, as shown in FIG. 4B, the light receiving end 10 of the optical fiber is spaced a distance away from the front side 111 of the LED 110. According to some implementations the distance D separating the light receiving end 10 of the optical fiber 12 and the light emitting surface 114 of the LED 110 is anywhere from a few microns but no greater than three hundred microns, and preferably no greater than two hundred microns.

Figure 4C:
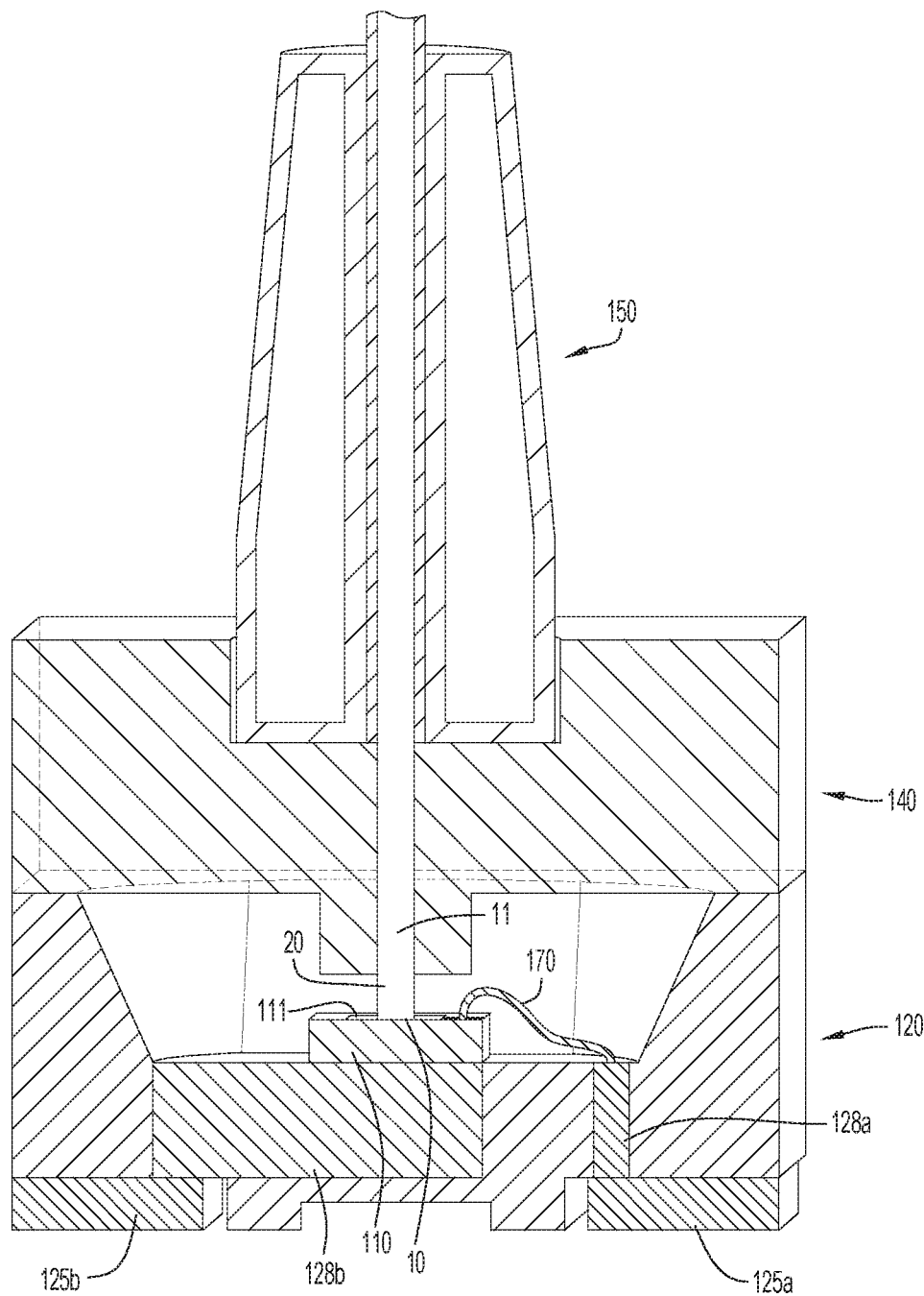
FIG. 4C illustrates a light module similar to that of FIG. 4A with the cladding removed from the light receiving end of the optical fiber.
Figure 4D:
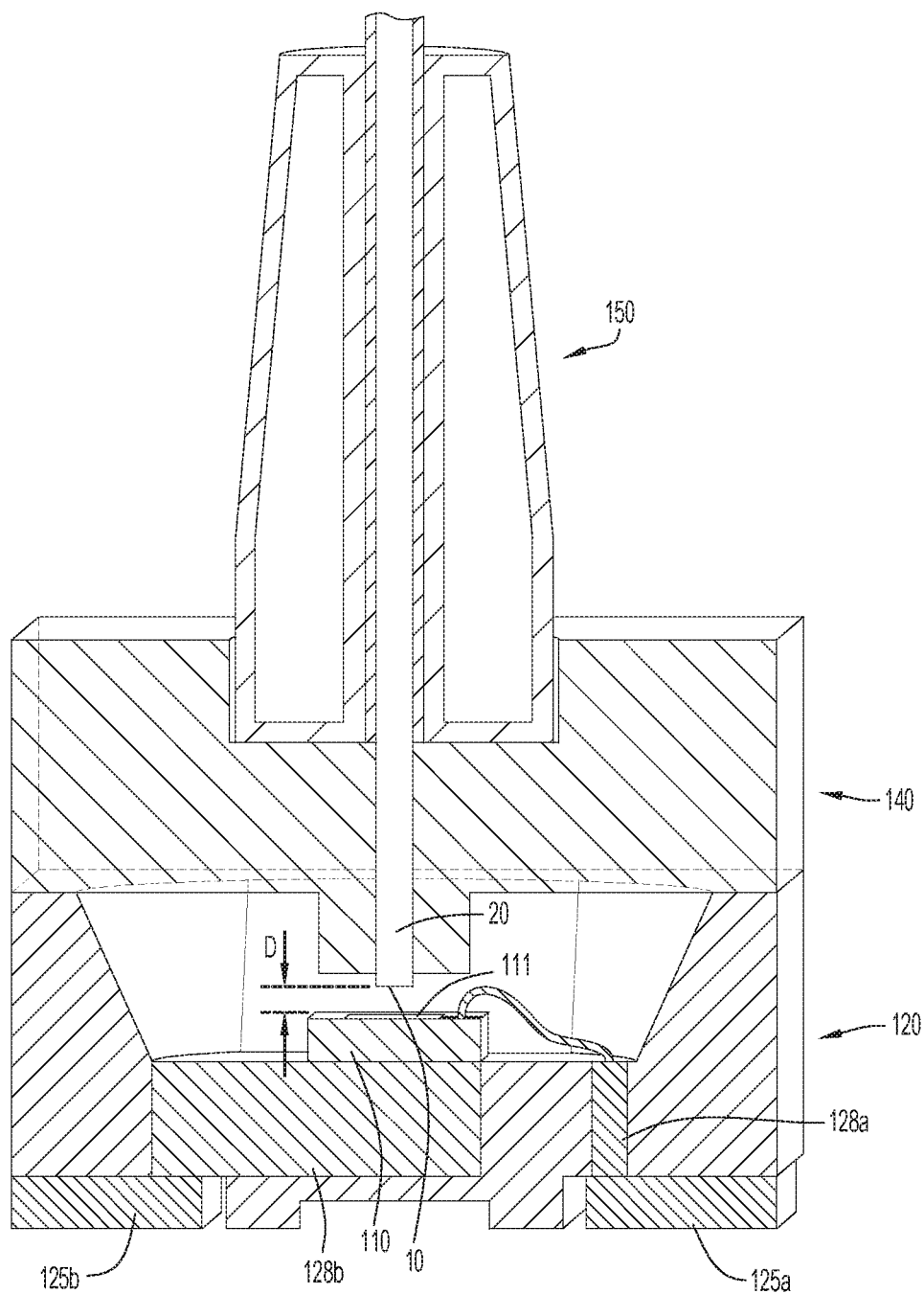
FIG. 4D illustrates a light module similar to that of FIG. 4C with the light receiving end of the core of the optical fiber being spaced a distance away from the front side of the light emitting diode.
Figure 4E:
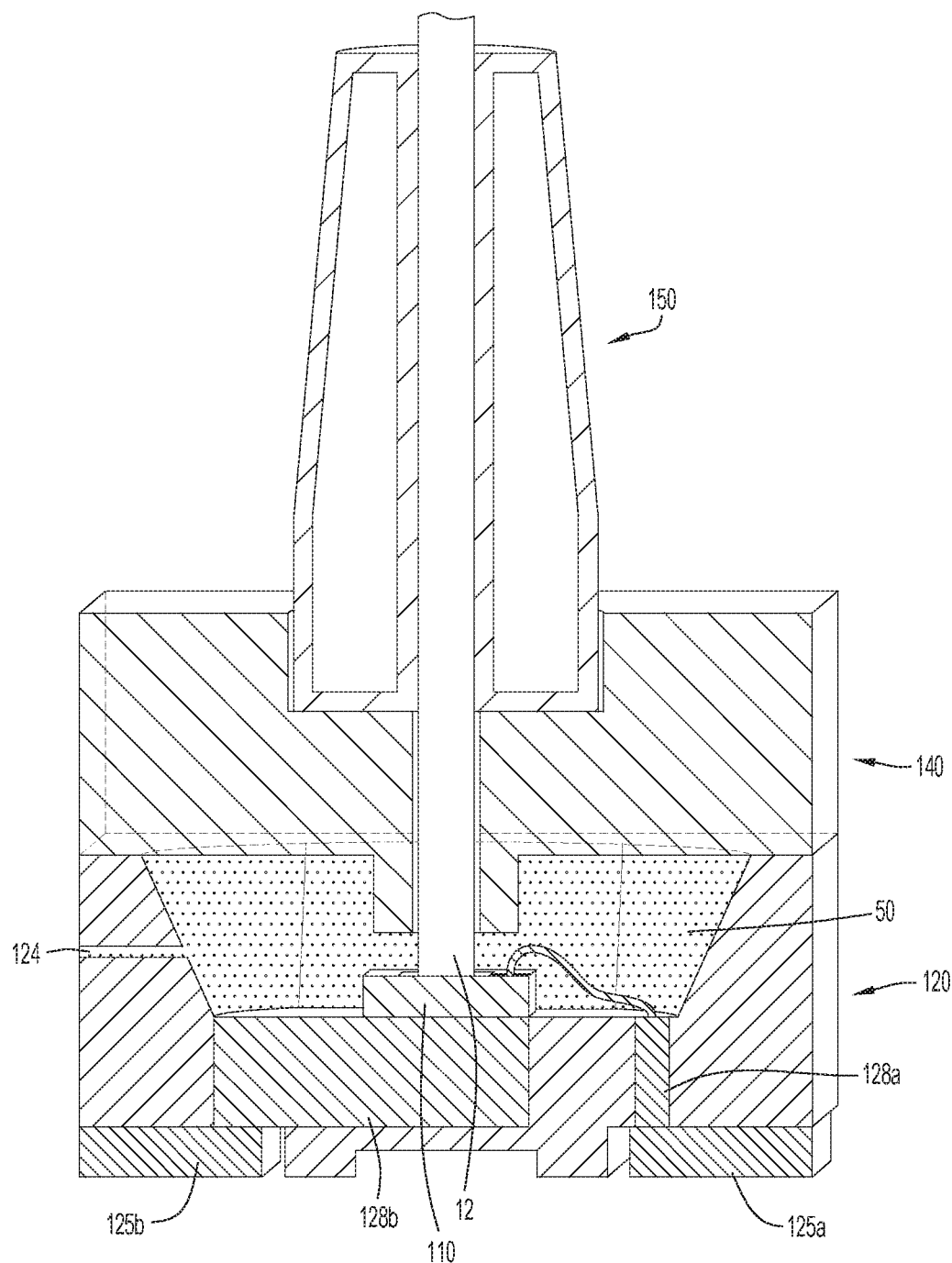
FIG. 4E shows the light module of FIG. 4C with an adhesive disposed inside the cavity of the support frame.

According to other implementations, as shown in FIG. 4C, a proximal-most end segment 11 of the optical fiber 12 is stripped/devoid of the cladding 40 such that only the core 20 of the optical fiber presses against the light emitting surface 114 of the LED. According to other implementations, as shown in FIG. 4D, the core 20 at the light receiving end 10 of the optical fiber is spaced a distance D distal to the light emitting surface 114 of the LED 110. According to some implementations the distance D separating the light receiving end 10 of the optical fiber 12 and the light emitting surface 114 of the LED 110 is anywhere from a few microns but no greater than three hundred microns, and preferably no greater than two hundred microns.

In regard to each of the implementations of FIGS. 4A-D, an adhesive 50 may be introduced in the cavity 121 of the supporting frame 120 to assist in fixing the position of the optical fiber 12 inside the cavity 121 in its coupling relationship with the front side 111 of the LED 110 as respectively shown in FIGS. 4E-H. According to some implementations the supporting frame 120 includes a port 124 through which the adhesive 50 may be introduced into the cavity 121.

Figure 4F:
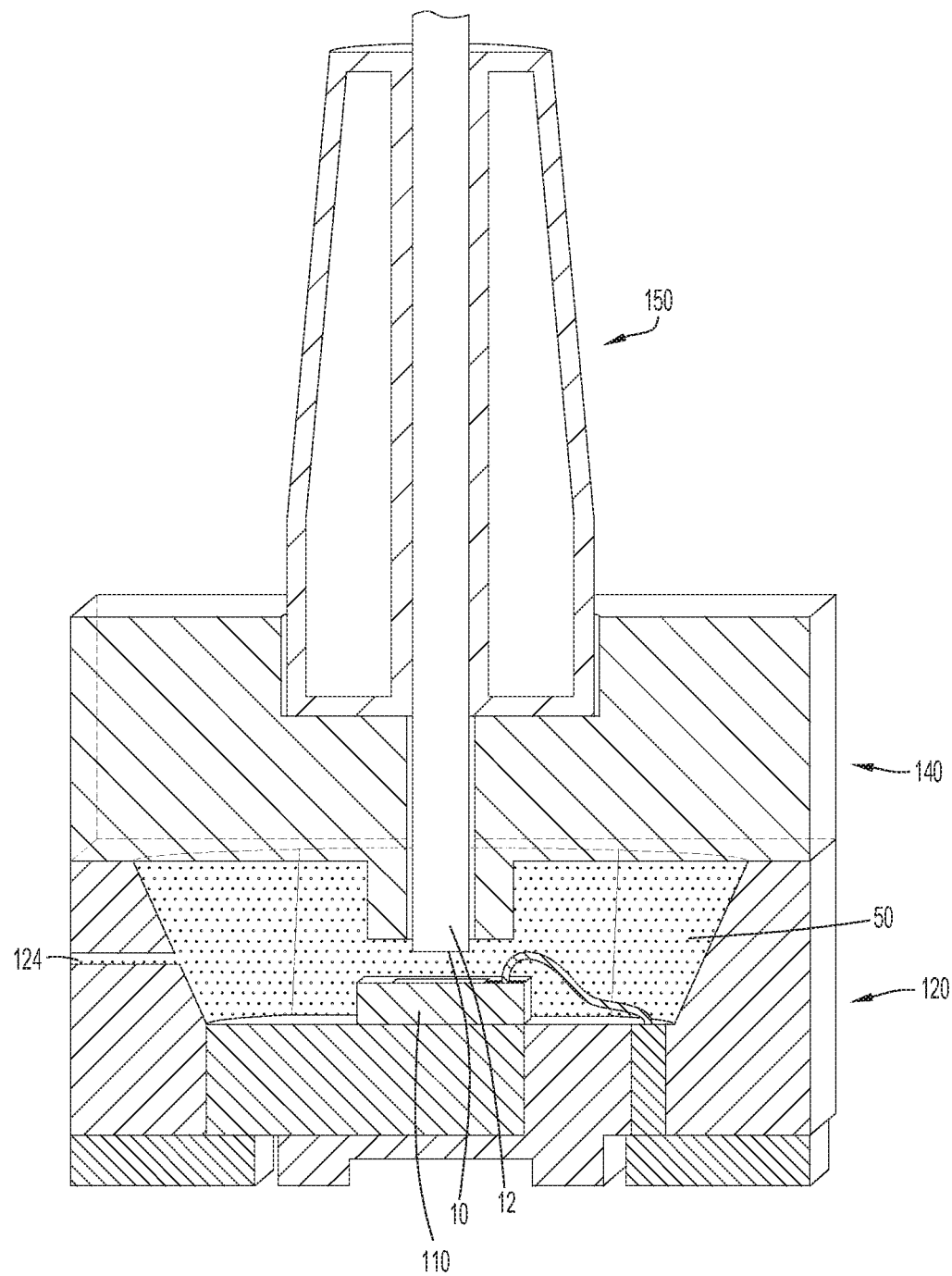
FIG. 4F shows the light module of FIG. 4B with an adhesive disposed inside the cavity of the support frame.
Figure 4G:
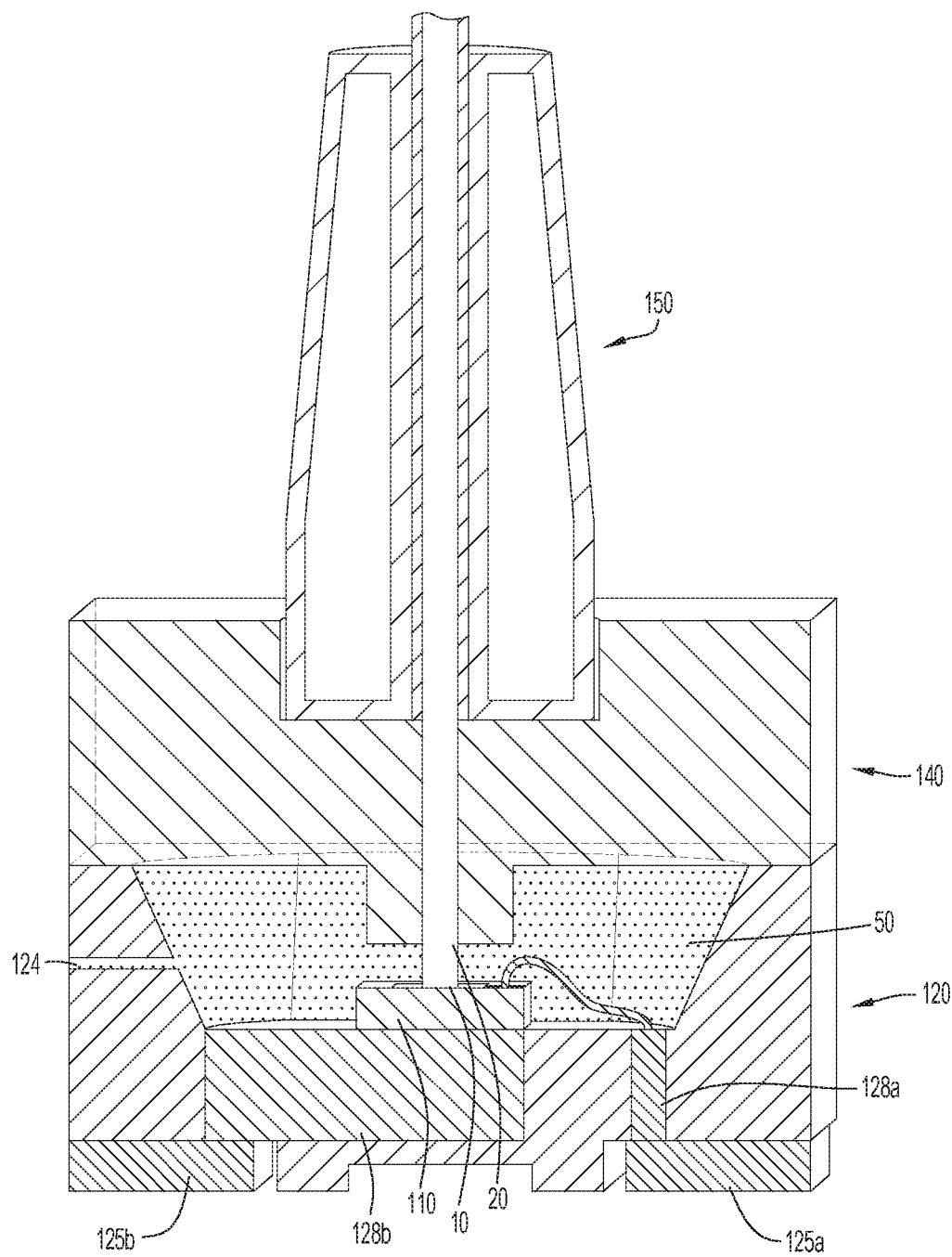
FIG. 4G shows the light module of FIG. 4C with an adhesive disposed inside the cavity of the support frame.
Figure 4H:
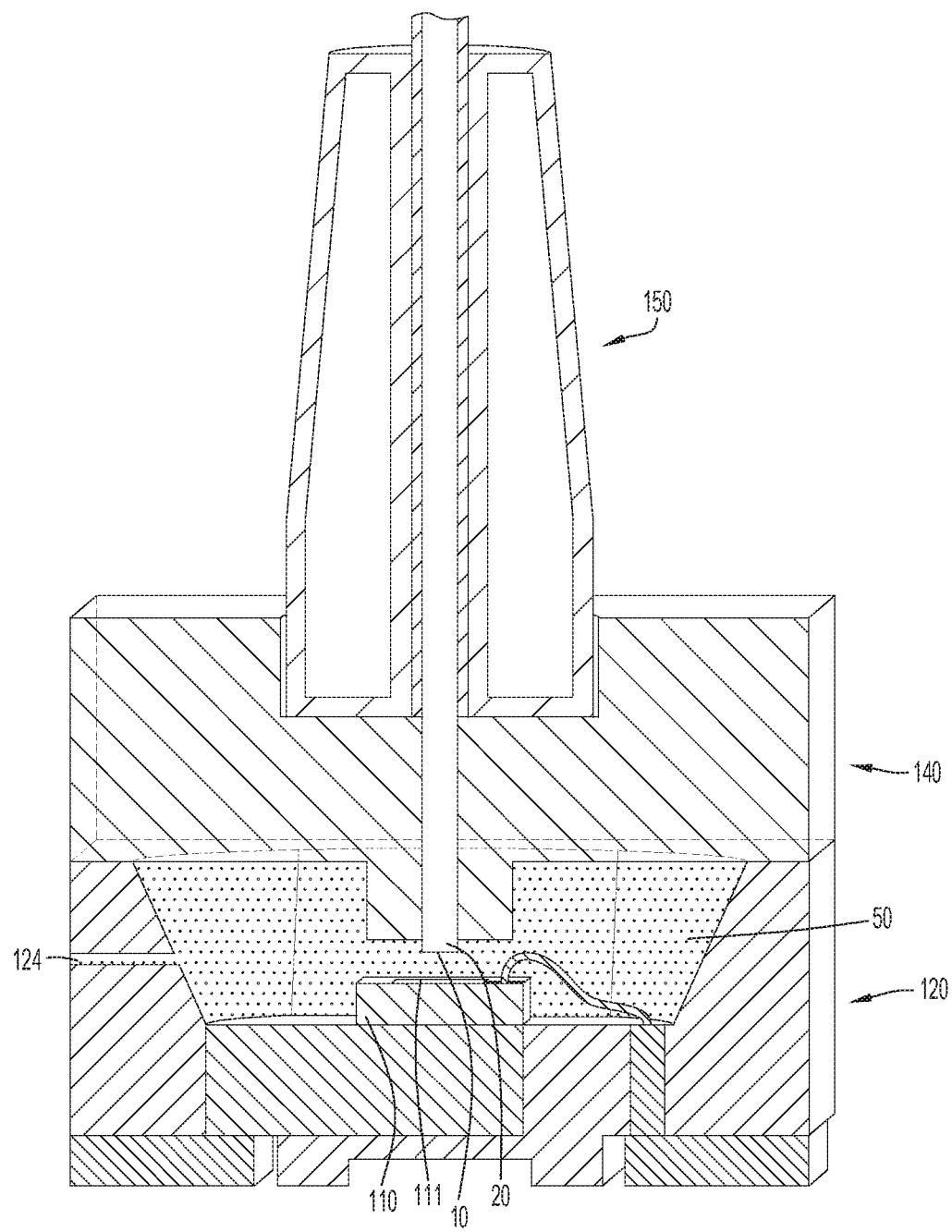
FIG. 4H shows the light module of FIG. 4D with an adhesive disposed inside the cavity of the support frame.

In implementations in which the light receiving end 10 of the optical fiber 12 is spaced a distance from the light emitting surface 114 of the LED 110 as in FIGS. 4F and 4H, the adhesive 50 may have a refractive index that more closely matches the refractive index of the material from which the core 20 is made as compared to of air to more effectively optically couple the core with the light emitting surface of the LED. According to other implementations an index matching gel instead of an adhesive is located inside the cavity 121 between the light receiving end 10 of the optical fiber 12 and the light emitting surface 114 of the LED 110. As with the adhesive 50, the gel may have a refractive index that more closely matches the refractive index of the material from which the core 20 is made as compared to the refractive index of air to more effectively optically couple the core with the light emitting surface of the LED.

Figure 4I:
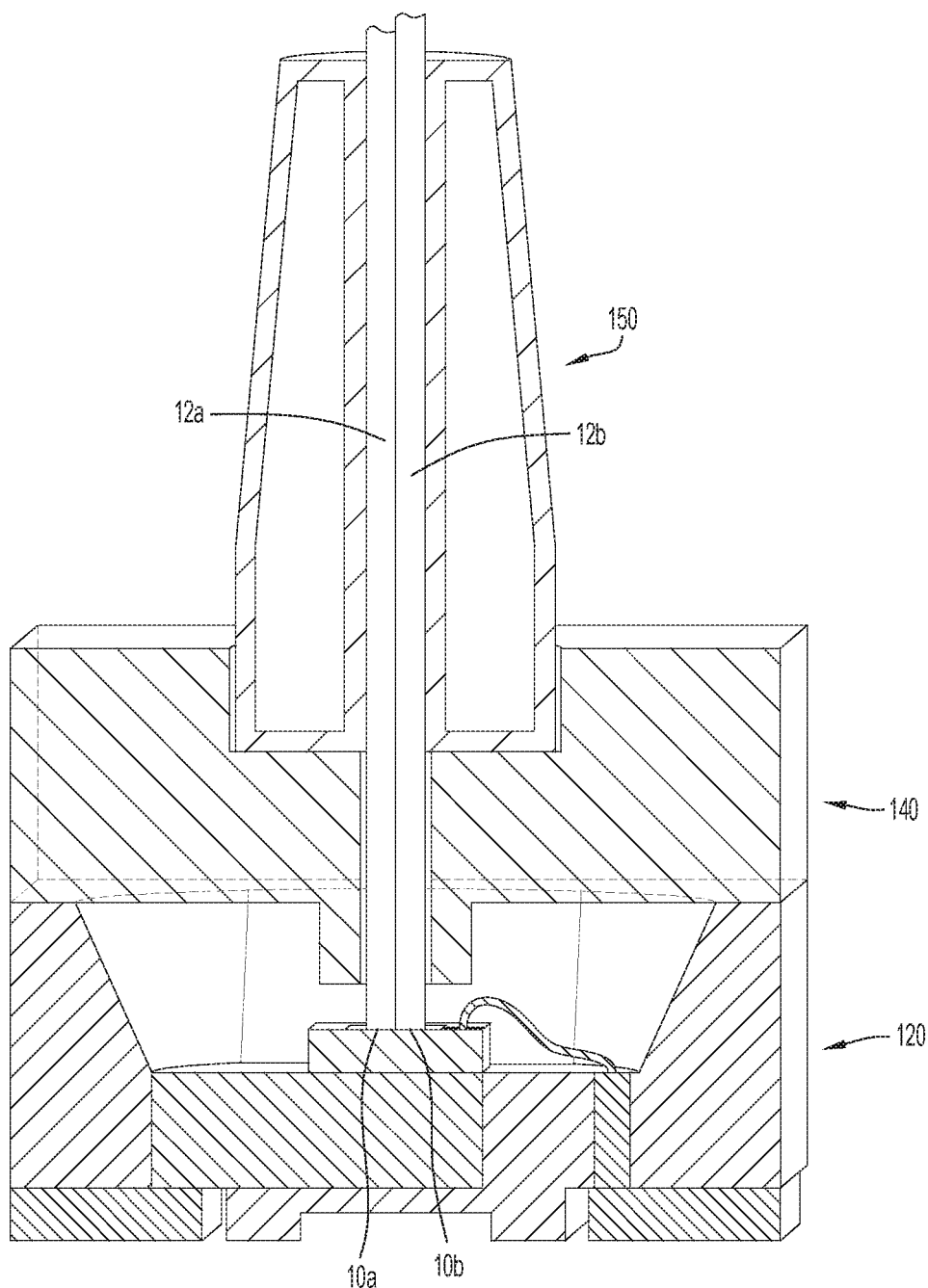
FIG. 4I shows a light module similar to that of FIG. 4A with there being multiple optical fibers butt-coupled to the light emitting diode.

According to other implementations the light module 100 includes a plurality of optical fibers whose light receiving ends are optically coupled to the light emitting surface 114 of the LED 110. FIG. 4I illustrates such an implementation that is similar to that of FIG. 4A in which the light receiving end 10a and 10b of optical fibers 12a and 12b are butt-coupled to the light emitting surface 114 of the LED 110. Although FIG. 4I shows the use of two optical fibers, it is appreciated that three, four or more optical fibers may be employed. This same concept of optically coupling multiple optical fibers to the light emitting surface of a single LED is also applicable to implementations like those of FIGS. 4B-4H. The bundling and optical coupling of two, three, four or more optical fibers to a single LED advantageously increases the optical coupling efficiency whereby a larger percentage of the light emitted by the light emitting diode is transmitted into the optical fibers and less light is lost to the surrounding environment.

FIGS. 2A, 2B, 4A and 6 illustrate a supporting frame 120 according to one implementation. The supporting frame includes a main body 129 on which two electrically conductive pads 125a and 125b are affixed. In the implementation shown in FIGS. 2A, 2B, 4A and 6, the electrically conductive pads 125a and 125b are arranged on the backside 123 of the supporting frame 120. According to other implementations the electrically conductive pads 125a and 125b may be respectively arranged on the side surfaces 126a and 126b of the supporting frame 120 and/or on the bottom side 127 of the supporting frame 120.

With continued reference to FIGS. 2A, 2B, 4A and 6, the anode 113 and cathode 115 of the LED 110 are respectively electrically coupled to the electrically conductive pads 125a and 125b through electrical conductor elements 128a and 128b that fully or at least partially reside within the main body 129 of the supporting frame 120. As shown in FIGS. 2B and 4A, according to one implementation the cathode 115 is surface mounted on electrical conductor element 128b and the anode 113 is electrically coupled to the electrical conductor element 128a by an electrically conductive wire 170. As will be discussed in more detail below, in use the electrically conductive pads 125a and 125b are respectively electrically coupled to a ground connection and to a voltage terminal of a power source.

According to some implementations electrically conductive pad 125a and electrical conductor element 128a comprise a unitary structure and/or electrically conductive pad 125b and electrical conductor element 128b comprise a unitary structure.

According to other implementations the anode 113 is coupled directly to electrically conductive pad 25 by an electrically conductive wire.

Figure 3:
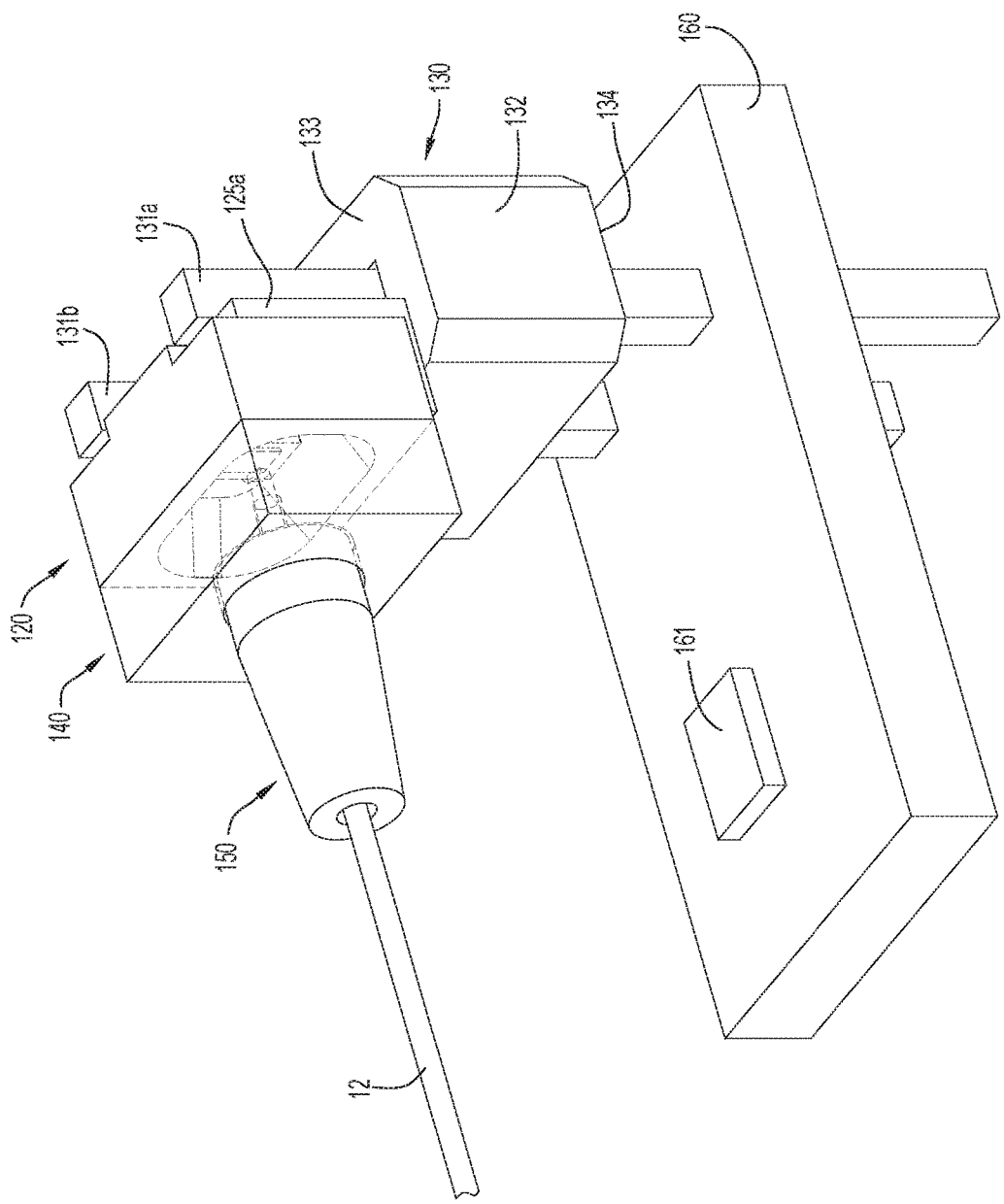
FIG. 3 shows the light module of FIGS. 2A and 2B physically and electrically connected to a printed circuit board.

One method of electrically coupling the anode 113 and cathode 115 of the LED 110 to a ground connection and a voltage terminal is through the use of a pin connector 130 comprising a set of pins 131a and 131b as shown in FIGS. 2A, 2B and 3. According one implementation a mid-portion of the pins 131a and 131b pass through a header 132 that comprises a top side 133 and a bottom side 134. The header 132 is made of an electrically non-conductive material that electrically isolates the electrically conducive pins 131a and 131b. According to one implementation the bottom surface 127 of the supporting frame 120 rests on the top side 133 of the header as shown in FIGS. 2B and 3 with the electrically conductive pads 125a and 125b respectively electrically coupled to a part of the pins 131a and 131b residing above the top side 133 of the header 132. According to one implementation a solder connection electrically couples the electrically conductive pads 125a and 125b to the pins 131a and 131b. According to some implementations each of the electrically conductive pads 125a and 125b comprises, at least in part, a solder that makes up the solder connection.

According to one implementation the bottom side 127 of the supporting frame 120 is fixed to the top side of the header 132 of the pin connector 130 by use of an adhesive. As such, the solder connections between electrically conductive pads 125a and 125b and pins 131a and 131b are less susceptible to breakage. According to other implementations, when the light module is fully assembled, the electrically conductive pads 125a and 125b of the supporting frame 120 are respectively fixed to pins 131a and 131b with a gap existing between the bottom side 127 of the supporting frame 120 and the top side 133 of the header 132.

As shown in FIG. 3, according to one implementation the part of pin 131a residing below the bottom side 134 of the header 132 is connected to a ground terminal or ground plane located inside or on a printed circuit board (PCB) 160 and the part of pin 131b residing below the bottom side 134 of the header 132 is connected to a voltage terminal residing in or on the PCB. The PCB 160 may comprise a driver 161 and other components that are used to regulate power to the LED 110. To put the scale of the light module in perspective, according to some implementations the PCB is about 3 to 4 mm$^2$.

Figure 7B:
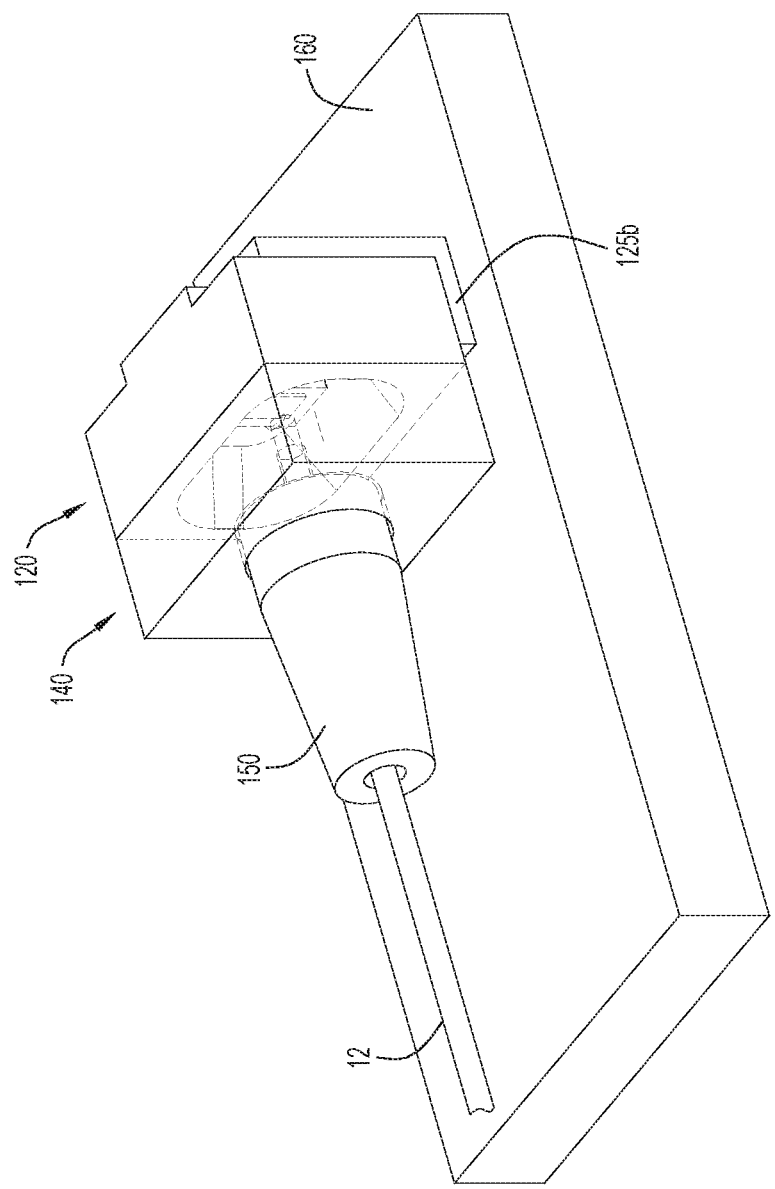
FIG. 7B is a perspective view of an assembly of FIG. 7A with the light module being surface mounted to the electrical contact pads of the printed circuit board.
Figure 8B:
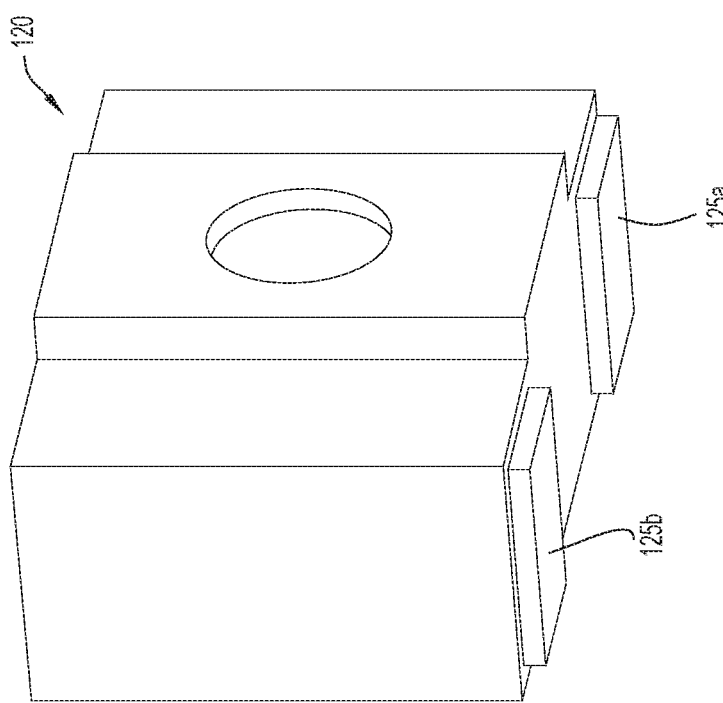
FIG. 8B is a perspective view showing a backside and bottom side of a light module according to another implementation.

According to other implementations the supporting frame 120 may be surface mounted on the PCB 160 as shown in FIG. 7B. According to one implementation, as shown in FIG. 7A, the PCB 160 comprises on a surface thereof a ground pad 161b and a voltage terminal pad 161a onto which the electrically conductive pads 125a and 125b are respectively bonded to establish a power connection to the LED 110 via the electrical conductor elements 128a and 128b. According to one implementation the electrically conductive pads 125a and 125b extend from the backside 123 to the bottom side 127 of the supporting frame 120 as shown in FIGS. 7A, 7B and 8A. Alternatively, the electrically conducive pads 125a and 125b may be provided only on the bottom side 127 of the supporting frame 120 as shown in FIG. 8B. According to such an implementation, the electrical conductor elements 128a and 128b are arranged to respectively electrically connect the cathode 115 and anode 113 of the LED 110 to the electrically conductive pads 125*a* and 125*b* located on the bottom side 127 of the supporting frame 120.

According to some implementations a lid 140 is situated on the front side 121 of the supporting frame 120 to protect the LED 110 from external elements and to also assist in aligning the light receiving end 10 of the optical fiber 12 with the light emitting surface 114 of the LED 110. According to some implementations, as shown in FIGS. 2A-C and 7B, the lid 140 includes first and second apertures 144 and 145 with the diameter of the first aperture being less than the diameter of the second aperture, and preferably no more than 20% greater, and more preferably no than 10% greater than the diameter of the portion of the optical fiber that resides therein. For example, according to one implementation the outer diameter of the optical fiber 12 is 0.9 millimeters and the inner diameter of the first aperture is between 1.0 and 1.1 millimeters. The backside 141 of the lid 140 may be attached to the front side 122 of the supporting housing 120 by the use of an adhesive. According to other implementations the lid 140 includes a through opening having a constant diameter that extends between its front side and backside. The lid is preferable made of a rigid plastic material that prevents a flexing of the lid during the process of assembling the light module. According to some implementations the length dimension of the first aperture or the through opening of constant diameter, whichever the case may be, is greater than the diameter dimension of that portion of the optical fiber residing therein. Such a feature assists in minimizing the risk of the optical fiber buckling during the light module assembling process.

A housing 150, in the form of a resilient strain relief member, encloses a proximal section of the optical fiber 12. The resilient strain relief housing 150 has a proximal end 151 of a first diameter and a distal end 152 of a second diameter that is less than the first diameter. The optical fiber 12 may be concentrically located and supported inside the housing 150 in a manner that relieves stress from the optical fiber or fibers to prevent breakage in the event of a pulling or bending of the optical fiber or fibers. According to some implementations the housing 150 includes an internal tube 155 that is configured to receive and circumferentially surround and engage the optical fiber 12 such that the optical fiber is concentrically disposed inside the housing. The housing 150 may be made of rubber or other resilient material suitable for serving the protective strain relief and housing functions described herein.

According to one implementation the housing 150 includes a cylindrical proximal section 153 and a conical-like distal section 154. According to some implementations the cylindrical proximal section 153 that resides inside the second aperture 145 of the lid 140 with its proximal-most end abutting an annular wall 143 (see FIG. 2C) located at the juncture of the first and second apertures 144 and 145. The proximal end segment 11 of the optical fiber 12 protrudes proximally from the strain relief housing 150 into and through the first aperture 144 of the lid 140. According to one implementation a slip fit exists between the inner wall of the first aperture 144 of the lid 140 and the outer wall of the proximal end section 11 of the optical fiber 12 so that the optical fiber 12 is capable of sliding within the first aperture 144 during an assembly of the light module 100. As discussed above, the proximal end section or segment 11 of the optical fiber 12 may or may not possess a cladding. Hence, the diameter of the outer wall of the proximal end section or segment of the optical fiber may be defined by either the cladding or the core of the optical fiber. In either case, according to some implementations the diameter of the first aperture 144 of the lid 140 is greater than the diameter of the outer wall of the optical fiber, but no greater than 20%, and preferably, no greater than 10%. Such an arrangement facilitates a proper alignment of the light receiving end 10 of the optical fiber 12 with the light emitting surface 114 of the LED 110. According to some implementations the proximal end of the resilient strain relief housing 150 is secured inside the second aperture 145 of the lid 140 by use of an adhesive.

According to some implementations, as shown in FIGS. 4A-I, the lid 140 includes a projection 147 through which the first aperture 144 passes, the projection 147 projecting from the backside 141 of the lid and into the cavity 121 of the support frame 120. An advantage of the projection 147 is that it positions the proximal opening of the first aperture 144 nearer to the LED 110 inside the supporting frame 120. This assists in aligning the light receiving end 10 of the optical fiber 12 with the LED 110 and reduces the length of the optical fiber that is unsupported, thus reducing the risk of breaking the optical fiber when it is butt-coupled to the LED.

According to some implementations to facilitate a proper alignment the backside 141 of the lid 140 with the front side 122 of the supporting frame 120, the width W and height H of the supporting frame 120 and the lid 140 are the same or substantially the same. In this manner, a flush alignment of the top, bottom and side external surfaces of the supporting frame 120 and lid 140 assures a proper alignment between them. To further assist in a proper alignment of the supporting frame 120 with the pin connector 130, the width of the header 132 may also be the same width as the supporting frame 120. A commonality of the width and/or height dimensions of the various parts of the light module 100 simplifies the manufacturing process by eliminating the need to employ the use of more complex alignment equipment.

Figure 11A:
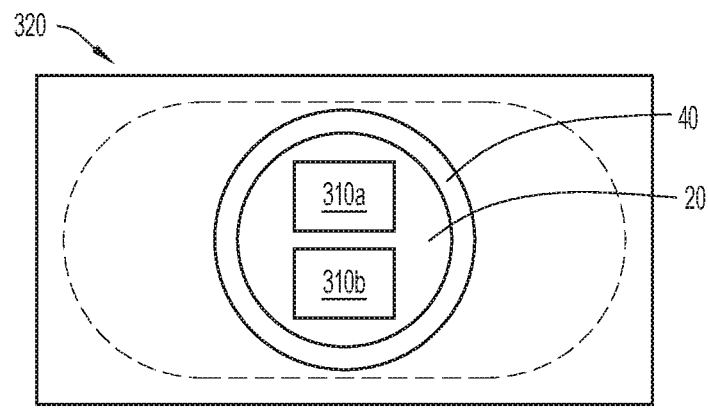
FIG. 11A shows a front face of a supporting frame of a light module that includes an optical fiber being optically coupled to two light emitting diodes.
Figure 11B:
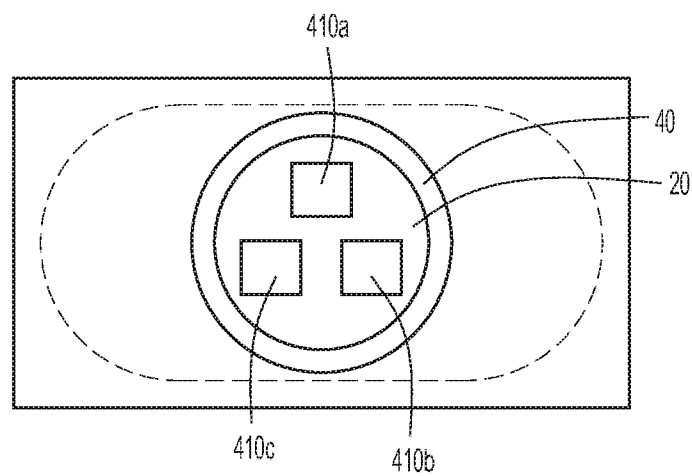
FIG. 11B shows a front face of a supporting frame of a light module that includes an optical fiber being optically coupled to three light emitting diodes.
Figure 12:
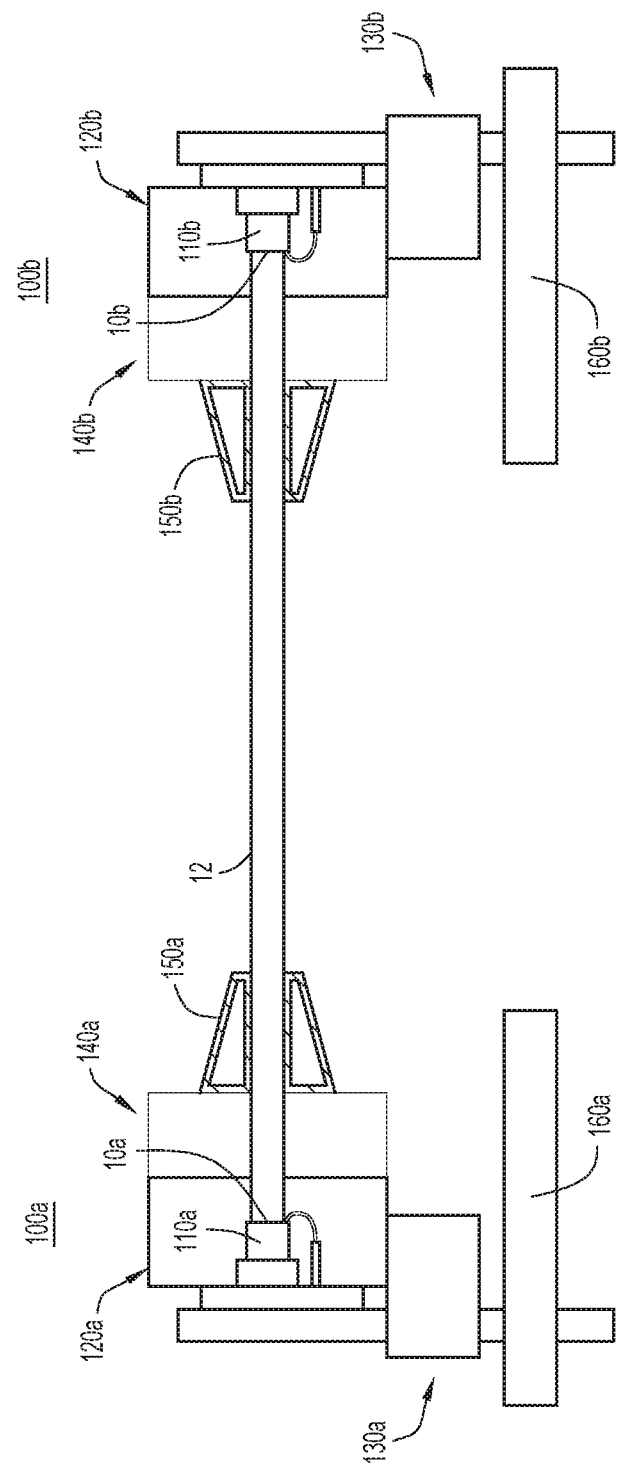
FIG. 12 illustrates an assembly that includes one or more optical fibers being coupled at opposite ends to one or more light emitting diodes.

As shown in FIG. 12, according to some implementations the light diffusing optical fiber 12 has first and second light receiving ends 10*a* and 10*b* that are respectively optically coupled to LED's 110*a* and 110*b* of light modules 100*a* and 100*b*. The construction of each of the modules 100*a* and 100*b* may be the same as that of the modules 100 described above. That is, each of modules 100*a* and 100*b* may include a supporting frame 120*a*, 120*b*, a lid 140*a*, 140*b* and a strain relief housing 150*a* and 150*b*. In the implementation of FIG. 12, the LEDS 110*a* and 110*b* are respectively coupled to power connections in PCBs 160*a* and 160*b*. However, according to other implementations the supporting frames 120*a* and 120*b* are surface mounted to ground and voltage terminals located on a top side of the respective PCBs 160*a* and 160*b* like that described above. It is also important to note that the light module system of FIG. 12 may comprise two or more optical fibers whose ends are optically coupled to LEDs 110*a* and 110*b*. Moreover, as will be discussed in more detail below, one or both of the supporting frames 120*a* and 120*b* may be substituted with the supporting frame 320 of FIG. 11A or the supporting frame 420 of FIG. 11B which each house multiple LEDs to which a light receiving end of the optical fiber is optically coupled.

According to some implementations the LEDs 110*a* and 110*b* are configured to emit visible light of the same color, and in some instances with the same or different intensities. An advantage of such implementations is that a more uniform distribution of light and/or light of greater intensity may be provided along the length of the light diffusing fiber, particularly in situations where the optical fiber 12 is long with the light modules 100*a* and 100*b* being spaced far apart from one another.

According to other implementations LED 110*a* is configured to emit visible light of a first color and LED 110*b* is configured to emit visible light of a second color different from the first color. Such implementations enable a dispersion of light along the length of the light diffusing optical fiber in multiple colors. For example, only LED 110*a* may be energized to cause light of the first color to be dispersed along the length of the light diffusing optical fiber, or only LED 110*b* may be energized to cause light of the second color to be dispersed along the length of the light diffusing optical fiber, or both of LEDs may be energized to cause a third color to be produced along at least a portion of the light diffusing optical fiber.

According to other implementations LED 110*a* is configured to emit visible light and LED 110*b* is configured to emit infrared light. Such implementations are useful in military and law enforcement applications wherein during daylight hours the clothing worn by or the equipment operated by military or law enforcement personnel may be identified by visible light dispersed along a length of a light diffusing optical fiber incorporated into such clothing or equipment and during nighttime hours the clothing or the equipment may be identified by infrared light.

According to other implementations LED 110*a* is configured to emit visible light and LED 110*b* is configured to emit disinfecting ultraviolet light. Such implementations are useful when it is desirable to at times illuminate an article for the purpose of readily identifying the article, and to at times. to provide light to disinfect the article. A handle on a piece of equipment in which at times visible light is used to more readily identify the handle and at other times disinfecting ultraviolet light is used to disinfect the handle. Such applications may include door handles of vehicles, buildings, medical equipment, food processing equipment, toilets, water facets, refrigerators etc. According to some implementations the visible light emitted by LED 110*a* and the disinfecting ultraviolet light emitted by LED 110*b* are concurrently emitted. For example, to warn a user not to touch an article that is being disinfected by ultraviolet light emitted by LED 110*b*, LED 110*a* may concurrently emit visible light to illuminate the article in the color red.

In the foregoing disclosure light modules possessing a single LED to which one or multiple optical fibers are optically coupled have been described. In the description that follows in regard to FIGS. 9A-D and 10A-C. 11A and 11B, light modules possessing two or more LEDs are provided.

Figure 9A:
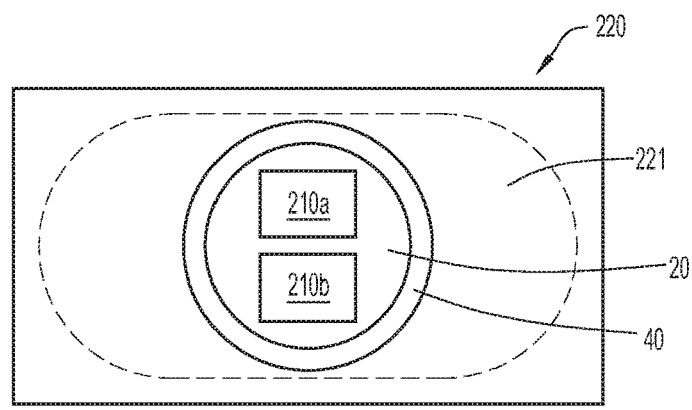
FIG. 9A is a front view of a frame of a light module wherein a single optical fiber is optically coupled to two light emitting diodes located inside a cavity of the frame.
Figure 9B:
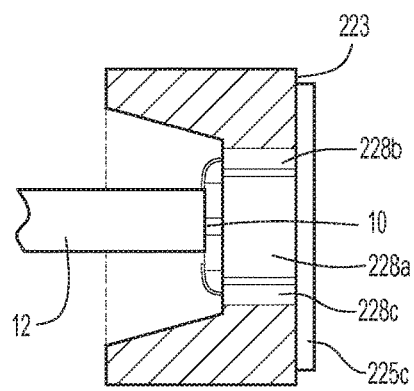
FIG. 9B shows a cross-section view of the supporting frame and light emitting diodes of FIG. 9A.
Figure 9C:
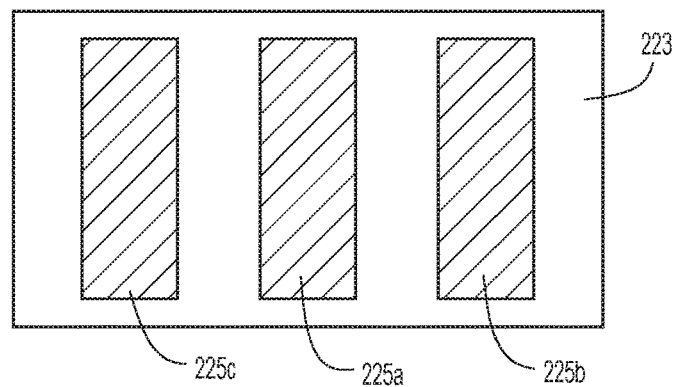
FIG. 9C shows the backside of the supporting frame shown in FIG. 9B.

FIGS. 9A-C illustrate another implementation wherein the light receiving end of the core 20 of a single optical fiber 12 is optically coupled to two light emitting diodes 210*a* and 210*b* that are housed inside a cavity 221 of a supporting frame 220. The light emitting diodes 210*a* and 210*b* may have a construction like that shown in FIGS. 5A-C with the anode and light emitting surface of each of the LEDs located on a front side of the LED and the cathode of the LEDs located on a backside of the LED. A difference in the LEDs of FIGS. 9A-C and light modules having three or more LEDs is that when multiple LEDs are employed, the cross-sectional areas of the light emitting surfaces of these LEDs are typically smaller. According to one implementation, as shown in FIG. 9B, the cathode on the backside of each of the LEDs is electrically coupled to a same electrical conductor element 225*a* and the anodes of LEDs 210*a* and 210*b* are respectively electrically coupled to separate electrical conductor elements 228*b* and 228*c*. In this manner the LEDs may be selectively energized to cause only one of the LEDs to illuminate or to cause both LEDs to illuminate at the same time.

FIG. 9C shows the backside 223 of the supporting frame 220 possessing electrically conductive pads 225*a-c* that are respectively electrically connected to electrical conductor elements 228-*c*. FIG. 9D shows an exploded perspective view of a light module 200 that includes a pin connector 230 comprising three pins 231*a*, 231*b* and 231*c* onto which the electrically conductive pads 225*a-c* are electrically coupled when the light module is fully assembled. In use, pin 231*a* is connected to a ground terminal and pins 231*b* and 231*c* are electrically coupled to separate voltage terminals or to a same voltage terminal. The light module 200 further includes the supporting frame 220 (in which the LEDS 210*a* and 210*b* are housed), a lid 240 and a resilient strain relief element 250 whose structure and function may be similar to those of the supporting frame 120, lid 140 and resilient strain relief element 250 as described above. The structure and function of the pin connector 230 may also be similar to the pin connector 130 described above.

Figure 10A:
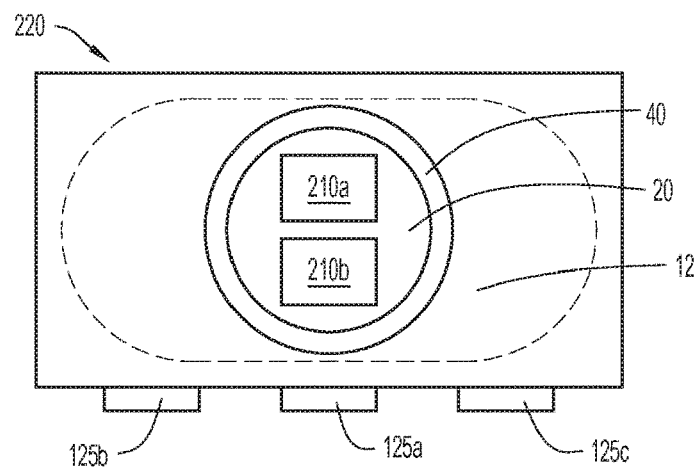
FIGS. 10A-C illustrates a supporting frame and light emitting diode configuration similar to that of FIGS. 9A-C equipped with electrically conductive pads for surface mounting the supporting frame to a printed circuit board.
Figure 10B:
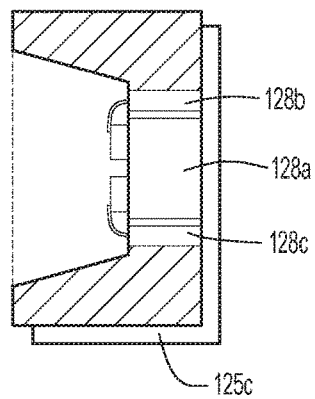
Figure 10C:
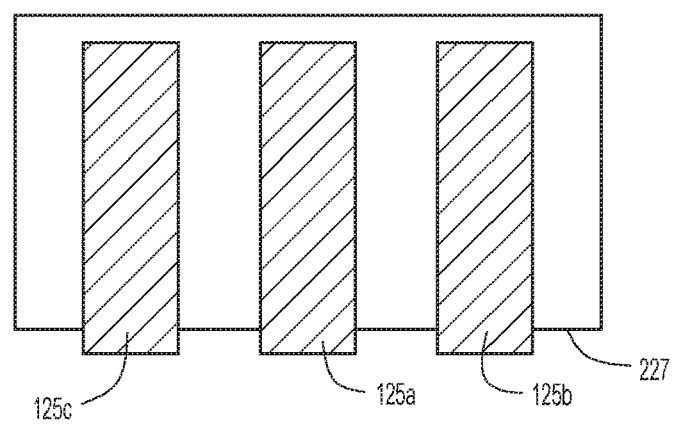

FIGS. 10A-C illustrate an implementation similar to that of FIGS. 9A-C in which a light receiving end of a single optical fiber 12 is optically coupled to an illuminating surface of multiple LEDs 210*a* and 210*b*. The implementation of FIGS. 10A-C differs from that of FIGS. 9A-C in that power is supplied to the anodes and cathodes of LEDs 210*a* and 210*b* via the use of electrically conductive pads 225*a-c* that extend to the bottom side 227 to accommodate a surface mounting of the supporting frame on a PCB in an electrically conductive way.

FIGS. 11A and 11B generically illustrate supporting frames 320 and 420 that respectively house two LEDs (310*a*, 310*b*) and three LEDs (410*a*, 410*b*, 410*c*). Examples of how the LEDs (310*a*, 310*b*, 410*a*, 410*b*, 410*c*) may be coupled to a power source are discussed above, but are in no way intended to limit the scope of the present disclosure. That is, the LEDs may be electrically coupled to one or more power sources with or absent the use of a PCB.

In the examples of FIG. 12 discussed above, implementations were disclosed that included coupling opposite end of an optical fiber to LEDs. However, in implementations involving the optical fiber and LED configurations of FIGS. 11A and 11B, multiple forms of light may be transmitted concurrently through an optical fiber from only one end of the optical fiber negating the need to implement the use of multiple light modules to effectuate a desired lighting scheme. Notwithstanding the foregoing, and as will be discussed in detail below, implementations by which opposite ends of an optical fiber are each optically coupled to multiple LEDs are also contemplated.

According to one implementation, as shown in FIG. 11A, a light receiving end of a single optical fiber 12 may be optically coupled to two LEDs 310*a* and 310*b* to facilitate a delivery of different light forms into the optical fiber. For example, according to some implementations light is transmitted into the light receiving end of the optical fiber from LEDs 310*a* and 310*a* one at a time, and according to other implementations light is concurrently transmitted from both LEDs 310*a* and 310*b* into the light receiving end of the optical fiber.

According to one implementation the optical fiber may be incorporated into an object in need of disinfection by use of ultraviolet or blue light, each of which can be hazardous to a user of the object. In such an implementation LED 310*a* may emit ultraviolet or blue light to kill bacteria, viruses and other infectious matter residing in or on the object and LED 310*b* may emit visible light to indicate a status of the object. For example, when no disinfecting light is being delivered to the object, LED 310*b* may transmit green light to indicate the object is disinfected and ready to use.

According to another implementation LED 310*a* may emit ultraviolet or blue light to kill bacteria, viruses and other infectious matter residing in or on the object and at the same time LED 310*b* may emit visible red light to communicate to a user a danger in handling the object during the disinfecting process. According to one implementation LED 310*b* is an RGB LED capable of emitting different colors of visible light. According to such an implementation the LED 310*b* may emit visible red light when LED 310*a* is emitting disinfecting light and visible green light when LED 310*a* is shut off. An implementation according to FIG. 11B may also be employed for the same purpose in that LED 410*a* may be configured to emit disinfecting light, LED 410*b* may be configured to emir visible red light when LED 410*a* is energized, and LED 410C may be configured to emit visible green light when LED 410*a* is de-energized.

Turning again to FIG. 11A, according to some implementations LED 310*a* may be configured to emit visible light and LED 310*b* may be configured to emit infrared light. Such implementations are useful in military and law enforcement applications wherein during daylight hours the clothing worn by or the equipment operated by military or law enforcement personnel may be identified by visible light emitted along a length of a light diffusing optical fiber incorporated into such clothing or equipment and during nighttime hours the clothing or the equipment may be identified by infrared light.

FIG. 13A illustrates an exemplary medical apparatus 500 that includes a control panel with keys 501, switches 502 and a display 503. The apparatus includes an internal chamber in which infectious or bacterial matter may be deposited from time to time for analysis purposes. In the example of FIG. 13A, the apparatus includes a lid 505 that is moveable between a closed position in which the chamber is inaccessible and an open position in which the chamber is accessible. The lid 505 includes a handle 507 that may be gripped by a user of the apparatus to assist in opening and closing of the lid.

Figure 13B:
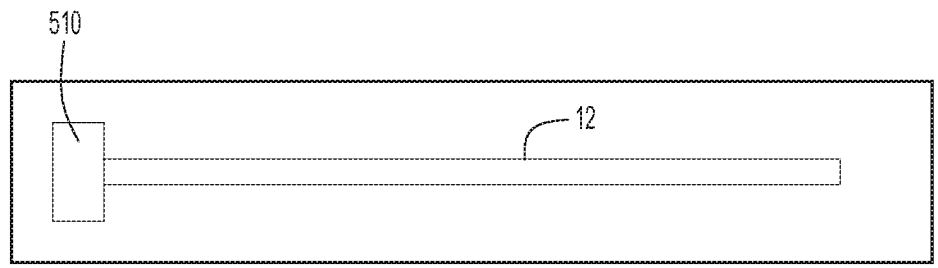
FIGS. 13B and 13C show examples of incorporating one or more light modules inside the handle of the medical apparatus shown in FIG. 13A.

FIG. 13B illustrates the handle 507 according to one implementation in which a single light diffusing optical fiber 12 is disposed and forms a part of a light module generically shown as element 510 in the figure. The light module 510 may comprise supporting frame, LED and optical fiber configurations description above and the description that follows. For example, according to some implementations the light module 510 may comprise an arrangement like those shown in FIGS. 2A-4G. In implementations wherein a light module includes multiple LEDs like those shown in FIG. 11A, LED 310*a* may emit ultraviolet or blue light to kill bacteria, viruses and other infectious matter residing in or on the handle 507 and LED 310*b* may emit visible light to indicate a status of the apparatus 500. For example, when no disinfecting light is being delivered to the handle 507 through LED 310*a*, LED 310*b* may transmit green light to indicate the object is disinfected and ready to use.

According to another implementation LED 310*a* may emit ultraviolet or blue light to kill bacteria, viruses and other infectious matter residing in or on the handle and at the same time LED 310*b* may emit visible red light to communicate to a user a danger in touching the handle during the disinfecting process. According to one implementation LED 310*b* is an RGB LED capable of emitting different colors of visible light. According to such an implementation the LED 310*b* may emit visible red light when LED 310*a* is emitting disinfecting light and visible green light when LED 310*a* is shut off. An implementation according to FIG. 11B may also be employed for the same purpose in that LED 410*a* may be configured to emit disinfecting light, LED 410*b* may be configured to emir visible red light when LED 410*a* is energized, and LED 410C may be configured to emit visible green light when LED 410*a* is de-energized.

Figure 13C:
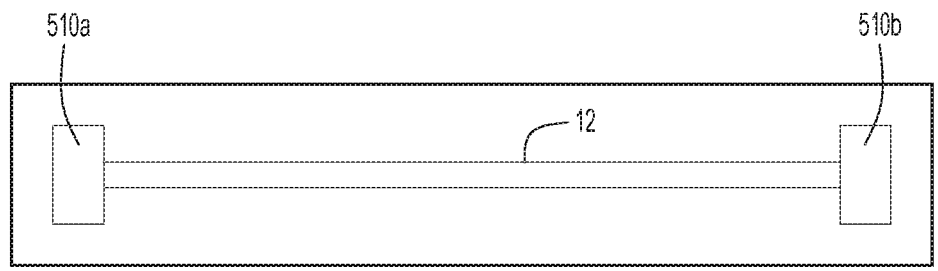

FIG. 13C illustrates an implementation in which first and second ends of a light diffusing optical fiber 12 are optically coupled to separate light modules generically shown as elements 510*a* and 510*b*. According to one implementation each of the first end and second end of the optical fiber 12 may be optically coupled to a single LED in a manner consistent with the implementation of FIG. 12 described above.

According to another implementation the first end of the optical fiber 12 may be optically coupled to a single LED like those shown in FIGS. 2A-4H and the second end of the optical fiber 12 is optically coupled to multiple LEDs in a manner like that shown in FIGS. 11A and 11B. According to one such implementation the first end 10*a* of the optical fiber 12 is optically coupled to an LED that is configured to emit bacterial disinfecting light, such as ultraviolet light or blue light and the second end 10*b* of the optical fiber 12 is optically coupled to a first LED that is also configured to emit bacterial disinfecting light and to a second LED that is configured to emit visible light. According to such an implementation the LEDs configured to emit bacterial disinfecting light may be energized concurrently to transmit bacterial disinfecting light into each end of the optical fiber for the purpose of optimizing the disinfecting process. The optimization may include provided an enhanced dosage of disinfecting light not achievable by a single LED and/or a more uniform distribution of disinfecting light along the length of the optical fiber. The LED that emits visible light may, for example, be configured to emit red light during the disinfecting process to warn a user against touching the handle 507.

In accordance with some implementations disclosed herein blue light at a wavelength of between 380-495 nm is employed to kill the unwanted bacteria. According to other implementations, ultraviolet light at a wavelength of 100-400 nm is employed to kill unwanted bacteria.

According to another implementation each of the first and second ends 10*a* and 10*b* of the optical fiber 12 may be optically coupled to multiple LEDs in a manner like that shown in FIGS. 11A and 11B. According to one such implementation the first end 10*a* of the optical fiber 12 is optically coupled to a first LED that is configured to emit bacterial disinfecting light and a second LED that emits visible light of a first color. The second end 10*b* of the optical fiber 12 is in turn optically coupled to a third LED that is also configured to emit bacterial disinfecting light and to a fourth LED that is configured to emit visible light of a second color different than the first color. According to such an implementation the first and third LEDs may be energized concurrently to transmit bacterial disinfecting light into each end of the optical fiber for the purpose of optimizing the disinfecting process. The second LED may be configured to emit red light during the disinfecting process to warn a user against touching the handle 507. The fourth LED may be configured to emit green light when the first and third LEDs are de-energized.

Figure 14A:
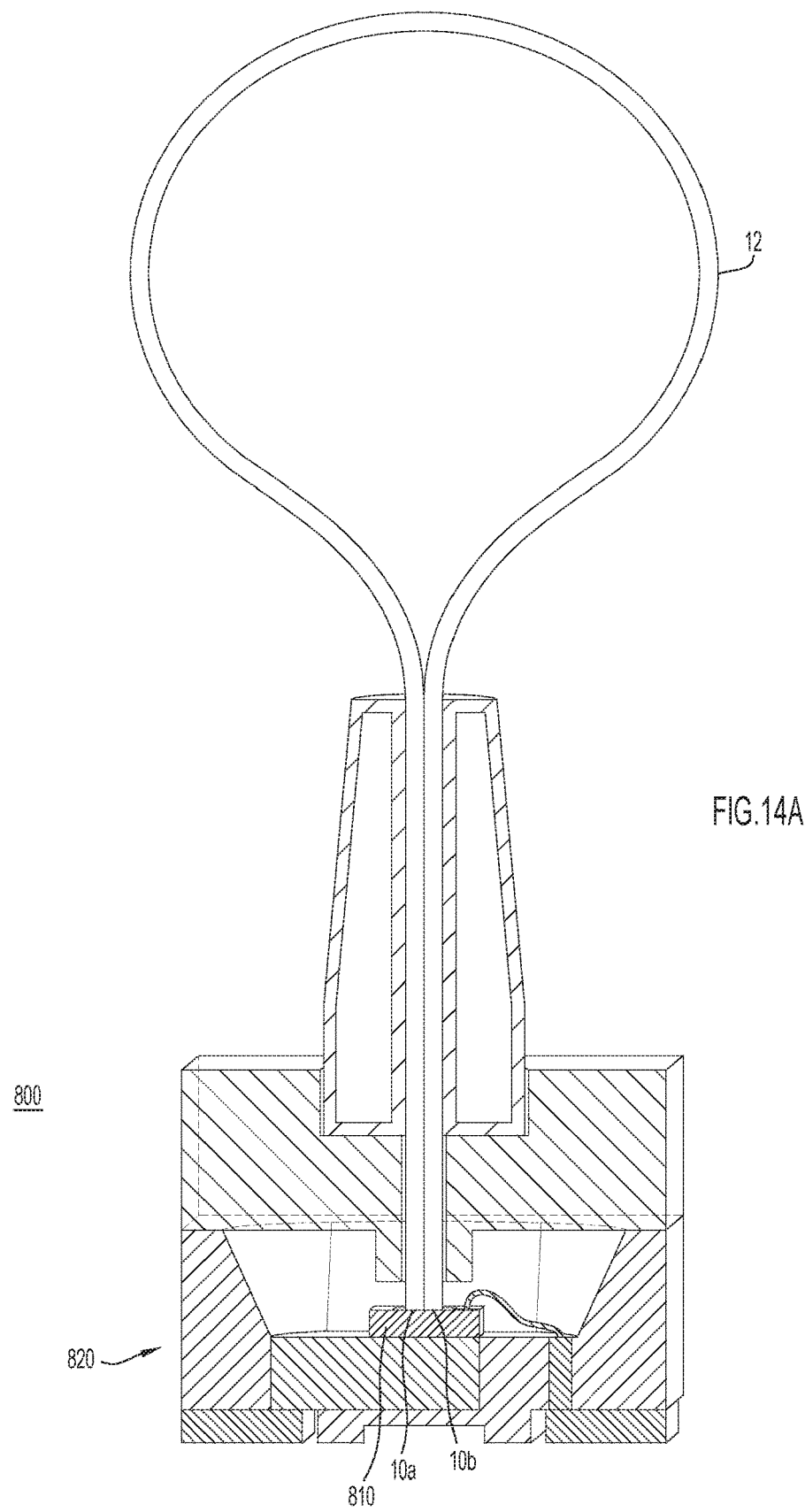
FIG. 14A illustrates a light module wherein the opposite ends of an optical fiber are optically coupled to the same light emitting diode.

FIG. 14A illustrates a light module 800 according to another implementation in which the first and second ends 10*a*, 10*b* of the optical fiber 12 are optically coupled to one or more LEDs located in a common supporting frame 820. The supporting frame/LED configurations of FIGS. 2A, 11A and 11B may be employed in such implementations. Other supporting frame/LED configurations are also contemplated.

In the example of FIG. 14A each end 10a, 10b of the optical fiber 12 is optically coupled to a single LED 810. The LED 810 may be configured to emit visible light, ultraviolet light or infrared light. Regardless of the type of light being emitted by the LED 810, by virtue of each end of the optical fiber being coupled to the LED 810 a more uniform distribution of light along the length of the fiber may be achieved, particularly in situations in which the optical fiber has a long length.

Figure 14B:
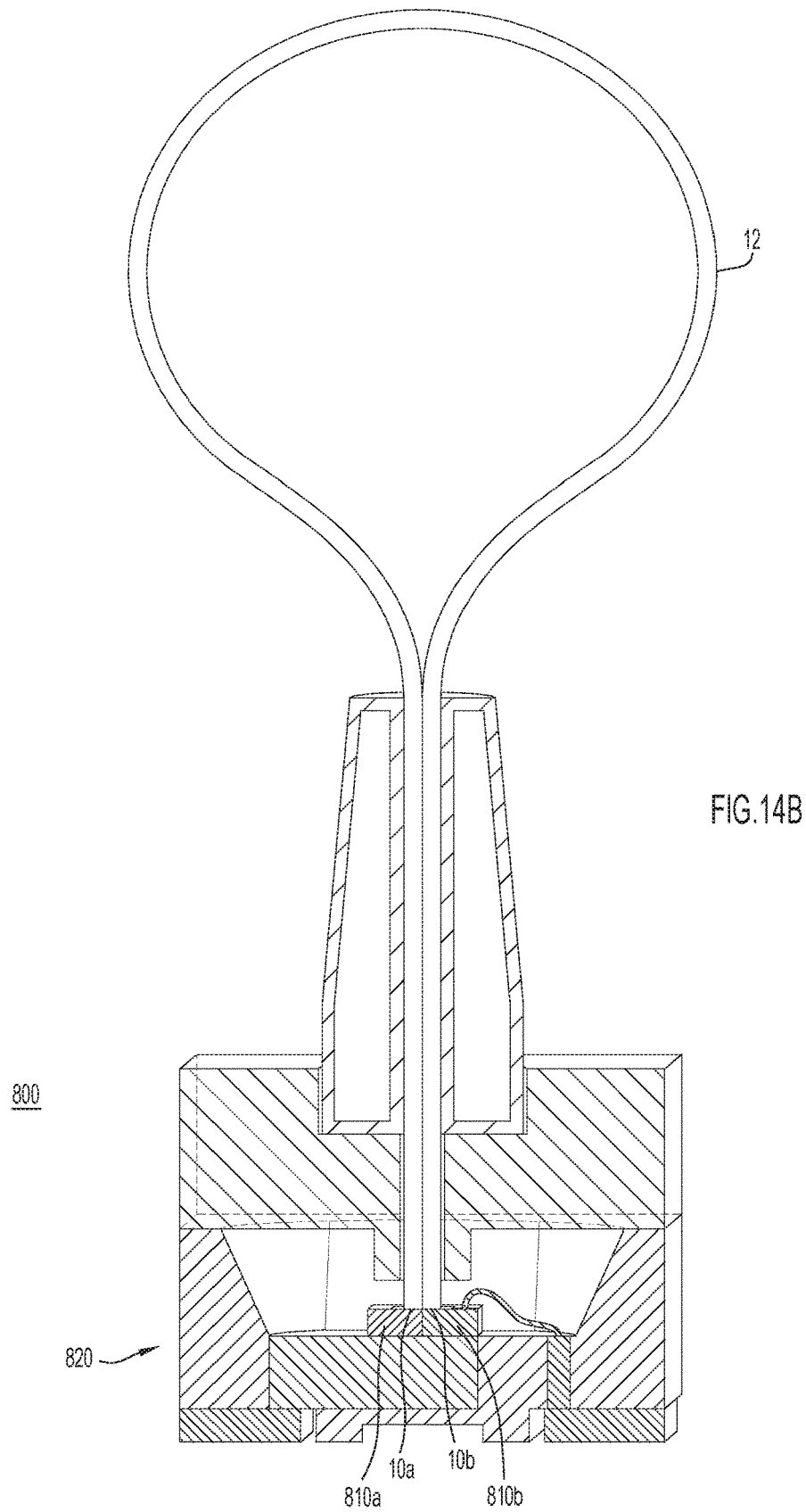
FIG. 14B illustrates a light module comprising first and second light emitting diodes located in a common supporting frame, and with the opposite first and second ends of an optical fiber being respectively optically coupled to the first and second light emitting diodes.

In the example of FIG. 14B the first end 10a of the optical fiber 12 is optically coupled to a first LED 810a and the second end 10b of the optical fiber 12 is optically coupled to a second LED 810b. Each of LEDs 810a and 810b may be configured to emit visible light, ultraviolet light or infrared light. According to some implementations LED 810a and LED 810b are independently controlled so that they may be separately energized and de-energized at different times. According to other implementations LED 810a and LED 810b are commonly controlled so that each is energized and de-energized at the same time. According to one implementation each of LEDs 810a and 810b is configured to emit disinfecting ultraviolet light. According to another implementation LED 810a is configured to emit disinfecting ultraviolet light and LED 810b is configured to emit visible light (e.g. red light). According to another implementation LED 810a is configured to emit infrared light and LED 810b is configured to emit visible light.

Figure 15A:
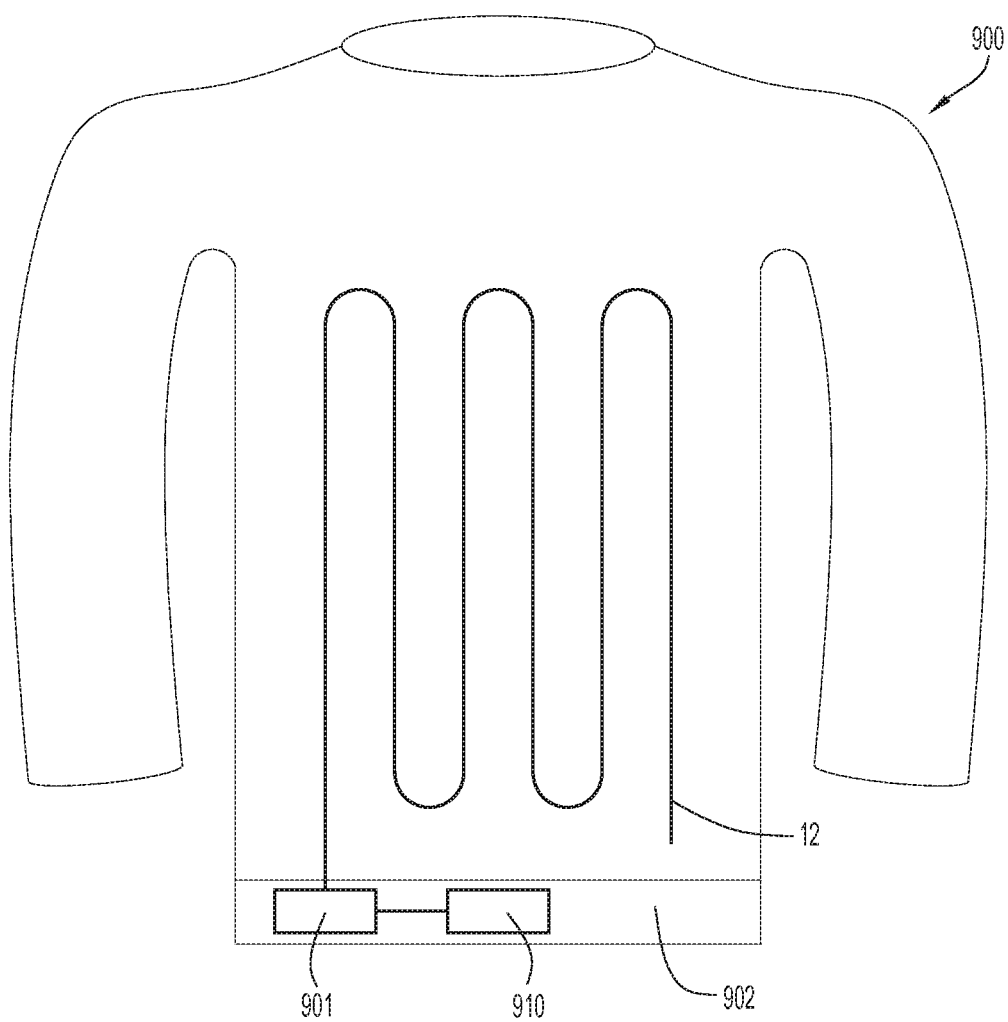
FIG. 15A-B shows examples of a garment incorporating therein light modules.

Turning again to FIG. 11A, according to some implementations LED 310a may be configured to emit visible light and LED 310b may be configured to emit infrared light. Such implementations are useful in military and law enforcement applications where during daylight hours the clothing worn by or the equipment operated by military or law enforcement personnel may be identified by visible light emitted along a length of a light diffusing optical fiber incorporated into such clothing or equipment and during nighttime hours the clothing or the equipment may be identified by infrared light. In the example of FIG. 15A an upper garment 900 is shown having incorporated therein a light module shown generically as element 901. Extending from the light module is a light diffusing optical fiber 12 that is attached to or otherwise woven into the garment. According to one implementation, as shown in FIG. 15A, the light module 901 resides in a waist band 902 of the garment. However, due to its small size (occupying a space as small as 8 to 64 mm$^3$ according to some implementations) the light module 901 is capable of residing in almost any part of the garment.

As discussed above, according to one implementation the light module 901 includes a supporting frame, lid and LED located inside the supporting frame with a configuration like that of FIG. 11A wherein a light receiving end of an optical fiber 12 is optically coupled to both LED 110a and LED 110b. Power to the light module 901 is provided by a battery 910 that also may be located in the waist band 902 of the garment 900.

Figure 19A:
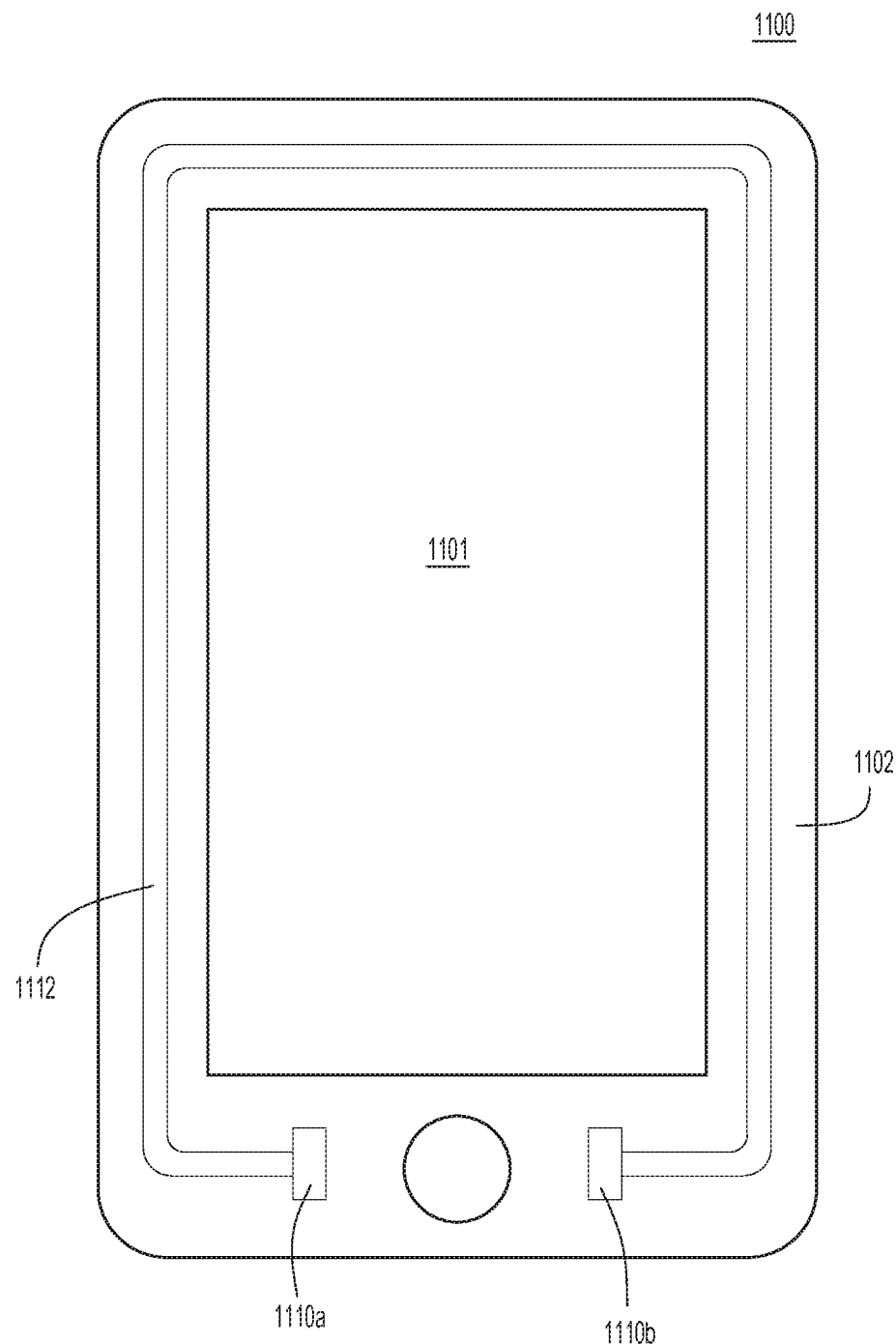
FIGS. 19A and 19B show a smart device, such as a portable phone or pad device having embedded in a casing or a display glass cover one or more light diffusing optical fibers coupled to one or more light emitting diodes located inside the device.
Figure 19B:
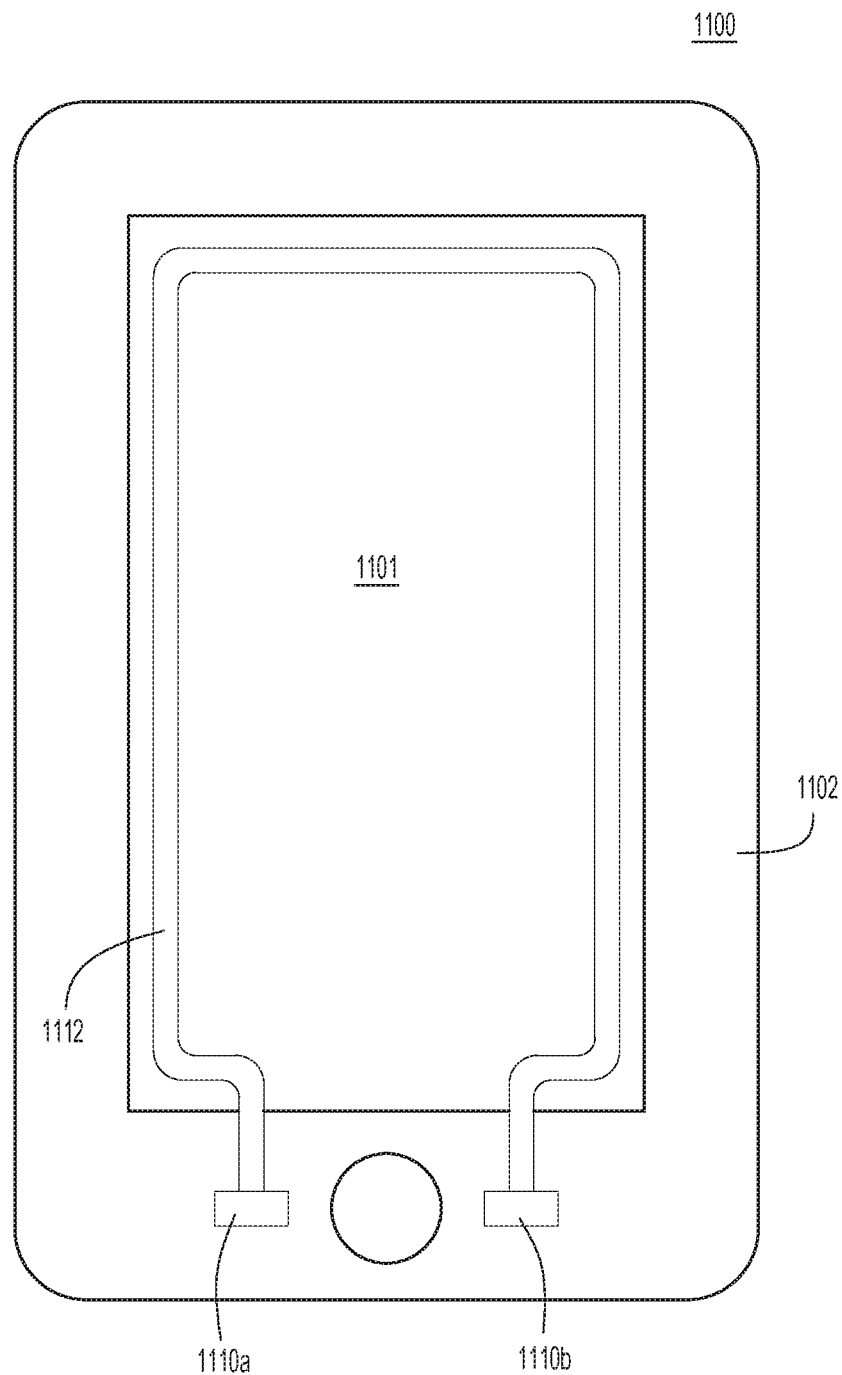
Figure 19C:
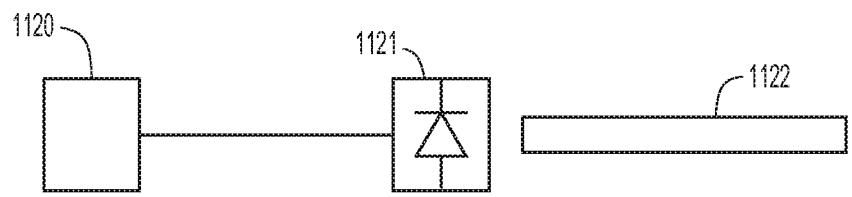
FIG. 19C schematically illustrates a control circuit for energizing and de-energizing the one or more light modules located in the smart devices of FIGS. 19A and 19B.

According to some implementations a control circuit like that shown in FIG. 19C may be employed to control the energizing and de-energizing of the LED(s). That is, a button or touch sensor may be intergraded into the garment for controlling the turning on and turning off of the LED(s). According to other implementations the control circuit is comprised in a device external to the garment that is configured to control the energizing and de-energizing of the LED(s) via a wireless connection such as Bluetooth. According to such implementations, a PCB to which the light module is electrically coupled comprises a receiver that is configured to receive signals from a transmitter associated with a button or touch sensor of the external device.

Figure 15B:
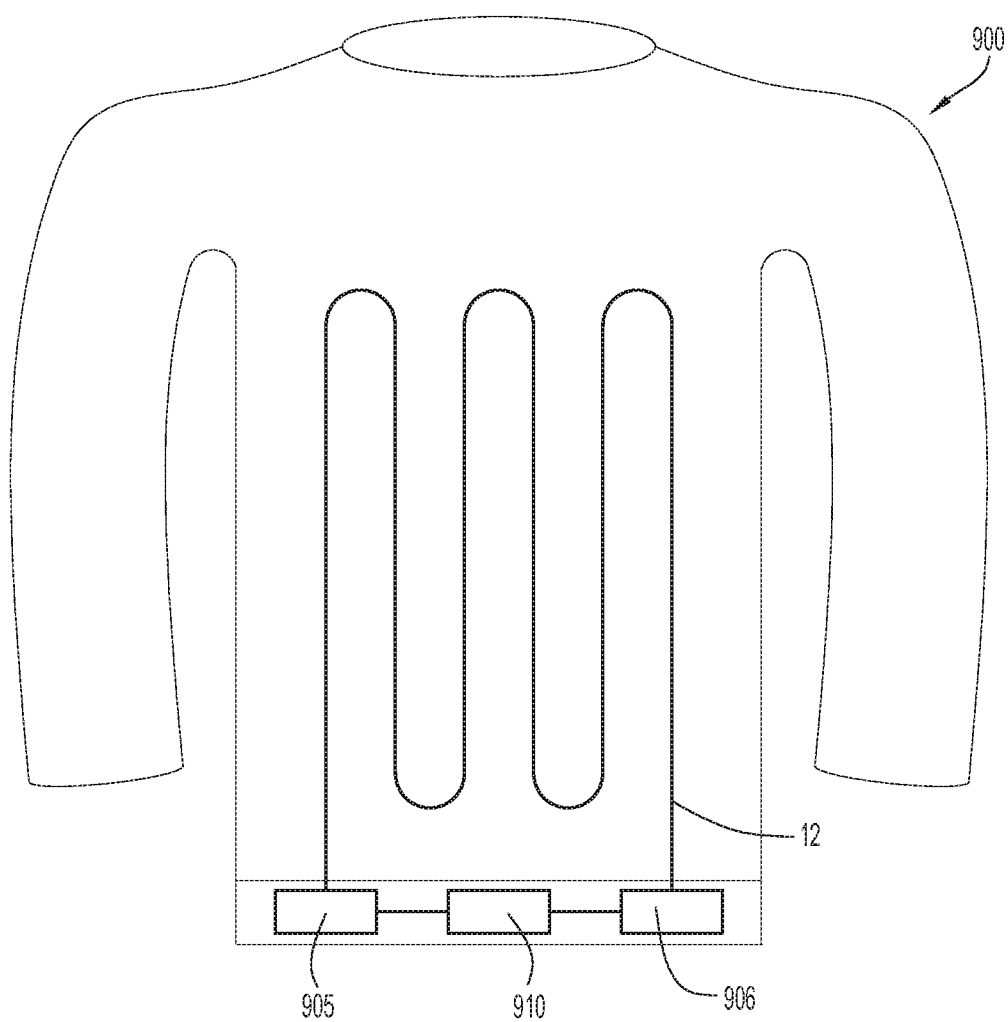

FIG. 15B illustrates another implementation in which the opposite ends of the light diffusing optical fiber 12 are separately integrated into first and second modules 905 and 906. According to some implementations configurations like those discussed above in conjunction with FIG. 12 may be employed to illuminate the garment 900 in accordance with different lighting schemes for entertainment purposes or military/law enforcement applications. It is appreciated that the light modules disclosed and contemplated herein may be incorporated into any of a number of other garments, such as hats, helmets, pants, gloves, etc.

In the foregoing exemplary implementations light emitting diodes, the diodes were disclosed as having an anode and cathode respectively located on the front side and backside of the device. It is appreciated that the other types of LEDs may also be used. For example, according to some implementations the anode and cathode may both reside on either the backside or the front side of the LED. When located on the backside of the LED, the anode and cathode may be respectively surface mounted in an electrically conductive way to the electrical conductor elements 128a and 128b. When located on the front side of the LED, the anode and cathode may respectively be electrically coupled to the electrical conductor elements 128a and 128b by electrically conductive wires, or may respectively be directly electrically coupled to the electrically conductive pads 125a and 128b by electrically conductive wires.

Figure 16:
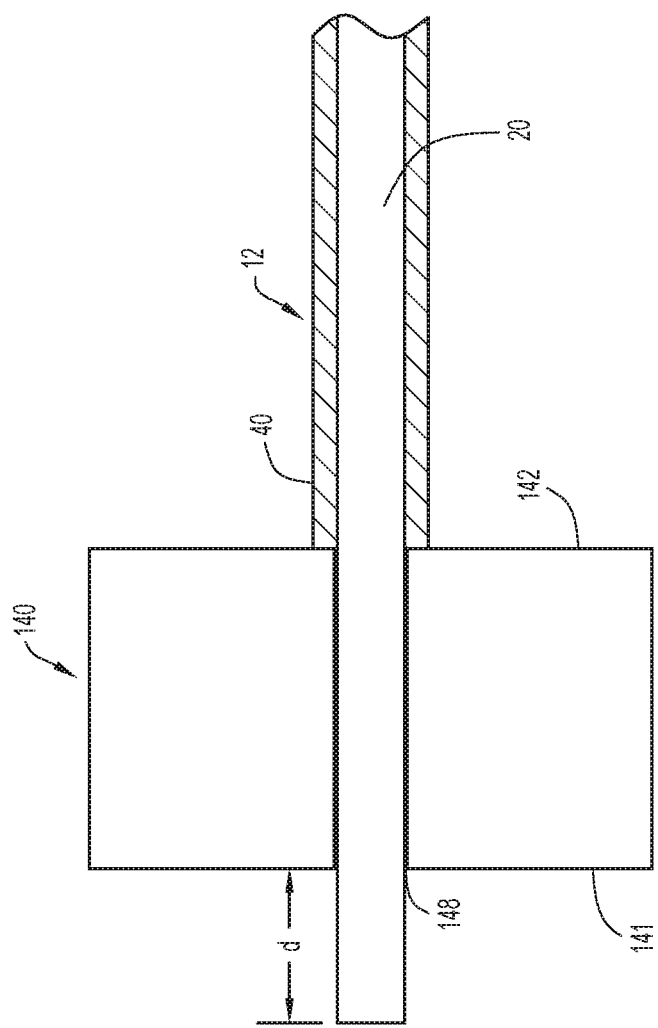
FIG. 16 is a side cross-section view of a lid and optical fiber configuration according to one implementation.

As discussed above, according to some implementations the lid 140 has a through opening that extends between and through its front side 142 and backside 141. According to some implementations, as shown in FIG. 16, the optical fiber has a first portion and a second portion distal to the second portion, the first portion extending through the through opening of the lid and being devoid of a cladding. The second portion includes a cladding and has an outer diameter that is greater than an outer diameter of the first portion of the optical fiber. The second end portion does not reside in the through opening 148 of the lid with the cladding of the second portion of the optical fiber abutting the front side of the lid. Such implementations allows the cladding to be removed from around the core of the optical fiber up to a precise distant distal from the light receiving end of the core. The abutment of the cladding with the front side of the lid provides a consistent and accurate axial placement of the optical fiber with respect to the light emitting surface of the LED during the light module assembling process. That is, the distance d by which the core of the optical fiber extends proximally from the backside 141 of the lid 140 can be more precisely controlled.

Figure 17:
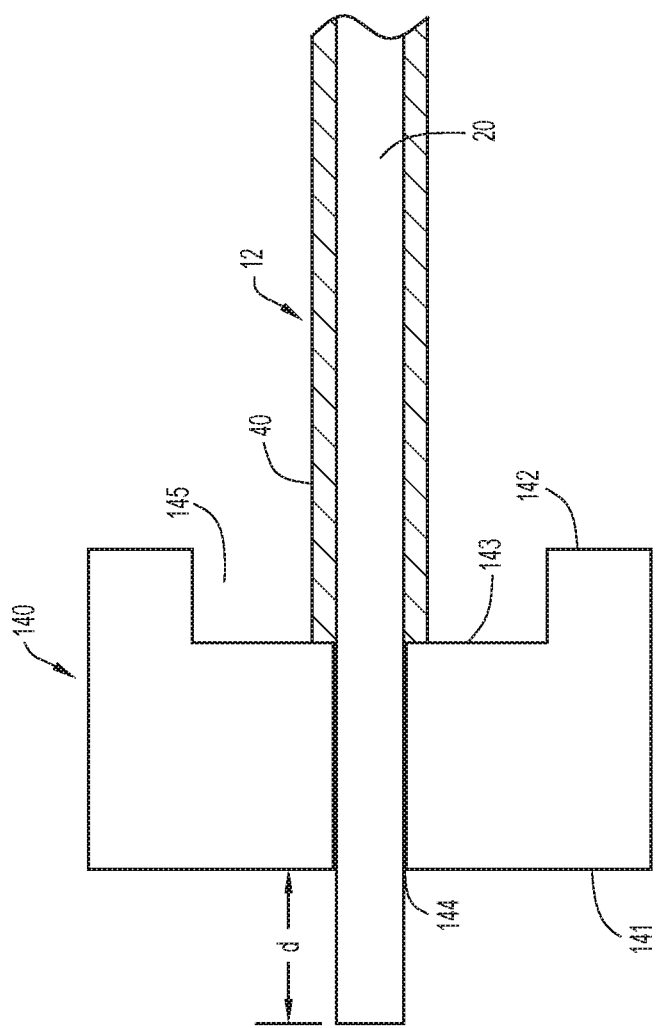
FIG. 17 is a side cross-section view of a lid and optical fiber configuration according to one implementation.

Also as discussed above, according to some implementations the lid 140 has a through opening that extends between and through its front side 142 and backside 141 with the through opening of the lid 140 comprising a first bore 144 that opens to the backside 141 of the lid and a second bore 145 that opens to the front side of the lid. The first bore has a first diameter and the second bore has a second diameter greater than the first diameter to create an annular surface 143 at the juncture of the first and second bores (see FIG. 2C). According to some implementations, as shown in FIG. 17, the optical fiber has a first portion and a second portion distal to the second portion. The first portion extends through the first bore of the lid and is devoid of a cladding. The second portion of the optical fiber includes a cladding and has an outer diameter that is greater than an outer diameter of the first portion of the optical fiber. A proximal end of the second end portion residing in the first bore of the lid with the cladding of the second portion abutting the annular surface 143 of the through opening. Such implementations allows the cladding to be removed from around the core of the optical fiber up to a precise distant distal from the light receiving end of the core. The abutment of the cladding with the annular wall 143 inside the through opening of the lid 140 provides a consistent and accurate axial placement of the optical fiber with respect to the light emitting surface of the LED during the light module assembling process. That is, the distance d by which the core of the optical fiber extends proximally from the backside 141 of the lid 140 can be more precisely controlled.

FIG. 19A shows a smart device 1100 (e.g. an iPhone®, iPad®, etc.) in which there is embedded one or more light diffusing optical fibers 1112. The smart device 1100 includes a display 1101 that is covered by a protective glass and is circumscribed by a casing 1102. In the implementation of FIG. 19A, the casing 1102 may be made of a light transparent or opaque material and has embedded therein a light diffusing optical fiber 1112 that is coupled at opposite ends to LEDs 1110a and 1110b. According to other implementations the light diffusing optical fiber 1112 is optically coupled at only one end to a single LED or to multiple LEDs.

In the implementation of FIG. 19A a single light diffusing optical fiber 1112 is coupled at a first end to LED 1110a and at a second end to LED 1110b. According to one implementation each of LEDs 1110a and 1110b emits visible light of the same color. The LEDs may be connected to a control circuit inside the device that causes the LEDs to be energized upon the occurrence of certain events. For example, the LEDs may be caused to illuminate upon a signal being sent to the control unit indicative of there being an incoming phone call, text message, etc. In the case of an incoming phone call or text, the control circuit may be configured to energize the LEDs according to different lighting sequences. For example, upon the occurrence of an incoming phone call the control circuit may be configured to cause each of the LEDs 1110a and 1110b to constantly illuminate, and upon the occurrence of an incoming text the control circuit may be configured to cause the LEDs 1110a and 1110b to intermittently energize to produce flashing light. As mentioned above, according to one implementation the LEDs 1110a and 1110b may be positioned adjacent one another with only one end of the optical fiber 1112 being optically coupled to both LEDs 1110a and 1110b. The LEDs may also be energized and de-energized by use of a switch or touch sensor that is operable by a human hand. FIG. 19C illustrates a schematic drawing of such a control circuit wherein a button, capacitor or touch sensor 1120 is operable to send a signal to the LED 1121 to cause the LED to energize to cause an illumination of the optical fiber 1122.

According to other implementations LED 1110a is configured to emit visible light of a first color and LED 1110b is configured to emit light of a second color. According to such implementations upon the occurrence of an incoming phone call the control circuit may be configured to cause LED 1110a to illuminate and upon the occurrence of an incoming text the control circuit may be configured to cause the LED 1110b to be energized.

According to one implementation one or both of LEDs 1110a and 1110b may be configured to emit light capable of killing bacteria, viruses, etc. Because the production of disinfecting light typically requires a substantial amount of power, the control circuit may be configured to allow the illumination of the LEDs only upon receiving a signal indicative of the power cord being attached to the device.

According to some implementations the light diffusing optical fiber 1112 is optical coupled to one or more of the LEDs configured to emit bacterial disinfecting light and one or more LEDs configured to emit visible light of the same color or different colors.

FIG. 19B illustrates another implementation similar to that of FIG. 19A with the light diffusing optical fiber 1112 being embedded inside the glass plate that lies over the device display 1101. The light diffusing optical fiber is preferable integrated into the edge of the glass plate of the smart device.

The implementations associated with smart devices are also configurable for placement in other handheld devices and devices that are operated by the human hand.

The following clauses disclose in an unlimited way additional implementations, with each clause representing an implementation.

Group A clauses:

Clause 1: a frame including a front side, a backside and a cavity located between the front side and backside that opens to the front side;

first and second electrically conductive pads located on the frame;

a first light emitting diode having an anode and a cathode, the first light emitting diode being located inside the cavity of the frame with the anode and cathode respectively being electrically coupled to the first and second electrically conductive pads;

a first optical fiber having a core and a cladding surrounding the core, the first optical fiber including a proximal end portion having a first light receiving end that is butt-coupled to the first light emitting diode;

a lid located distal to the first light emitting diode, the lid having a front side, a backside, and a through opening that extends between and through the front side and backside of the lid, the backside of the lid being attached to the front side of the frame, the first optical fiber extending through and being supported in the through opening; and a printed circuit board having a voltage terminal and a ground terminal, the first electrically conductive pad of the frame being electrically connected to the voltage terminal and the second electrically conductive pad of the frame being electrically connected to the ground terminal.

Figure 18A:
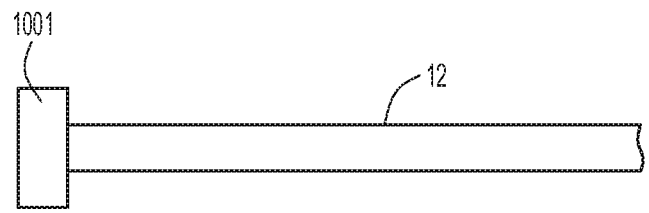
FIGS. 18A-U schematically show light diffusing fiber and light emitting diode configurations according to various implementations disclosed herein.

FIG. 18A schematically shows a single light diffusing fiber 12 being butt-coupled to a single LED 1001.

Clause 2: The assembly according to clause 1, further comprising a resilient strain relief housing enclosing at least a portion of the first optical fiber, the resilient strain relief housing having a proximal end that butts against the front side of the lid.

Clause 3. The assembly according to clause 1, further comprising a resilient strain relief housing enclosing at least a portion of the first optical fiber, the resilient strain relief housing having a proximal end portion that resides inside the through opening of the lid.

Clause 4. The assembly according to clause 1, wherein the proximal end portion of the first optical fiber protrudes proximally from the backside of the lid into the cavity of the frame.

Clause 5. The assembly according to clause 4, wherein the first light emitting diode includes a front side from which light is emitted, a distance between the backside of the lid and the front side of the first light emitting diode is equal to or less than 1 millimeter.

Clause 6. The assembly according to clause 1, wherein at least a portion of each of the first and second electrically conductive pads of the frame is located on the backside of the frame, the first electrically conductive pad being electrically coupled to the voltage terminal of the printed circuit board via a first electrically conductive pin that extends through a topside of the printed circuit board, the second electrically conductive pad being electrically coupled to the ground terminal of the printed circuit board via a second electrically conductive pin that extends through the topside of the printed circuit board.

Clause 7. The assembly according to clause 6, wherein each of the first and second electrically conductive pads comprises a solder and is respectively electrically coupled to the voltage terminal and the ground terminal of the printed circuit board by the solder.

Clause 8. The assembly according to clause 1, wherein at least a portion of each of the first and second electrically conductive pads of the frame is located on a bottom side of the frame, each of the voltage terminal and ground terminal of the printed circuit board respectively comprising first and second metallic pads residing on the top side surface of the printed circuit board, the first and second electrically conductive pads of the frame being respectively surface mounted in an electrically conducive manner to the first and second metallic pads of the printed circuit board.

Clause 9. The assembly according to clause 8, wherein each of the first and second electrically conductive pads comprises a solder and is respectively electrically coupled to the first and second metallic pads of the printed circuit board by the solder.

Clause 10. The assembly according to clause 1, wherein the anode of the first light emitting diode is electrically coupled to the first electrically conductive pad by an electrically conductive wire having a first end and a second end, the first end being attached to and electrically coupled to the anode of the first light emitting diode, the second end being attached to and electrically coupled to the first electrically conductive pad.

Clause 11. The assembly according to clause 1, wherein the anode of the first light emitting diode is electrically coupled to a first electrical conductor element residing inside the frame, the first electrical conductor element comprising a first metallic mass that is electrically coupled to the first electrically conductive pad.

Clause 12. The assembly according to clause 11, wherein the anode of the first light emitting diode is electrically coupled to the first electrical conductor element by an electrically conductive wire having a first end and a second end, the first end being attached to and electrically coupled to the anode of the first light emitting diode, the second end being attached to and electrically coupled to the first electrical conductor element.

Clause 13. The assembly according to clause 1, wherein the cathode of the first light emitting diode is electrically coupled to a second electrical conductor element residing inside the frame, the second electrical conductor element comprising a second metallic mass that is electrically coupled to the second electrically conductive pad.

Clause 14. The assembly according to clause 13, wherein the cathode of the first light emitting diode is surface mounted to the second electrical conductor element.

Clause 15. The assembly according to clause 12, wherein the cathode of the first light emitting diode is electrically coupled to a second electrical conductor element residing inside the frame, the second electrical conductor element comprising a second metallic mass that is electrically coupled to the second electrically conductive pad.

Clause 16. The assembly according to clause 15, wherein the cathode of the first light emitting diode is surface mounted to the second electrical conductor element.

Clause 17. The assembly according to clause 3, wherein a periphery of the proximal end portion of the resilient strain relief housing is in sealing engagement with an internal wall of the lid that forms the through opening.

Clause 18. The assembly according to clause 12, wherein the resilient strain relief housing is made of rubber.

Clause 19. The assembly according to clause 1, wherein the first light emitting diode comprises a light emitting side and each of the core and cladding at the light receiving end of the first optical fiber is butt-coupled to the light emitting side of the first light emitting diode.

Clause 20. The assembly according to clause 1, wherein the through opening of the lid has a length dimension and a portion of the first optical fiber residing in the through opening has an outer diameter dimension, the length dimension being greater than the outer diameter dimension.

Clause 21. The assembly according to clause 1, further comprising:
a second light emitting diode located inside the cavity of the frame; and
a second optical fiber having a core and a cladding surrounding the core, the second optical fiber having a light receiving end that is optically coupled to the second light emitting diode, the second optical fiber extending through and being supported in the through opening of the lid.

Figure 18B:
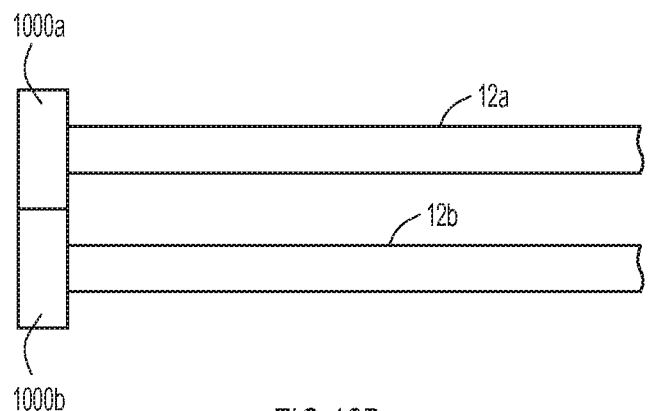

FIG. 18B schematically shows first and second light diffusing fibers 12a and 12b being respectively butt-coupled to first and second LEDs 1001a and 1001b.

Clause 22. The assembly according to clause 21, wherein the first light emitting diode emits ultraviolet light and the second light emitting diode emits visible light.

Clause 23. The assembly according to clause 22, wherein the first and second light emitting diodes are configured to be concurrently energized to concurrently deliver ultraviolet light and visible light into the first light diffusing optical fiber.

Clause 24. The assembly according to clause 1, wherein the core of the first light diffusing optical fiber has a distal end opposite the proximal end that is optically coupled to a second light emitting diode.

Figure 18C:
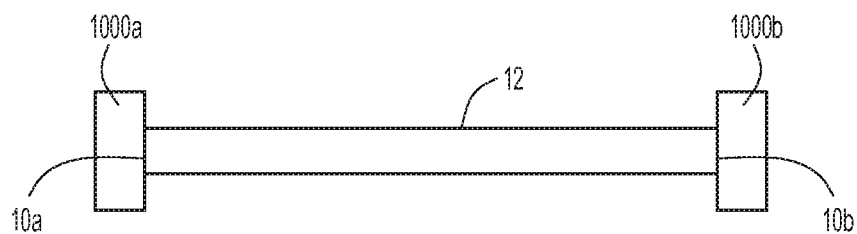

FIG. 18C schematically shows a single light diffusing fiber 12 being butt-coupled at a first end 10a to a first LED 1001a and at a second end 10b to a second LED 1001b.

Clause 25. The assembly according to clause 24, wherein the first light emitting diode emits ultraviolet light and the second light emitting diode emits visible light.

Group B clauses:

Clause 1. An assembly comprising:
a frame including a front side, a backside and a cavity located between the front side and backside that opens to the front side;
a first light emitting diode being located inside the cavity of the frame;
a first optical fiber having a core and a cladding that surrounds the core, the first optical fiber including a proximal end portion having a first light receiving end that is optically coupled to the first light emitting diode; and a lid constructed of a rigid material located distal to the first light emitting diode, the lid having a front side, a backside, and a through opening that extends between and through the front side and backside of the lid, the backside of the lid being attached to the front side of the frame, the first optical fiber extending through and being supported in the through opening, the through opening of the lid having a length dimension and a portion of the first optical fiber residing in the through opening having an outer diameter dimension, the length dimension being greater than the outer diameter dimension.

Clause 2. The assembly according to clause 1, further comprising a resilient strain relief housing enclosing at least a portion of the first optical fiber, the resilient strain relief housing having a proximal end that butts against the front side of the lid.

Clause 3. The assembly according to clause 1, further comprising a resilient strain relief housing enclosing at least a portion of the first optical fiber, the resilient strain relief housing having a proximal end portion that resides inside the through opening of the lid.

Clause 4. The assembly according to clause 3, wherein a periphery of the proximal end portion of the resilient strain relief housing is in sealing engagement with an internal wall of the lid that forms the through opening.

Clause 5. The assembly according to clause 1, wherein the proximal end portion of the first optical fiber protrudes proximally from the backside of the lid into the cavity of the frame.

Clause 6. The assembly according to clause 5, wherein the first light emitting diode includes a front side from which light is emitted, a distance between the backside of the lid and the front side of the first light emitting diode is equal to or less than 1 millimeter.

Clause 7. The assembly according to clause 1, wherein the first optical fiber is secured inside the through opening of the lid by an adhesive.

Clause 8. The assembly according to clause 3, wherein the through opening of the lid comprises a first bore that opens to the front side of the lid and a second bore that opens to the backside of the lid, the first bore having a first diameter and the second bore having a second diameter that is less than the first diameter.

Clause 9. The assembly according to clause 8, wherein the proximal end portion of the resilient strain relief housing resides inside the first bore.

Clause 10. The assembly according to clause 1, wherein the through opening of the lid has a diameter that is between 1% to 10% greater than an outer-most diameter of a portion of the first optical fiber that passes through the through opening.

Clause 11. The assembly according to clause 8, wherein the second bore has a diameter that is no more than 10% greater than an outer-most diameter of a portion of the first optical fiber that passes through the second bore.

Clause 12. The assembly according to clause 9, wherein the second bore has a diameter that is no more than 10% greater than an outer-most diameter of a portion of the first optical fiber that passes through the second bore.

Clause 13. The assembly according to clause 1, wherein a refractive index matching material is disposed between a proximal end of the core of the first optical fiber and the first light emitting diode.

Clause 14. The assembly according to clause 13, wherein the refractive index matching material is an adhesive.

Clause 15. The assembly according to clause 13, wherein the refractive index matching material has a refractive index that is less than the refractive index of air.

Clause 16. The assembly according to clause 3, wherein a proximal end portion of the through opening comprises a distal facing annular surface, the resilient strain relief housing having a distal end that abuts the distal facing annular surface.

Clause 17. The assembly according to clause 1, wherein the optical fiber has a first portion and a second portion distal to the second portion, the first portion extending through the through opening of the lid and being devoid of a cladding, the second portion including a cladding and having an outer diameter that is greater than an outer diameter of the first portion, the second end portion not residing in the through opening of the lid with the cladding of the second portion abutting the front side of the lid.

Clause 18. The assembly according to clause 3, wherein the through opening of the lid comprises a first bore that opens to the front side of the lid and a second bore that opens to the backside of the lid, the first bore having a first diameter and the second bore having a second diameter that is less than the first diameter, the through opening including an annular surface at the juncture of the first and second bores, the optical fiber having a first portion and a second portion distal to the second portion, the first portion extending through the second of the lid and being devoid of a cladding, the second portion including a cladding and having an outer diameter that is greater than an outer diameter of the first portion, a proximal end of the second end portion residing in the first bore of the lid with the cladding of the second portion abutting the annular surface of the through opening.

Clause 19. The assembly according to clause 1, wherein the cavity of the frame is at least partially filled with an optically transparent epoxy that is interposed between the light emitting diode and the proximal end of the first optical fiber.

Clause 20. The assembly according to clause 19, wherein the frame includes an injection hole for use in injecting the epoxy into the cavity of the frame.

Group C clauses:

Clause 1. An assembly comprising:

a frame including a front side, a backside and a cavity located between the front side and backside that opens to the front side;

first, second and third electrically conductive pads located on the frame;

a first light emitting diode having an anode and a cathode, the first light emitting diode being located inside the cavity of the frame with the anode and cathode respectively being electrically coupled to the first electrically conductive pad and the third electrically conductive pad;

a second light emitting diode having an anode and a cathode, the second light emitting diode being located inside the cavity of the frame with the anode and cathode respectively being electrically coupled to the second electrically conductive pad and the third electrically conductive pad;

a first light diffusing optical fiber having a core and a cladding surrounding the core, the core having a proximal end that is butt-coupled to the first and second light emitting diodes;

a lid having a front side, a backside, and a through opening that extends between and through the front side and backside of the lid, the backside of the lid being attached to the front side of the frame, the first light diffusing optical fiber extending through the through opening; and a printed circuit board having first and second power supply voltage terminals and a power supply ground terminal, the first and second electrically conductive pads of the frame being respectively electrically coupled to the first and second voltage terminals and the third electrically conductive pad of the frame being electrically coupled to the ground terminal.

Figure 18D:
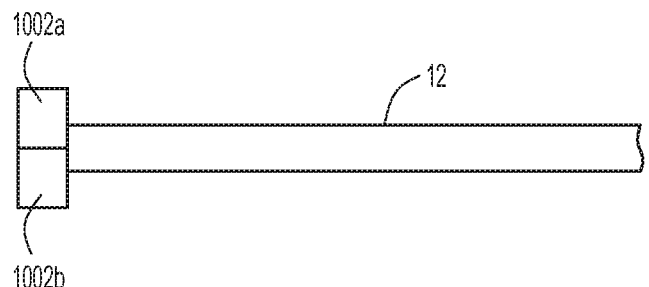

FIG. 18D schematically shows a single light diffusing fiber 12 being butt-coupled at one end to first and second LEDs 1002a and 1002b.

Clause 2. The assembly according to clause 1, wherein the first light emitting diode emits light of a first color and the second light emitting diode emits light of a second color that is different from the first color.

Clause 3. The assembly according to clause 1, wherein the first light emitting diode emits visible light and the second light emitting diode emits infrared light.

Clause 4. The assembly according to clause 1, wherein the first light emitting diode emits visible light and the second light emitting diode emits disinfecting ultraviolet light.

Clause 5. The assembly according to clause 1, further comprising a resilient strain relief housing enclosing at least a portion of the first light diffusing optical fiber, the resilient strain relief having a proximal end portion that resides inside the through opening of the lid.

Clause 6. The assembly according to clause 1, wherein the proximal end of the first light diffusing optical fiber protrudes proximally from the backside of the lid.

Clause 7. The assembly according to clause 1, wherein each of the first and second light emitting diode includes a front side from which light is emitted, a distance between the backside of the lid and the front side of the first and second light emitting diodes being equal to or less than 1 millimeter.

Clause 8. The assembly according to clause 1, wherein each of the first and second electrically conductive pads and third electrically conductive pad of the frame is located on the backside of the frame, the first and second electrically conductive pads being respectively coupled to the first and second voltage terminals of the printed circuit board via a first and second electrically conductive pins that extend into the printed circuit board, the third electrically conductive pad of the frame being coupled to the ground terminal of the printed circuit board via a third electrically conductive pin that extends into the printed circuit board.

Clause 9. The assembly according to clause 1, wherein each of the first, second and third voltage terminals and ground terminal of the printed circuit board reside on a surface of the printed circuit board, the first, second and third electrically conductive pads and of the frame being respectively surface mounted in an electrically conducive manner to the first and second voltage terminal and ground terminal.

Clause 10. The assembly according to clause 1, wherein each of the anodes of the first and second light emitting diodes is respectively electrically coupled to the first and second electrically conductive pads of the frame by first and second electrically conductive wires that each have a first end and a second end, the first ends of the first and second electrically conductive wires being respectively attached to and electrically coupled to the anodes of the first and second light emitting diodes, the second ends of the first and second electrically conductive wires being respectively attached to and electrically coupled to the first and second electrically conductive pads of the frame.

Clause 11. The assembly according to clause 1, wherein the anode of each of the first and second light emitting diode is respectively electrically coupled to a first and second electrical conductor elements residing inside the frame, the first and second electrical conductor elements respectively comprising a first and second metallic mass that is respectively electrically coupled to the first and second electrically conductive pad.

Clause 12. The assembly according to clause 11, wherein the anode of the first light emitting diode is electrically coupled to the first electrical conductor element by a first electrically conductive wire having a first end and a second end, the first end being attached to and electrically coupled to the anode of the first light emitting diode, the second end being attached to and electrically coupled to the first electrical conductor element, and the anode of the second light emitting diode is electrically coupled to the second electrical conductor element by a second electrically conductive wire having a first end and a second end, the first end being attached to and electrically coupled to the anode of the second light emitting diode, the second end being attached to and electrically coupled to the second electrical conductor element.

Clause 13. The assembly according to clause 1, wherein the cathode of each of the first and second light emitting diodes is electrically coupled to a third electrical conductor element residing inside the frame, the second electrical conductor element comprising a third metallic mass that is electrically coupled to the third electrically conductive pad.

Clause 14. The assembly according to clause 13, wherein the cathode of each of the first and second light emitting diodes is surface mounted to the third electrical conductor element in an electrically conductive manner.

Clause 15. The assembly according to clause 12, wherein the cathode of each of the first and second light emitting diodes is electrically coupled to a third electrical conductor element residing inside the frame, the third electrical conductor element comprising a third metallic mass that is electrically coupled to the third electrically conductive pad.

Clause 16. The assembly according to clause 15, wherein the cathode of each of the first and second light emitting diodes is surface mounted to the third electrical conductor element.

Clause 17. The assembly according to clause 5, wherein a periphery of the proximal end portion of the resilient strain relief housing is in sealing engagement with an internal wall of the lid that forms the through opening.

Clause 18. The assembly according to clause 1, wherein the cladding of the first light diffusing optical fiber abuts the front side of one or both of the first and second light emitting diodes.

Clause 19. The assembly according to clause 5, wherein the through opening of the lid comprises a first bore that opens to the front side of the lid and a second bore that opens to the backside of the lid, the first bore having a first diameter and the second bore having a second diameter that is less than the first diameter, at least a portion of the first light diffusing optical fiber being fixed inside the second bore; the distal end portion of the resilient strain relief housing residing inside the first bore.

Clause 20. The assembly according to clause 19, wherein the second bore has a diameter that is not more than 10% greater than an outer-most diameter of a portion of the first light diffusing optical fiber that passes through the second bore.

Clause 21. The assembly according to clause 1, wherein the first light diffusing optical fiber is secured inside the through opening of the lid by an adhesive.

Clause 22. The assembly according to clause 1, wherein a refractive index matching material is disposed between the proximal end of the core of the first light diffusing optical fiber and the front side of the first and second light emitting diodes.

Clause 23. The assembly according to clause 22, wherein the refractive index matching material is an adhesive.

Clause 24. The assembly according to clause 19, wherein a proximal end of the first bore comprises a distal facing annular surface, the proximal end of the resilient strain relief housing abutting the distal facing annular surface.

Clause 25. The assembly according to clause 1, wherein the core of the first light diffusing optical fiber has a distal end opposite the proximal end that is optically coupled to a third light emitting diode.

Figure 18E:
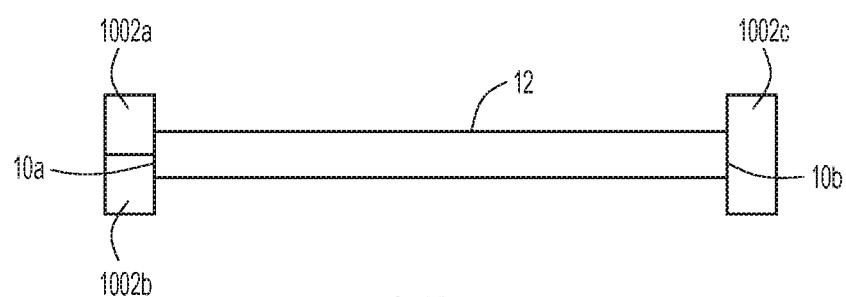

FIG. 18E schematically shows a single light diffusing fiber 12 being butt-coupled at a first end 10a to first and second LEDs 1002a and 1002b and at a second end 10b to a third LED 1002c.

Clause 26. The assembly according to clause 25, wherein the third light emitting diode emits light of a first color, the second light emitting diode emits light of a second color that is different from the first color and the third light emitting diode emits light of a third color that is different from the first and second colors.

Clause 27. The assembly according to clause 25, wherein each of the first and third light emitting diodes emit ultraviolet light and the second light emitting diode emits visible light or infrared light.

Clause 28. The assembly according to clause 1, wherein the first light emitting diode emits ultraviolet light and the second light emitting diode emits visible light.

Clause 29. The assembly according to clause 28, wherein the first and second light emitting diodes are configured to be concurrently energized to concurrently deliver ultraviolet light and visible light to the first light diffusing optical fiber.

Group D Clauses:

Clause 1. An assembly comprising:

a frame including a front side, a backside and a cavity located between the front side and backside that opens to the front side;

first, second, third and fourth electrically conductive pads located on the frame;

a first light emitting diode having an anode and a cathode, the first light emitting diode being located inside the cavity of the frame with the anode and cathode respectively being electrically connected to the first and fourth electrically conductive pad;

a second light emitting diode having an anode and a cathode, the second light emitting diode being located inside the cavity of the frame with the anode and cathode respectively being electrically connected to the second and fourth electrically conductive pad;

a third light emitting diode having an anode and a cathode, the third light emitting diode being located inside the cavity of the frame with the anode and cathode respectively being electrically connected to the third and fourth electrically conductive pad;

a first light diffusing optical fiber having a core and a cladding surrounding the core, the core having a proximal end that is butt-coupled to the first, second and third light emitting diodes;

a lid having a front side, a backside, and a through opening that extends between and through the front side and backside of the lid, the backside of the lid being attached to the front side of the frame, the first light diffusing optical fiber extending through the through opening; and a printed circuit board having first, second and third power supply voltage terminals and a power supply ground terminal, the first, second, third and fourth anode electrically conductive pads being respectively electrically coupled to the first, second and third voltage terminals and to the ground terminal.

Figure 18F:
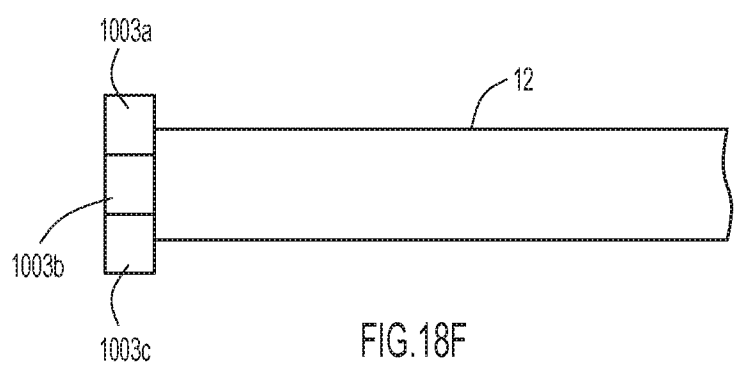
Figure 18G:
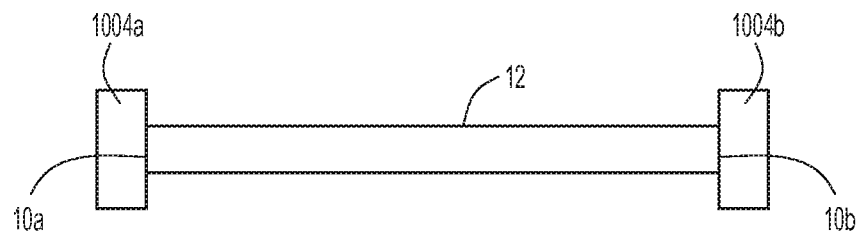

FIG. 18F schematically shows a single light diffusing fiber 12 being butt-coupled at one end to first, second and third LEDs 1003a, 1003b and 1003c.

Clause 2. The assembly according to clause 1, wherein the first light emitting diode emits red light, the second light emitting diode emits green light, the third light emitting diode emits ultraviolet light.

Clause 3. The assembly according to clause 1, further comprising a resilient strain relief housing enclosing at least a portion of the first light diffusing optical fiber, the resilient strain relief having a proximal end portion that resides inside the through opening of the lid.

Clause 4. The assembly according to clause 1, wherein the proximal end of the first light diffusing optical fiber protrudes proximally from the backside of the lid.

Clause 5. The assembly according to clause 1, wherein each of the first, second and third light emitting diodes includes a front side from which light is emitted, a distance between the backside of the lid and the front side of the first, second and third light emitting diodes being equal to or less than 1 millimeter.

Clause 6. The assembly according to clause 1, wherein each of the first, second third and fourth electrically conductive pad is located on the backside of the frame, the first, second and third electrically conductive pads being respectively coupled to the first, second and third voltage terminals of the printed circuit board via a first, second and third electrically conductive pins that extend into the printed circuit board, the fourth electrically conductive pad being coupled to the ground terminal of the printed circuit board via a fourth electrically conductive pin that extends into the printed circuit board.

Clause 7. The assembly according to clause 1, wherein each of the first, second, third and fourth electrically conductive pads is located on a bottom side of the frame, each of the first, second and third voltage terminals and ground terminal of the printed circuit board residing on a surface of the printed circuit board, the first, second, third and fourth electrically conductive pads being respectively surface mounted in an electrically conducive manner to the first, second and third voltage terminal and ground terminal.

Clause 8. The assembly according to clause 1, wherein each of the anodes of the first, second and third light emitting diodes is respectively electrically coupled to the first, second and third electrically conductive pad by first, second and third electrically conductive wires that each have a first end and a second end, the first ends of the first, second and third electrically conductive wires being respectively attached to and electrically coupled to the anodes of the first, second and third light emitting diodes, the second ends of the first, second and third electrically conductive wires being respectively attached to and electrically coupled to the first, second and third anode connectors of the frame.

Clause 9. The assembly according to clause 1, wherein the anode of each of the first, second and third light emitting diode is respectively electrically coupled to a first, second and third electrical conductor elements residing inside the frame, the first, second and third electrical conductor elements respectively comprising a first, second and third metallic mass that is respectively electrically coupled to the first, second and third electrically conductive pad.

Clause 10. The assembly according to clause 9, wherein the anode of the first light emitting diode is electrically coupled to the first electrical conductor element by a first electrically conductive wire having a first end and a second end, the first end being attached to and electrically coupled to the anode of the first light emitting diode, the second end being attached to and electrically coupled to the first electrical conductor element, the anode of the second light emitting diode is electrically coupled to the second electrical conductor element by a second electrically conductive wire having a first end and a second end, the first end being attached to and electrically coupled to the anode of the second light emitting diode, the second end being attached to and electrically coupled to the second electrical conductor element, and the anode of the third light emitting diode is electrically coupled to the third electrical conductor element by a third electrically conductive wire having a first end and a second end, the first end being attached to and electrically coupled to the anode of the third light emitting diode, the second end being attached to and electrically coupled to the third electrical conductor element.

Clause 11. The assembly according to clause 1, wherein the cathode of each of the first, second and third light emitting diode is electrically coupled to a fourth electrical conductor element residing inside the frame, the fourth electrical conductor element comprising a fourth metallic mass that is electrically coupled to the fourth electrically conductive pad.

Clause 12. The assembly according to clause 11, wherein the cathode of each of the first, second and third light emitting diodes is surface mounted to the fourth electrical conductor element in an electrically conductive manner.

Clause 13. The assembly according to clause 10, wherein the cathode of each of the first, second and third light emitting diodes is electrically coupled to a fourth electrical conductor element residing inside the frame, the fourth electrical conductor element comprising a fourth metallic mass that is electrically coupled to the fourth electrically conductive pad.

Clause 14. The assembly according to clause 13, wherein the cathode of each of the first, second and third light emitting diodes is surface mounted to the fourth electrical conductor element in an electrically conductive manner.

Clause 15. The assembly according to clause 3, wherein a periphery of the proximal end portion of the resilient strain relief housing is in sealing engagement with an internal wall of the lid that forms the through opening.

Clause 16. The assembly according to clause 1, wherein the cladding of the first light diffusing optical fiber abuts the front side of the first, second and third light emitting diodes.

Clause 17. The assembly according to clause 3, wherein the through opening of the lid comprises a first bore that opens to the front side of the lid and a second bore that opens to the backside of the lid, the first bore having a first diameter and the second bore having a second diameter that is less than the first diameter, at least a portion of the first light diffusing optical fiber being fixed inside the second bore; the distal end portion of the resilient strain relief housing residing inside the first bore.

Clause 18. The assembly according to clause 17, wherein the first light diffusing optical fiber is secured inside the second bore by use of an adhesive.

Clause 19. The assembly according to clause 1, wherein a refractive index matching material is disposed between the proximal end of the core of the first light diffusing optical fiber and the front side of the first, second and third light emitting diodes.

Clause 20. The assembly according to clause 19, wherein the refractive index matching material is an adhesive.

Clause 21. The assembly according to clause 17, wherein a proximal end of the first bore comprises a distal facing annular surface, the proximal end of the resilient strain relief housing abutting the distal facing annular surface.

Clause 22. The assembly according to clause 1, further comprising an injection port that extends from an external surface of the frame to the cavity of the frame to facilitate an injection of an index matching material into the cavity.

Group E Clauses:

Clause 1. An assembly comprising:

a frame including a front side, a backside and a cavity located between the front side and backside that opens to the front side;

a first and second electrically conductive pads located on the frame;

a first light emitting diode having an anode and a cathode, the first light emitting diode being located inside the cavity of the frame with the anode and cathode respectively being electrically connected to the first and second electrically conductive pad;

a first light diffusing optical fiber having a core and a cladding surrounding the core, the core of the first light diffusing optical fiber having a proximal end that is butt-coupled to the first light emitting diode;

a second light diffusing optical fiber having a core and a cladding surrounding the core, the core of the second light diffusing optical fiber having a proximal end that is butt-coupled to the first light emitting diode;

a lid having a front side, a backside, and a through opening that extends between and through the front side and backside of the lid, the backside of the lid being attached to the front side of the frame, the first and second light diffusing optical fibers extending through the through opening; and a printed circuit board having a voltage terminal and a ground terminal, the first electrically conductive pad being electrically coupled to voltage terminal and the second electrically conductive pad being electrically coupled to the ground terminal.

Clause 2. The assembly according to clause 1, further comprising a resilient strain relief housing enclosing at least a portion of the first and second light diffusing optical fibers, the resilient strain relief having a proximal end portion that resides inside the through opening of the lid.

Clause 3. The assembly according to clause 1, wherein the proximal end of each of the first and second light diffusing optical fibers protrudes proximally from the backside of the lid.

Clause 4. The assembly according to clause 1, wherein the first light emitting diode includes a front side from which light is emitted, a distance between the backside of the lid and the front side of the first light emitting diode being equal to or less than 1 millimeter.

Clause 5. The assembly according to clause 1, wherein the first and second electrically conductive pads are located on the backside of the frame, the first electrically conductive pad being coupled to the voltage terminal of the printed circuit board via a first electrically conductive pin that extends into the printed circuit board, the second electrically conductive pad being coupled to the ground terminal of the printed circuit board via a second electrically conductive pin that extends into the printed circuit board.

Clause 6. The assembly according to clause 1, wherein each of the voltage terminal and ground terminal of the printed circuit board resides on a surface of the printed circuit board, the first and second electrically conductive pads being respectively surface mounted in an electrically conducive manner to the voltage terminal and ground terminal.

Clause 7. The assembly according to clause 1, wherein the anode of the first light emitting diode is electrically coupled to the first electrically conductive pad by an electrically conductive wire having a first end and a second end, the first end being attached to and electrically coupled to the anode of the first light emitting diode, the second end being attached to and electrically coupled to the anode connector located on the frame.

Clause 8. The assembly according to clause 1, wherein the anode of the first light emitting diode is electrically coupled to a first electrical conductor element residing inside the frame, the first electrical conductor element comprising a first metallic mass that is electrically coupled to the first electrically conductive pad.

Clause 9. The assembly according to clause 8, wherein the anode of the first light emitting diode is electrically coupled to the first electrical conductor element by an electrically conductive wire having a first end and a second end, the first end being attached to and electrically coupled to the anode of the first light emitting diode, the second end being attached to and electrically coupled to the first electrical conductor element.

Clause 10. The assembly according to clause 1, wherein the cathode of the first light emitting diode is electrically coupled to a second electrical conductor element residing inside the frame, the second electrical conductor element comprising a second metallic mass that is electrically coupled to the second electrically conductive pad.

Clause 11. The assembly according to clause 10, wherein the cathode of the first light emitting diode is surface mounted to the second electrical conductor element.

Clause 12. The assembly according to clause 9, wherein the cathode of the first light emitting diode is electrically coupled to a second electrical conductor element residing inside the frame, the second electrical conductor element comprising a second metallic mass that is electrically coupled to the second electrically conductive pad.

Clause 13. The assembly according to clause 12, wherein the cathode of the first light emitting diode is surface mounted to the second electrical conductor element.

Clause 14. The assembly according to clause 2, wherein a periphery of the proximal end portion of the resilient strain relief housing is in sealing engagement with an internal wall of the lid that forms the through opening.

Clause 15. The assembly according to clause 1, wherein the cladding of the first light diffusing optical fiber abuts the front side of the first and second light emitting diodes.

Clause 16. The assembly according to clause 2, wherein the through opening of the lid comprises a first bore that opens to the front side of the lid and a second bore that opens to the backside of the lid, the first bore having a first diameter and the second bore having a second diameter that is less than the first diameter, at least a portion of the first and second light diffusing optical fibers being fixed inside the second bore; the distal end portion of the resilient strain relief housing residing inside the first bore.

Clause 17. The assembly according to clause 16, wherein the first and second light diffusing optical fibers are secured inside the second bore by use of an adhesive.

Clause 18. The assembly according to clause 1, wherein a refractive index matching material is disposed between the proximal end of the core of each of the first and second light diffusing optical fibers and the front side of the first light emitting diode.

Clause 19. The assembly according to clause 18, wherein the refractive index matching material is an adhesive.

Clause 20. The assembly according to clause 16, wherein a proximal end of the first bore comprises a distal facing annular surface, the proximal end of the resilient strain relief housing abutting the distal facing annular surface.

Clause 21. The assembly according to clause 1, further comprising an injection port that extends from an external surface of the lid to the cavity of the frame to facilitate an injection of an index matching material into the cavity of the frame.

Group F Clauses:

Clause 1. An assembly comprising:

a first frame including a front side, a backside and a cavity located between the front side and backside that opens to the front side;

first and second electrically conductive pads located on the first frame;

a first light emitting diode having an anode and a cathode, the first light emitting diode being located inside the cavity of the first frame with the anode and cathode respectively being electrically coupled to the first and second electrically conductive pad;

a first light diffusing optical fiber having a core and a cladding surrounding the core, the first light diffusing optical fiber having a first end and an opposite second end, the first end being optically coupled to the first light emitting diode;

a first lid having a front side, a backside, and a through opening that extends between and through the front side and backside of the first lid, the backside of the first lid being attached to the front side of the first frame, a first portion of the first light diffusing optical fiber extending through and being supported in the through opening of the first lid;

a first printed circuit board having a voltage terminal and a ground terminal, the first electrically conductive pad of the first frame being electrically coupled to the voltage terminal of the first printed circuit board and the second electrically conductive pad of the first frame being electrically coupled to the ground terminal of the printed circuit board:

a second frame including a front side, a backside and a cavity located between the front side and backside that opens to the front side;

first and second electrically conductive pads located on the second frame;

a second light emitting diode having an anode and a cathode, the second light emitting diode being located inside the cavity of the second frame with the anode and cathode respectively being electrically coupled to the first and second electrically conductive pads of the second frame;

the second end of the first light diffusing optical fiber being optically coupled to the second light emitting diode;

a second lid having a front side, a backside, and a through opening that extends between and through the front side and backside of the second lid, the backside of the second lid being attached to the front side of the second frame, a second portion of the first light diffusing optical fiber extending through and being supported in the through opening of the second lid; and a second printed circuit board having a voltage terminal and a ground terminal, the first electrically conductive pad of the second frame being electrically connected to the voltage terminal of the second printed circuit board and the second electrically conductive pad of the second frame being electrically connected to the ground terminal of the second printed circuit board.

FIG. 18F schematically shows a single light diffusing fiber 12 being butt-coupled at a first end 10a to a first LED 1004a and at a second end 10b to a second LED 1004b.

Clause 2. The assembly according to clause 1, further comprising:

a first resilient strain relief housing enclosing at least a portion of the first light diffusing optical fiber, the first resilient strain relief having an end portion that resides inside the through opening of the first lid; and a second resilient strain relief housing enclosing at least a portion of the second light diffusing optical fiber, the second resilient strain relief having an end portion that resides inside the through opening of the second lid.

Clause 3. The assembly according to clause 1, further comprising a second light diffusing optical fiber having a core and a cladding surrounding the core, the second light diffusing optical fiber having a first end and an opposite second end, the first end of the second light diffusing optical fiber being optically coupled to the first light emitting diode.

Figure 18H:
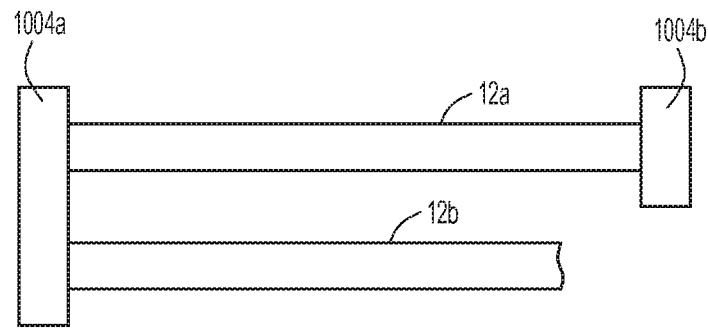

FIG. 18H schematically shows a first light diffusing fiber 12a being butt-coupled at a first end 10a to a first LED 1004a and at a second end 10b to a second LED 1004b. An end of a second light diffusing fiber 12b is also butt-coupled to the first LED 1004a.

Clause 4. The assembly according to clause 3, wherein the second end of the second light diffusing optical fiber is optically coupled to the second light emitting diode.

Figure 18I:
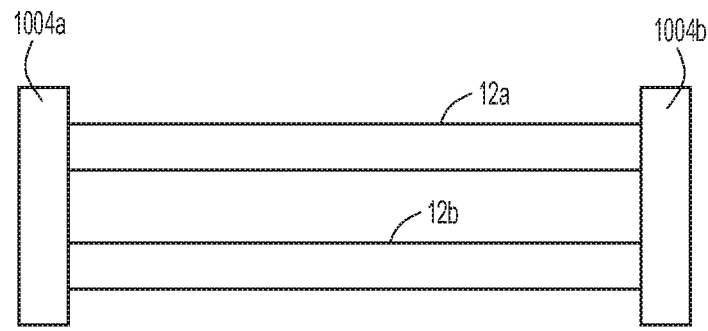

FIG. 18I schematically shows a first and second light diffusing fibers 12a and 12b that are each butt-coupled at a first end to a first LED 1004a and at a second end to a second LED 1004b.

Clause 5. The assembly according to clause 3, wherein a proximal end portion of the second light diffusing optical fiber extends through the through opening of the first lid, the first resilient strain relief housing enclosing at least a portion of the second light diffusing optical fiber.

Clause 6. The assembly according to clause 1, wherein the first light emitting diode emits visible light and the second light emitting diode emits ultraviolet light.

Clause 7. The assembly according to clause 1, wherein the first light emitting diode emits visible light of a first color and the second light emitting diode emits visible light of a second color different from the first color.

Clause 8. The assembly according to clause 1, wherein the first light emitting diode emits visible light and the second light emitting diode emits infrared light.

Clause 9. The assembly according to clause 1, wherein the proximal end of the first light diffusing optical fiber protrudes from the backside of the first lid towards the first light emitting diode and the distal end of the first light diffusing optical fiber protrudes from the backside of the second lid towards the second light emitting diode.

Clause 10. The assembly according to clause 1, wherein each of the first and second light emitting diodes includes a front side from which light is emitted, a first distance between the backside of the first lid and the front side of the first light emitting diode being equal to or less than 1 millimeter, a second distance between the backside of the second lid and the front side of the second light emitting diode being equal to or less than 1 millimeter.

Clause 11. The assembly according to clause 1, wherein each of the first and second electrically conductive pads of the first frame are located on the backside of the first frame, the electrically conductive pad of the first frame being electrically coupled to the voltage terminal of the first printed circuit board via a first electrically conductive pin that extends into the first printed circuit board, the second electrically conductive pad of the first frame being coupled to the ground terminal of the first printed circuit board via a second electrically conductive pin that extends into the first printed circuit board.

Clause 12. The assembly according to clause 11, wherein each of the first and second electrically conductive pads of the second frame are located on the backside of the second frame, the first electrically conductive pad of the second frame being coupled to the voltage terminal of the second printed circuit board via a first electrically conductive pin that extends into the second printed circuit board, the second electrically conductive pad of the second frame being coupled to the ground terminal of the second printed circuit board via a second electrically conductive pin that extends into the second printed circuit board.

Clause 13. The assembly according to clause 1, wherein the voltage terminal and ground terminal of the first printed circuit board reside on a surface of the first printed circuit board, the first and second electrically conductive pads of the first frame being respectively surface mounted in an electrically conducive manner to the voltage terminal and ground terminal of the first printed circuit board.

Clause 14. The assembly according to clause 13, wherein the voltage terminal and ground terminal of the second the printed circuit board reside on a surface of the second printed circuit board, the first and second electrically conductive pad of the second frame being respectively surface mounted in an electrically conducive manner to the voltage terminal and ground terminal of the second printed circuit board.

Clause 15. The assembly according to clause 2, wherein a periphery of the proximal end portion of the first resilient strain relief housing is in sealing engagement with an internal wall of the through opening of the first lid and a periphery of the proximal end portion of the second resilient strain relief housing is in sealing engagement with an internal wall of through opening of the second lid.

Clause 16. The assembly according to clause 15, wherein each of the first and second resilient strain relief housings is made of rubber.

Clause 17. The assembly according to clause 1, wherein the cladding each of the first and second light diffusing optical fibers respectively abuts the front side of the first and second light emitting diode.

Clause 18. The assembly according to clause 2, wherein the through opening of the first lid comprises a first bore that opens to the front side of the lid and a second bore that opens to the backside of the first lid, the first bore having a first diameter and the second bore having a second diameter that is less than the first diameter, the end portion of the resilient strain relief housing residing inside the first bore.

Clause 19. The assembly according to clause 22, wherein the second bore of the first lid has a diameter that is 10% greater than an outer-most diameter of a portion of the first light diffusing optical fiber that passes through the second bore.

Clause 20. The assembly according to clause 18, wherein the first light diffusing optical fiber is secured inside the second bore of the first lid by use of an adhesive.

Clause 21. The assembly according to clause 1, wherein a refractive index matching material is disposed between the proximal end of the core of the first light diffusing optical fiber and the front side of the first light emitting diode.

Clause 22. The assembly according to clause 21, wherein the refractive index matching material is an adhesive.

Clause 23. The assembly according to clause 18, wherein a proximal end of the first bore of the first lid comprises a distal facing annular surface, the end of the resilient strain relief housing abutting the distal facing annular surface.

Clause 24. The assembly according to clause 1, further comprising an injection port that extends from an external surface of the first lid to the cavity of the first frame to facilitate an injection of an index matching material into the cavity of the first frame.

Group G Clauses:

Clause 1. An apparatus having an external surface susceptible to bacterial contamination, the apparatus comprising:
a housing having an external surface and internal channel, the housing being made of a material that is transparent to bacterial disinfecting ultraviolet or blue light;
a first light emitting diode having an energized state and a de-energized state, in the energized state the first light emitting diode emits bacterial disinfecting ultraviolet or blue light and in the de-energized state the first light emitting diode does not emit light;
a second light emitting diode having an energized state and a de-energized state, in the energized state the second light emitting diode emits visible light and in the de-energized state the first light emitting diode does not emit light;
a light diffusing optical fiber residing in the internal channel and configured to transmit both visible light and bacterial disinfecting ultraviolet or blue light, the light diffusing optical fiber being optically coupled to both the first and second light emitting diodes.

Figure 18J:
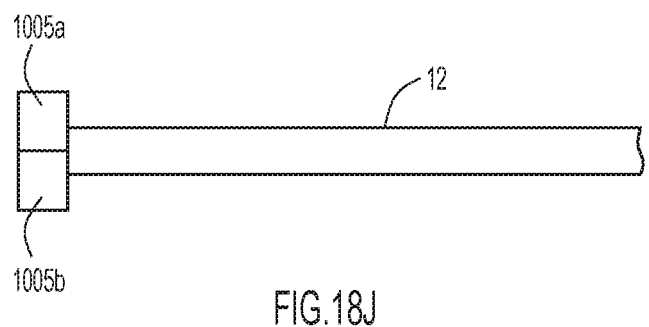

FIG. 18J schematically shows a single light diffusing fiber 12 being butt-coupled at one end to a first LED 1005*a* and a second LED 1005*b*.

Figure 18K:
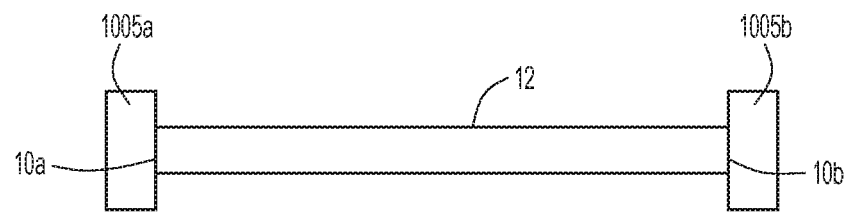

FIG. 18K schematically shows a single light diffusing fiber 12 being butt-coupled at a first end 10*a* to a first LED 1005*a* and at a second end 10*b* to a second LED 1005*b*.

Clause 2. The apparatus according to clause 1, wherein the light diffusing optical fiber has a core surrounded by a cladding, the core being butt-coupled to each of the first and second light emitting diodes.

Clause 3. The apparatus according to clause 1, wherein the light diffusing optical fiber has a core surrounded by a cladding, the core and cladding being butt-coupled to each of the first and second light emitting diodes.

Clause 4. The apparatus according to clause 1, wherein when the first light emitting diode is in the energized state the second light emitting diode is in the energized state.

Clause 5. The apparatus according to clause 1, wherein the visible light emitted by the second light emitting fiber is red light.

Clause 6. The apparatus according to clause 1, wherein when the first light emitting diode is in the de-energized state the second light emitting diode is in the energized state.

Clause 7. The apparatus according to clause 1, wherein the visible light emitted by the second light emitting diode is green light.

Clause 8. The apparatus according to clause 1, wherein the light diffusing optical fiber has a first end and a second end opposite the first end, the first end being optically coupled to the first and second light emitting diodes.

Clause 9. The apparatus according to clause 8, wherein the light diffusing optical fiber has a core surrounded by a cladding, the core at the first end of the light diffusing optical fiber being butt-coupled to both the first and second light emitting diodes.

Clause 10. The apparatus according to clause 1, wherein the light diffusing optical fiber has a first end and a second end opposite the first end, the first end being optically coupled to the first light emitting diode and the second end being optically coupled to the second light emitting diode as shown in FIG. 18K.

Clause 11. The apparatus according to clause 1, further comprising a third light emitting diode having an energized state and a de-energized state, in the energized state the third light emitting diode emits visible light and in the de-energized state the third light emitting diode does not emit light.

Figure 18L:
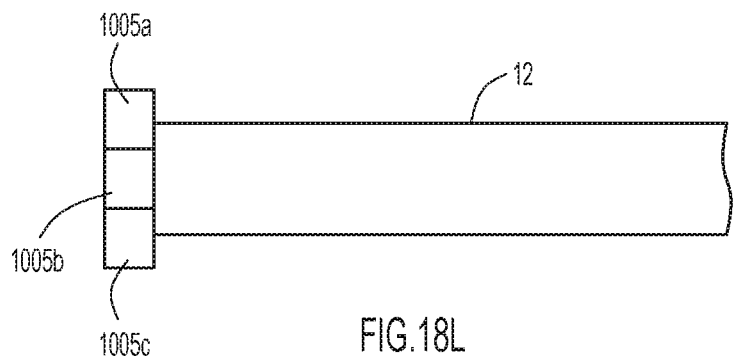

FIG. 18L schematically shows a single light diffusing fiber 12 being butt-coupled at one end to first, second and third LEDs 1005*a*, 1005*b* and 1005*c*.

Figure 18M:
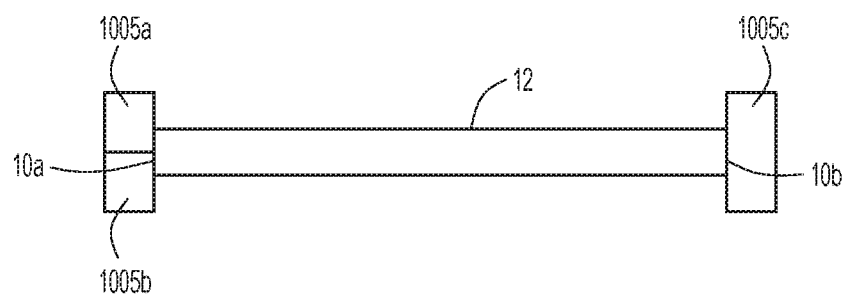

FIG. 18M schematically shows a single light diffusing fiber 12 being butt-coupled at a first end 10*a* to first and second LEDs 1005*a* and 1005*b*, and at a second end 10*b* to a third LED 1005*c*.

Figure 18N:
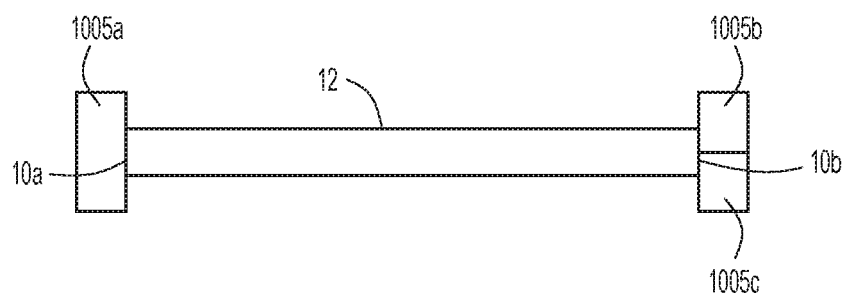

FIG. 18N schematically shows a single light diffusing fiber 12 being butt-coupled at a first end 10*a* to a first LED 1005*a* and at a second end 10*b* to second and third LEDs 1005*b* and 1005*c*.

Clause 12. The apparatus according to clause 11, wherein the second light emitting diode emits visible light of a first color, and the third light emitting diode emits light of a second color different than the first color.

Clause 13. The apparatus according to clause 12, wherein the first color is red and the second color is green.

Clause 14. The apparatus according to clause 12, wherein when the first light emitting diode is in the energized state the second light emitting diode is in the energized state.

Clause 15. The apparatus according to clause 12, wherein when the first light emitting diode is in the energized state the third light emitting diode is in the de-energized state.

Clause 16. The apparatus according to clause 15, wherein the first color is red.

Clause 17. The apparatus according to clause 16, wherein the second color is green.

Clause 18. The apparatus according to clause 11, wherein the light diffusing optical fiber has a first end and a second end opposite the first end, the first end being optically coupled to the first, second and third light emitting diodes.

Clause 19. The apparatus according to clause 11, wherein the light diffusing optical fiber has a core surrounded by a cladding, the core at the first end of the light diffusing optical fiber being butt-coupled to the first, second and third light emitting diodes.

Group H Clauses:

Clause 1. An apparatus having an external surface susceptible to bacterial contamination, the apparatus comprising:
a housing having an external surface and internal channel, the housing being made of a material that is transparent to bacterial disinfecting ultraviolet or blue light;
a first light emitting diode having an energized state and a de-energized state, in the energized state the first light emitting diode emits bacterial disinfecting ultraviolet or blue light and in the de-energized state the first light emitting diode does not emit light;
a second light emitting diode having an energized state and a de-energized state, in the energized state the second light emitting diode emits bacterial disinfecting ultraviolet or blue light and in the de-energized state the second light emitting diode does not emit light;
a third light emitting diode having an energized state and a de-energized state, in the energized state the second light emitting diode emits visible light and in the de-energized state the first light emitting diode does not emit light;

a light diffusing optical fiber residing in the internal channel and configured to transmit both visible light and bacterial disinfecting ultraviolet or blue light, the light diffusing optical fiber being optically coupled to the first, second and third light emitting diodes.

Figure 18O:
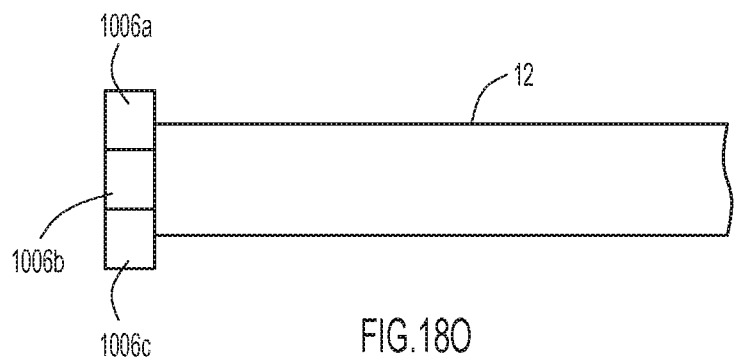

FIG. 18O schematically shows a single light diffusing fiber 12 being butt-coupled at one end to first, second and third LEDs 1006a, 1006b and 1006c.

Figure 18P:
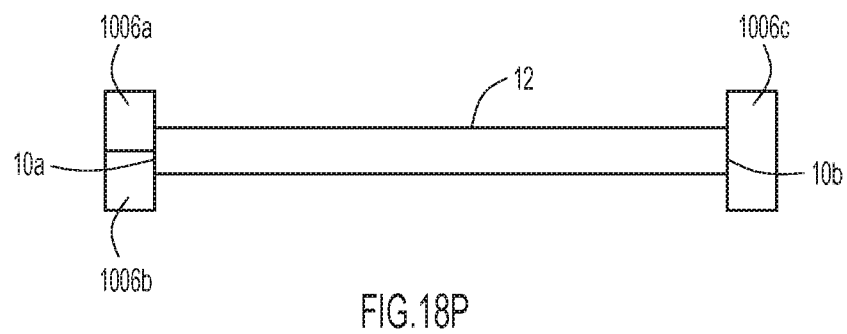

FIG. 18P schematically shows a single light diffusing fiber 12 being butt-coupled at a first end 10a to first and second LEDs 1005a and 1005b, and at a second end 10b to a third LED 1005c.

Figure 18Q:
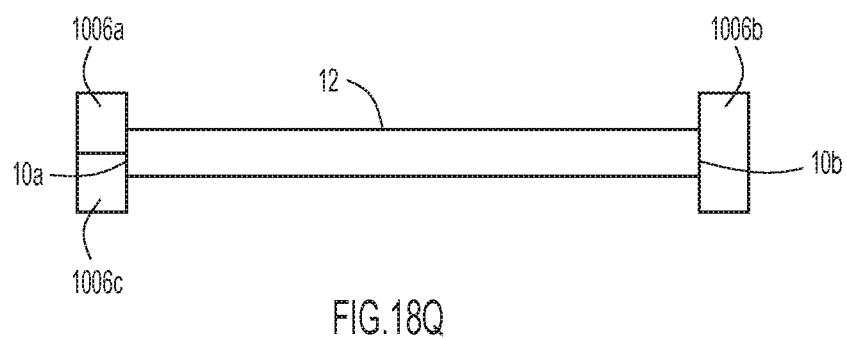

FIG. 18Q schematically shows a single light diffusing fiber 12 being butt-coupled at a first end 10a to first and third LEDs 1005a and 1005c, and at a second end 10b to a second LED 1005b.

Clause 2. The apparatus according to clause 1, wherein the light diffusing optical fiber has a core surrounded by a cladding, the core being butt-coupled to each of the first, second and third light emitting diodes.

Clause 3. The apparatus according to clause 1, wherein the light diffusing optical fiber has a core surrounded by a cladding, the core and cladding being butt-coupled to each of the first, second and third light emitting diodes.

Clause 4. The apparatus according to clause 1, wherein when at least one of the first and second light emitting diodes is in the energized state the third light emitting diode is in the energized state.

Clause 5. The apparatus according to clause 4, wherein the visible light emitted by the third light emitting diode is red.

Clause 6. The apparatus according to clause 1, wherein when both the first and second light emitting diodes are in the de-energized state the third light emitting diode is in the energized state.

Clause 7. The apparatus according to clause 6, wherein the visible light emitted by the third light emitting diode is green.

Clause 8. The apparatus according to clause 1, wherein the light diffusing optical fiber has a first end and a second end opposite the first end, the first end being optically coupled to the first light emitting diode, the second end being optically coupled to the second light emitting diode, and one of the first and second ends of the light diffusing optical fiber being optically coupled to the third light emitting diode.

Clause 9. The apparatus according to clause 8, wherein the light diffusing optical fiber has a core surrounded by a cladding, the core being butt-coupled to each of the first, second and third light emitting diodes.

Clause 10. The apparatus according to clause 8, wherein the light diffusing optical fiber has a core surrounded by a cladding, the core and cladding being butt-coupled to each of the first, second and third light emitting diodes.

Clause 11. The apparatus according to clause 8, wherein when at least one of the first and second light emitting diodes is in the energized state the third light emitting diode is in the energized state.

Clause 12. The apparatus according to clause 11, wherein the visible light emitted by the third light emitting diode is red.

Clause 13. The apparatus according to clause 8, wherein when both the first and second light emitting diodes are in the de-energized state the third light emitting diode is in the energized state.

Clause 14. The apparatus according to clause 13, wherein the visible light emitted by the third light emitting diode is green.

Clause 15. The apparatus according to clause 1, further comprising a fourth light emitting diode having an energized state and a de-energized state, in the energized state the third light emitting diode emits visible light and in the de-energized state the fourth light emitting diode does not emit light.

Figure 18R:
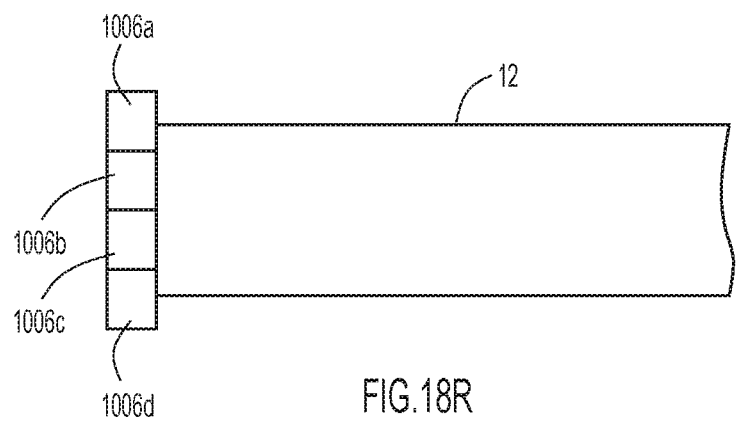

FIG. 18R schematically shows a single light diffusing fiber 12 being butt-coupled at one end to first, second, third and fourth LEDs 1006a, 1006b, 1006c and 1006d.

Figure 18S:
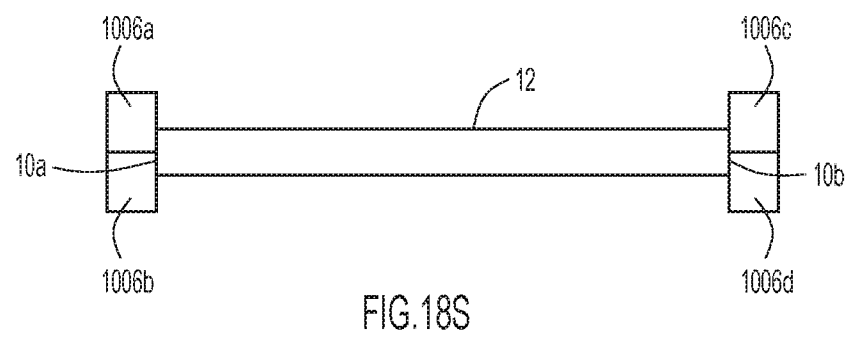

FIG. 18S schematically shows a single light diffusing fiber 12 being butt-coupled at a first end 10a to first and second LEDs 1006a and 1006b, and at a second end 10b to third and fourth LEDs 1006c and 1006d.

Figure 18T:
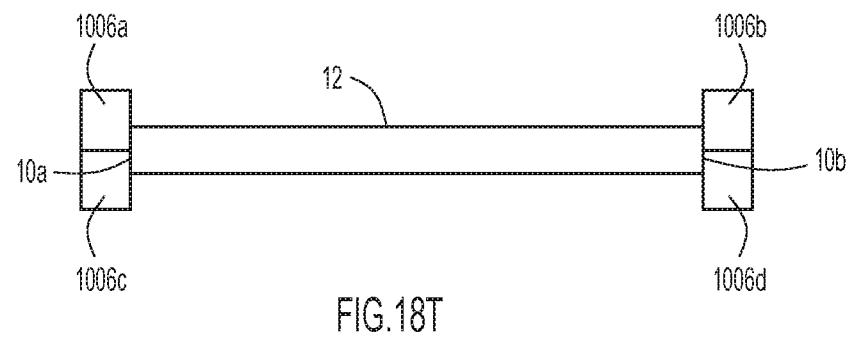

FIG. 18T schematically shows a single light diffusing fiber 12 being butt-coupled at a first end 10a to first and third LEDs 1006a and 1006c, and at a second end 10b to second and fourth LEDs 1006b and 1006d.

Figure 18U:
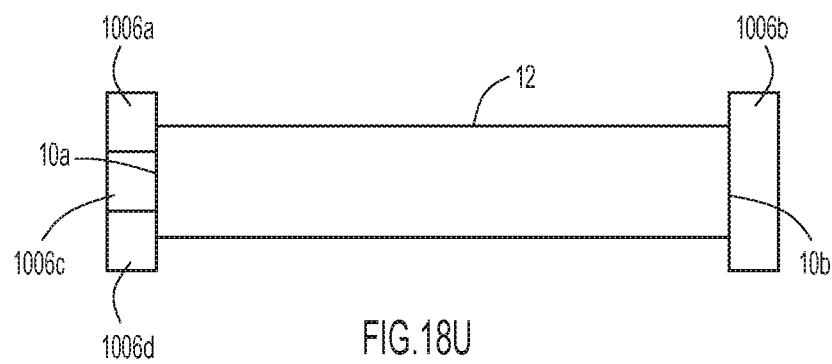

FIG. 18U schematically shows a single light diffusing fiber 12 being butt-coupled at a first end 10a to first, third and fourth LEDs 1006a, 1006c and 1006d and at a second end 10b second LED 1006b.

Clause 16. The apparatus according to clause 15, wherein the third light emitting diode emits visible light of a first color and the fourth light emitting diode emits light of a second color different than the first color.

Clause 17. The apparatus according to clause 16, wherein the first color is red and the second color is green.

Clause 18. The apparatus according to clause 16, wherein when one or both of the first and second light emitting diodes is in the energized state the third light emitting diode is in the energized state and the fourth light emitting diode is in the de-energized state.

Clause 19. The apparatus according to clause 17, wherein the first color is red and the second color is green.

Clause 20. The apparatus according to clause 16, wherein when both of the first and second light emitting diodes is in the de-energized state the third light emitting diode is in the de-energized state and the fourth light emitting diode is in the energized state.

Clause 21. The apparatus according to clause 17, wherein the first color is red and the second color is green.

Clause 22. The apparatus according to clause 15, wherein the light diffusing optical fiber has a first end and a second end opposite the first end, the first end being optically coupled to the first light emitting diode, the second end being optically coupled to the second light emitting diode, one of the first and second ends of the light diffusing optical fiber being optically coupled to the third light emitting diode, and one of the first and second ends of the light diffusing optical fiber being optically coupled to the fourth light emitting diode.

Clause 23. The apparatus according to clause 22, wherein the third light emitting diode emits visible light of a first color and the fourth light emitting diode emits light of a second color different than the first color.

Clause 24. The apparatus according to clause 23, wherein the first color is red and the second color is green.

Figure 20:
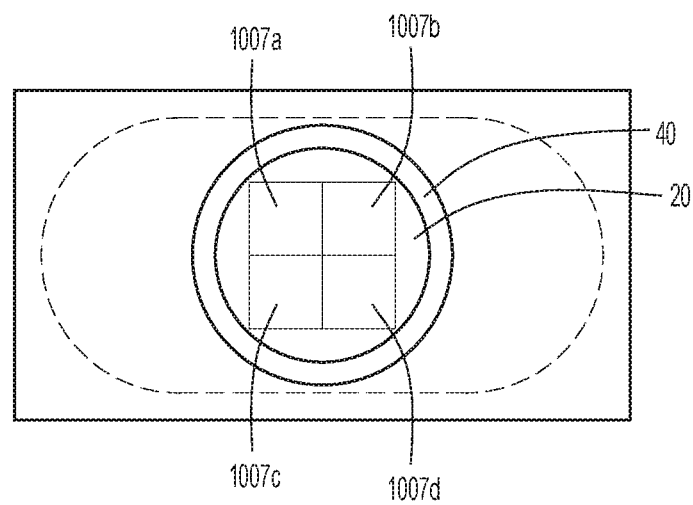
FIG. 20 illustrates an end of a single optical fiber being optically coupled to four light emitting diodes.

It is to be appreciated that the figures herein are not drawn to scale. In addition, in regard to the schematic representations of FIGS. 18A-U, in cases where an end of an optical fiber is optically coupled to two or more LEDs, the LEDs are shown aligned in a straight row. However, according to other implementations when an end of an optical fiber is optically coupled to two or three LEDs, the LEDs may be grouped together like that shown in FIGS. 11A and 11B. In instances where an end of an optical fiber 12 is optically coupled to four LEDs 1007a-d, the LEDs may be laid out in a rectangular fashion like that shown in FIG. 20.

What is claimed is:

1. An assembly comprising:
   a frame including a front side, a backside and a cavity located between the front side and backside that opens to the front side;
   first and second electrically conductive pads located on the frame;
   a first light emitting diode having an anode and a cathode, the first light emitting diode being located inside the cavity of the frame with the anode and cathode respectively being electrically coupled to the first and second electrically conductive pads;
   a first light diffusing optical fiber having a core and a cladding surrounding the core, the first light diffusing optical fiber including a proximal end portion having a first light receiving end that is butt-coupled to the first light emitting diode;
   a lid located distal to the first light emitting diode, the lid having a front side, a backside, and a through opening that extends between and through the front side and backside of the lid, the backside of the lid being attached to the front side of the frame, the first light diffusing optical fiber extending through and being supported in the through opening; and
   a printed circuit board having a voltage terminal and a ground terminal, the first electrically conductive pad of the frame being electrically connected to the voltage terminal and the second electrically conductive pad of the frame being electrically connected to the ground terminal.

2. The assembly according to claim 1, further comprising a resilient strain relief housing enclosing at least a portion of the first light diffusing optical fiber, the resilient strain relief housing having a proximal end that butts against the front side of the lid.

3. The assembly according to claim 1, further comprising a resilient strain relief housing enclosing at least a portion of the first light diffusing optical fiber, the resilient strain relief housing having a proximal end portion that resides inside the through opening of the lid.

4. The assembly according to claim 1, wherein the proximal end portion of the first light diffusing optical fiber protrudes proximally from the backside of the lid into the cavity of the frame.

5. The assembly according to claim 4, wherein the first light emitting diode includes a front side from which light is emitted, a distance between the backside of the lid and the front side of the first light emitting diode is equal to or less than 1 millimeter.

6. The assembly according to claim 1, wherein at least a portion of each of the first and second electrically conductive pads of the frame is located on the backside of the frame, the first electrically conductive pad being electrically coupled to the voltage terminal of the printed circuit board via a first electrically conductive pin that extends through a topside of the printed circuit board, the second electrically conductive pad being electrically coupled to the ground terminal of the printed circuit board via a second electrically conductive pin that extends through the topside of the printed circuit board.

7. The assembly according to claim 1, wherein at least a portion of each of the first and second electrically conductive pads of the frame is located on a bottom side of the frame, each of the voltage terminal and ground terminal of the printed circuit board respectively comprising first and second metallic pads residing on the top side surface of the printed circuit board, the first and second electrically conductive pads of the frame being respectively surface mounted in an electrically conducive manner to the first and second metallic pads of the printed circuit board.

8. The assembly according to claim 1, wherein the anode of the first light emitting diode is electrically coupled to the first electrically conductive pad by an electrically conductive wire having a first end and a second end, the first end being attached to and electrically coupled to the anode of the first light emitting diode, the second end being attached to and electrically coupled to the first electrically conductive pad.

9. The assembly according to claim 1, wherein the anode of the first light emitting diode is electrically coupled to a first electrical conductor element residing inside the frame, the first electrical conductor element comprising a first metallic mass that is electrically coupled to the first electrically conductive pad.

10. The assembly according to claim 9, wherein the anode of the first light emitting diode is electrically coupled to the first electrical conductor element by an electrically conductive wire having a first end and a second end, the first end being attached to and electrically coupled to the anode of the first light emitting diode, the second end being attached to and electrically coupled to the first electrical conductor element.

11. The assembly according to claim 1, wherein the cathode of the first light emitting diode is electrically coupled to a second electrical conductor element residing inside the frame, the second electrical conductor element comprising a second metallic mass that is electrically coupled to the second electrically conductive pad.

12. The assembly according to claim 11, wherein the cathode of the first light emitting diode is surface mounted to the second electrical conductor element.

13. The assembly according to claim 1, wherein the first light emitting diode comprises a light emitting side and each of the core and cladding at the light receiving end of the first light diffusing optical fiber is butt-coupled to the light emitting side of the first light emitting diode.

14. The assembly according to claim 1, wherein the through opening of the lid has a length dimension and a portion of the first light diffusing optical fiber residing in the through opening has an outer diameter dimension, the length dimension being greater than the outer diameter dimension.

15. The assembly according to claim 1, further comprising:
   a second light emitting diode located inside the cavity of the frame; and
   a second light diffusing optical fiber having a core and a cladding surrounding the core, the second light diffusing optical fiber having a light receiving end that is optically coupled to the second light emitting diode, the second light diffusing optical fiber extending through and being supported in the through opening of the lid.

16. The assembly according to claim 15, wherein the first light emitting diode emits ultraviolet light and the second light emitting diode emits visible light.

17. The assembly according to claim 15, wherein the first and second light emitting diodes are configured to be concurrently energized to concurrently deliver ultraviolet light and visible light into the first light diffusing light diffusing optical fiber.

18. The assembly according to claim 1, wherein the core of the first light diffusing light diffusing optical fiber has a distal end opposite the proximal end that is optically coupled to a second light emitting diode.

19. The assembly according to claim 18, wherein the first light emitting diode emits ultraviolet light and the second light emitting diode emits visible light.

\* \* \* \* \*

UNITED STATES PATENT AND TRADEMARK OFFICE
CERTIFICATE OF CORRECTION

PATENT NO. : 10,551,542 B1
APPLICATION NO. : 16/216112
DATED : February 4, 2020
INVENTOR(S) : Qing Tan et al.

Page 1 of 1

It is certified that error appears in the above-identified patent and that said Letters Patent is hereby corrected as shown below:

In the Claims

In Column 40, Line 6, Claim 7, delete "conducive" and insert -- conductive --, therefor.

In Column 40, Lines 64-65, Claim 17, delete "light diffusing light diffusing" and insert -- light diffusing --, therefor.

In Column 40, Line 67, Claim 18, delete "light diffusing light diffusing" and insert -- light diffusing --, therefor.

Signed and Sealed this
Third Day of November, 2020

Andrei Iancu
*Director of the United States Patent and Trademark Office*